US006306636B1

United States Patent
Haselkorn et al.

(10) Patent No.: US 6,306,636 B1
(45) Date of Patent: *Oct. 23, 2001

(54) NUCLEIC ACID SEGMENTS ENCODING WHEAT ACETYL-COA CARBOXYLASE

(75) Inventors: Robert H. Haselkorn; Piotr Gornicki, both of Chicago, IL (US)

(73) Assignee: Arch Development Corporation, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 08/934,386

(22) Filed: Sep. 19, 1997

(51) Int. Cl.[7] .............................. C12N 9/88; C12N 5/00; C12N 1/20; C07H 21/04

(52) U.S. Cl. ................ 435/232; 435/252.3; 435/252.33; 435/254.11; 435/254.21; 435/410; 435/320.1; 536/23.2; 536/23.6; 536/23.1

(58) Field of Search ................ 435/6, 232, 410, 435/252.3, 252.33, 254.11, 254.2, 254.21, 320.1; 536/23.1, 23.2, 23.6

(56) References Cited

U.S. PATENT DOCUMENTS

| | | | |
|---|---|---|---|
| 4,535,060 | 8/1985 | Comai | 435/172.3 |
| 4,757,011 | 7/1988 | Chaleff et al. | 435/172.1 |
| 4,769,061 | 9/1988 | Comai | 71/86 |
| 4,940,835 | 7/1990 | Shah et al. | 800/205 |
| 4,971,908 | 11/1990 | Kishore et al. | 435/172.1 |
| 5,162,602 | 11/1992 | Somers et al. | 800/235 |
| 5,225,326 | 7/1993 | Bresser et al. | 435/6 |
| 5,498,544 | 3/1996 | Gengenbach et al. | 435/320.1 |
| 5,539,092 | 7/1996 | Haselkorn et al. | 536/23.2 |
| 5,559,220 | 9/1996 | Roessler et al. | 536/23.6 |
| 5,756,290 | 5/1998 | Haselkorn et al. | 435/6 |
| 5,792,627 | 8/1998 | Haselkorn et al. | 435/69.1 |
| 5,801,233 | * 9/1998 | Haselkorn et al. | 536/23.6 |
| 5,854,420 | * 12/1998 | Ashton et al. | 800/205 |
| 5,910,626 | 6/1999 | Haselkorn et al. | 800/205 |
| 5,972,644 | 10/1999 | Haselkorn et al. | 435/69.1 |
| 6,069,298 | * 5/2000 | Gengenbach et al. | 800/278 |

FOREIGN PATENT DOCUMENTS

| | | |
|---|---|---|
| 2048040 | 1/1992 | (CA) . |
| 0068693 | 1/1983 | (EP) . |
| 0469810 | 2/1992 | (EP) . |
| 2057179 | 2/1990 | (JP) . |
| WO 93/11243 | 6/1993 | (WO) . |
| WO 96/32484 | 10/1993 | (WO) . |
| WO 94/08016 | 4/1994 | (WO) . |
| WO 94/17188 | 8/1994 | (WO) . |
| WO 94/23027 | 10/1994 | (WO) . |
| WO 94/29467 | 12/1994 | (WO) . |
| WO 95/29246 | 11/1995 | (WO) . |
| WO 96/31609 | 10/1996 | (WO) . |

OTHER PUBLICATIONS

Abu–Elheiga, Lutfi, et al., "Human Acetyl–CoA Carboxylase: Characterization, Molecular Cloning, And Evidence For Two Isoforms", *Proc. Natl. Acad. Sci. USA*, 92:4011–4015, Apr. 1995.

Aebersold et. al., "Internal Amino Acid Sequence Analysis Of Proteins Separated By One Or Two–Dimensional Gel Electrophoresis After in situ Protease", *Proc. Natl. Acad. Sci. USA*, 84:6970–6974, 1987.

Al–Feel et al., "Cloning Of The Yeast FAS3 Gene And Primary Structure Of Yeast Acetyl–CoA Carboxylase", *Proc. Natl. Acad. Sci. USA*, 89:4534–4538, 1992.

Alban et al., "Purification And Characterization Of 3–Methylcrotonyl–Coenzyme A Carboxylase From Higher Plant Mitochondria," *Plant. Physiol.*, 102:957–965, 1993.

Alix, Laboratory Methods; "A Rapid Procedure For Cloning Genes From 1 Libraries By Complementation Of *E. coli* Defective Mutants: Application To The fabE Region Of The *E. coli* Chromosome", *DNA*, 8:(10)779–789, 1989.

Ashton et al., "Molecular Cloning Of Two Different cDNAs For Maize Acetyl CoA Carboxylase," *Plant Mol. Biol.*, 24:35–49, 1994.

Bai et al., "Analysis Of The Biotin–Binding Site On Acetyl–CoA Carboxylase From Rat", *Eur. J. Biochem,*. 182:239–245, 1989.

Best, E.A., and Knauf, V.C., "Organization And Nucleotide Sequence Of The Genes Encoding The Biotin Carboxyl Carrier Protein And Biotin Cargboxylase Protein Of *Pseudomonas Aeruginosa* Acetyl Coenzyme A Carboxylase," *J. Bacteriol.*, 175:6881–6889, Nov. 1993.

Bettey et al., "Purification And Characterization Of Acetyl–coA Carboxylase From Developing Pea Embryos," *J. Plant. Physiol.*, 140:513–520, 1992.

Bowness et al., "Conservation Of T Cell Receptor Usage By HLA B24–Resitricted Influenza–Specific Cytotoxic T Lymphocytes Suggests A General Pattern For Antigen–Specific Major Histocompatibility Complex Class I–Restricted Responses," *Eur. J. Immunol.*, 23:1417–1421, 1993.

Brown, "How To Obtain A Clone Of A Specific Gene", In *Gene Cloning: An Introduction*, 2nd Edition, Chapman & Hall, New York, Chapter 8, p. 153–177, 1990.

Browner et al., "Sequence Analysis, Biogenesis And Mitochonoriald Import Of The Alpha–Subunit Of Rat Liver Propionyl–CoA Carboxylase," *J. Biol. Chem.*, 264:12680–12685.

(List continued on next page.)

Primary Examiner—Nashaat T. Nashed
(74) Attorney, Agent, or Firm—Fulbright & Jaworski LLP

(57) ABSTRACT

The present invention provides isolated and purified polynucleotides that encode plant polypeptides that participate in the carboxylation of acetyl-CoA. Also provided are methods for identifying such nucleic acid segments and polypeptides. Processes for altering acetyl-CoA carboxylation, increasing herbicide resistance of plants and identifying herbicide resistant variants of acetyl-CoA carboxylase are also provided.

28 Claims, 8 Drawing Sheets-

OTHER PUBLICATIONS

Figure 1A:
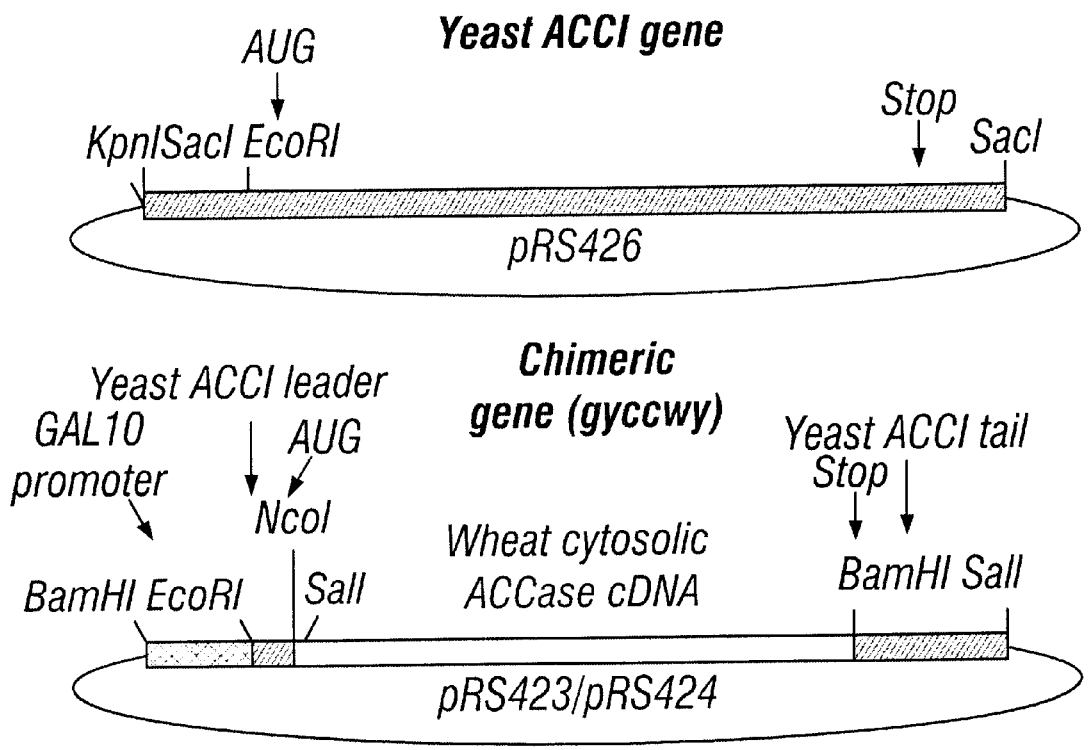

Burton et al., "Fat Metabolism In Higher Plants. XXXII. Control Of Plant Acetyl–CoA Carboxylase Activity", *Arch. Biochem. Biophys.*, 117(3):604–614, as cited in *Chem. Abstr.*, 66:2471, Abstract No. 26251v, 1967.

Chen et al., "Purification And Characterization Of 3–Methylocrotonyl–CoA Carboxylase From Somatic Embryos Of Dacuscarota", *Arch. Biochem. Biophys.*, 305:103–109, 1993.

Chirala, S.S., "Coordinated Regulation And Inositol–Mediated And Fatty Acid–Mediaed Repression Of Fatty Acid Synthase Genes In *Saccharomyces cerevisiae*," *Proc. Natl. Acad. Sci. USA*, 89:10232–10236, 1992.

Claesson et al., "cDNA Clone For The Human Invariant γ Chain Of Class II Histocompatibility Antigens And Its Implications For The Protein Structure", *Proc. Natl. Acad. Sci. USA*, 80:7395–7399, Dec. 1983.

Cozens et al., "A Sixth Subunit Of ATP Synthase, An $F_0$ Component, Is Encoded In The Pea Chloroplast Genome", *EMBO J.*, 5:217–222, 1986.

Craig et al., "Genetic Engineering Of Micro–Algae", Micro–Algal Biotechnology Cambridge University Press, 16:415–455, 1988.

Egin–Buehler et al., "Comparison Of Acetyl Coenzyme A Carboxylases (ED 6.4.1.2) From Parsley (*Petroselinum hortense*) Cell Cultures And Wheat Germ", *Arch Biochem Biophys.*, 203(1):90–100, Aug. 1980, as cited in *Biological Abstracts*, vol. 71, Abstract 5758, 1981..

Egin–Buhler, B. and Ebel, J., "Improved Purification And Further Characterization Of Acetyl–CoA Carboxylase From Cultured Cells Of Parsley (*Petroselinum hortense*)," *Eur. J. Biochem.*, 133:335–339, 1983.

Egli et al., "A 223 kDa Subunit of Acetyl–CoA Carboxylase is Encoded by the Acc1 Gene," *Maize Genetics Cooperation Newsletter*, 66:94–95, 1992.

Egli et al., "Characterization Of Maize Acetyl–Coenzyme A Carboxylase," *Plant. Physiol.*, 101:499–506, 1993.

Egli et al., "Purification And Characterization Of Maize Acetyl–CoA Carboxylase," *Plant Physiol.*, 96(1):92(581), 1991.

Egli et al., "Purification Of Maize Leaf Acetyl–CoA Carboxylase", *Maize Genetics Cooperation Newsletter*, 65:95, 1991.

Egli, Margaret A., et al., "A Maize Acetyl–Coenyme A Carboxylase cDNA Sequence", *Plant Physiol.*, 108:1299–1300, 1995.

Eichholtz et al., "Expression Of Mouse Dihydrofolate Reductase Gene Confers Methotrexate Resistance In Transgenic Petunia Plants", *Somatic Cell and Molecular Genetics*, 13:(1)67–76, 1987.

Elborough et al., "Isolation Of cDNAs From *Brassica napus* Encoding The Biotin–Binding And Transcarboxylase Domains Of Acetyl–CoA Carboxylase: Assignment Of The Domain Structure In A Full–Length *Arabidopsis thaliana* Genomic Clone", *Biochem. J.*, vol. 301, pp. 599–605, 1994 and EMBL Sequence Database, Release 40, Jun. 10, 1994, Accession No. X77382, Elborough, *B.napus* (pRS1) mRNA for acetyl CoA carboxylase.

Elborough et al., "Regulation Of Primary Storage Products Of Oil Seeds By Manipulating The Level Of Genes Involved In Lipid Metabolism On Plant Acetyl CoA Carboxylase", *J. Cell. Biol.*, (Suppl. 18A):113, Abstract X1–418, 1994. (XP002026102).

Elborough et al., "Studies On Wheat Acetyl Coa Carboxylase And The Cloning Of A Partial cDNA," *Plant Mol. Biol.*, 24:21–34, 1994.

Evenson et al., "Purification And Characterization Of Acetyl–Coa Carboxylase From Diclofop–Resistant And Susceptible Italian Ryegrass (*Lolium Multiflorum*)", *Plant Physiol.*, 99(1 Suppl):59, Abstr. #351, 1992.

Fall, R.R., "Analysis Of Microbiol Biotin Proteins," *Meth. Enzymol.*, 62:390–398, 1979.

Fernandez and Lamppa, "Acyl Carrier Protein Import Into Chloroplasts," *J. Biol. Chem.*, 266(11):7220–7226, Apr. 1991.

Fraley et al., "The SEV System: A New Disarmed TI Plasmid Vector System for Plant Transformation," *Bio/Technology*, 3:629–635, Jul. 1985.

Fu, Hongyong, et al., "High–Level Tuber Expression And Sucrose Inducibility Of A Potato Sus4 Sucrose Synthase Gene Require 5' and 3' Flanking Sequences and the Leader Intron", *Plant Cell*, 7:1387–1394, Sep. 1995.

Gamulin et al.,"Six *Schizosaccharomyces pombe* tRNA Genes Including A Gene For A tRNA$^{Lys}$ With An Intervening Sequence Which Cannot Base–Pair With the Anticodon", *Nucl. Acids Res.*, 11:8537–8546, 1983.

Golden, "Genetic Engineering Of The Cyanobacterial Chromosome", *J. Bacteriol.*, 165 215–231, 1986.

Gordon–Kamm et al., "Transformation Of Maize Cells And Regeneration Of Fertile Transgenic Plants", *The Plant Cell*, 2:603–618, Jul. 1990.

Gornicki et al., "Genes For Two Subunits Of Acetyl Coenzyme A Carboxylase Of Anabaena sp. Strain PCC 7120: Biotin Carboxylase And Biotin Carboxyl Carrier Protein," *J. Bacteriol.*, 175(16):5268–5272, Aug. 1993.

Gornicki et al., "Plastid–Localized Acetyl–Co A Carboxylase Of Bread Wheat Is Encoded By A Single Gene On Each Of The Three Ancestral Chromosome Sets", *Proc. Natl. Acad. Sci. USA*, 94:14179–14184, Dec. 1997.

Gornicki, P. and Haselkorn, R., "Wheat Acetyl–CoA Carboxylase," *Plant Mol. Biol.*, 22:547–552, 1993.

Gornicki, P., et al., "Wheat Acetyl–Coenzyme A Carboxylase: cDNA And Protein Structure", *Proc. Natl. Acad. Sci. USA*, 91:6860–6864, Jul. 1994.

Guchhait et al., "Acetyl Coenzyme A Carboxylase System Of *Escherichia coli*", *J. Biol. Chem.*, 249:(20)6633–6645, 1974.

Guss et al., "Region X, The Cell–Wall–Attachment Part Of Staphylococcal Protein A", *Eur. J. Biochem.*, 138:413–420, 1984.

Ha et al., "Cloning Of Human Acetyl–CoA Carboxylase cDNA," *Eur. J. Biochem.*, 219:297–306, 1994.

Ha et al., "Critical Phosphorylation Sites For Acetyl–CoA Carboxylase Activity," *J. Biol. Chem.*, 269(35):22162–22168, Sep. 1994.

HaBlacher et al., "Acetyl–CoA Carboxylase From Yeast Is An Essential Cnzyme And Is Regulated By Factors That Control Phospholipid Metabolism," *J. Biol. Chem.*, 268:10946–10952, May 1993.

Hardie et al., "The AMP–Activated Protein Kinase: A Multisubstrate Regulator Of Lipid Metabolism," *Trends Biochem. Sci.*, 14:20–23, 1989.

Harwood, "Fatty Acid Metabolism", *Ann. Rev. Plant Physiol. Plant Mol. Biol.*, 39:101–138, 1988.

Harwood, "Medium And Long–Chain Fatty Acid Synthesis In, The Metabolism, Structure, And Function Of Plant Lipids", Stumpf et al., (Eds.), pp. 465–472.

Hawke et al., "Acetyl–CoA–Carboxylase Activity In Normally Developing Wheat Leaves", *Planta,* 171(4):489–495, 1987.

Hawke et al., "Acetyl–Coenzyme A Carboxylase In Species of Triticum Of Different Ploidy", *Planta,* 181(4):543–546, 1990.

Haymerle et al., "Efficient Construction Of cDNA Libraries In Plasmid Expression Vectors Using An Adaptor Strategy", *Nucl. Acids Res.,* 14:(21)8615–8624, 1986.

Heinstein et al., "Fat Metabolism In Higher Plants. XXXVII. Properties Of Wheat Germ Acetyl Coenzyme A Carboxylase", *J. Biol. Chem.,* 244(19):5374–5381, 1969.

Holland et al.,"Identification And Characterization Of hetA, A Gene That Acts Early In The Process Of Morphological Differentation Of Heterocysts", *J. Bacteriol.,* 172:3131–3137, 1990.

Holt et al., "Mechanisms And Agronomic Aspects Of Herbicide Resistance," *Annu. Rev. Plant. Physiol. Plant Mol. Biol.,* 44:203–229, 1993.

International Search Report for PCT/US93/09340 Mailed Feb. 22, 1994. (ARCD:058P).

International Search Report dated Mar. 27, 1997 for PCT/US96/05095. (ARCD:221P).

Jaye et al., "Isolation Of A Human Anti–Haemophilic Factor IX cDNA Clone Using A Unique 52–Base Synthetic Oligonucleotide Probe Deduced From The Amino Acid Sequence Of Bovine Factor IX", *Nucl. Acids Res.,* 11(8):2325–2335, 1983.

Joachimiak et al., "Wheat Cytosolic Acetyl–CoA Carboxylase Complements An ACC1 Null Mutation In Yeast", *Proc. Natl. Acad. Sci. USA,* 94:9990–9995, 1997.

Kannangara and Stumpf, "Fat Metabolism In Higher Plants LIV. A Prokaryotic Type Acetyl CoA Carboxylase In Spinach Chloroplasts", *Arch. Biochem. Biophys.,* 152:83–91, 1972.

Ke et al., "Structure Of The CAC1 Gene And In Situ Characterization Of Its Expression", *Plant Physiol.,* 113:357–365, 1997.

Knowles, "The Mechanism Of Biotin–Dependent Enzymes", *Ann. Rev. Biochem.* 58:195–221, 1989.

Kondo et al., "Acetyl–Coa Carboxylase From *Escherichia coli:* Gene Organization And Nucleotide Sequence Of The Biotin Carboxylase Subunit", *Proc. Natl. Acad. Sci. USA,* 88:9730–9733, Nov. 1991.

Konishi and Sasaki, "Compartalization Of Two Forms Of Acetyl–CoA Carboxylase In Plants And The Origin Of Their Tolerance Toward Herbicides", *Proc. Natl. Acad. Sci. USA,* 91:3598–3601, Apr. 1994.

Lamppa et al., "Structure And Developmental Regulation Of A Wheat Gene Encoding The Major Chlorophyll a/b–Binding Polypeptide", *Mol. Cell Bio.,* 5(6):1370–1378, 1985.

Li and Cronan, "Putative Zinc Finger Protein Encoded By A Conserved Chloroplast Gene Is Very Likelly A Subunit Of A Biotin–Depenedent Carboxylase," *Plant Mol. Biol.,* 20:759–761, 1992.

Li et al., "The Gene Encoding The Biotin Carboxylase Subunit Of *Escherichia coli* Acetyl–CoA Carboxylase", *J. Biol. Chem.,* 267(2):855–863, Jan. 1992.

Li, S–1 and Cronan, J.E., "Growth Rate Regulation Of *Escherichiacoli* Acetyl Coenzyme A Carboxylase, Which Catalyzes The First Commited Step Of Lipid Biosynthesis", *J. Bacteriol.,* 175(2):332–340, Jan. 1993.

Lichtenthaler, "Mode Of Action Of Herbicides Affecting Acetyl–CoA Carboxylase And Fatty Acid Biosynthesis", *Z. Naturforsch,* 45c:521–528, Dec. 1990.

Livine et al., "Acetyl–Coenzyme A Carboxylase From The Marine Prymnesiophyte *Isochrysis galbana",* *Plant Cell Physiol.,* 31:(6)851–858, 1990.

Lopez–Casillas et al., "Heterogeneity At The 5' End Of Rat Acetyl–Coenzyme A Carboxylase mRNA", *J. Biological Chem.,* 264(13):7176–7184, 1989.

Lopez–Casillias et al., "Structure Of The Coding Sequence And Primary Amino Acid Sequence Of Acetyl–Coenzyme A Carboxylase", *Proc. Natl. Acad. Sci. USA,* 85:5784–5788, Aug. 1988.

Luo et al., "Structural Features Of The Acetyl–CoA Carboxylase Gene: Mechanisms For The Generation Of mRNAs With 5' End Heterogeneity", *Proc. Natl. Acad. Sci. USA,* 86:4042–4046, Jun. 1989.

Luo et al., "Molecular Cloning And Analysis Of A cDNA Coding For The Bifunctional Dihydrofolate Reductase–Thymidylate Synthase Of *Daucus–carota,"* *Plant Mol. Biol.,* 22:427–435, 1993.

Marshall et al., "Allelic mutations in acetyl–coenzyme A carboxylase confer herbicide tolerance in maize," *Theor. Appl. Genet.,* 83:435–442, 1992.

Muramatsu et al., "Nucleotide Sequence Of The fabE Gene And Flanking Regions Containing A Bent DNA Sequence Of *Escherichia coli",* *Nucl. Acids Res.,* 17(10):3982, 1989.

Nielsen et al., "Fat Metabolism In Higher Plants. Further Characterization Of Wheat Germ Acetyl Coenzyme A Carboxylase",*Arch. Biochem. Biophys.,* 192(2):446–456, 1979.

Nikolau et al., "Acetyl–Coenzyme A Carboxylase In Maize Leaves," *Arch. Biochem.Biophys.,* 211:605–612, 1981.

Nikolau et al., "Tissue Distribution Of ACC In Leaves," *Plant Physiol.,* 75:895–901, 1984.

Nikolau et al., "Use of Streptavidin to Detect Biotin–Containing Proteins in Plants,"*Anal. Biochem.,* 149(2):448–453, 1985.

Omirulleh et al., "Activity Of A Chimeric Promoter With The Doubled CaMV 35S Enhancer Element In Protoplast–Derived Cells And Transgenic Plants In Maize," *Plant Mol. Biol.,* 21:415–428, 1993.

Page, Rachel A., et al., "Acetyl–CoA Carboxylase Exerts Strong Flux Control Over Lipid Synthesis In Plants", *Biochem. at Biophys. Acta,* 1210:369–372, 1994.

Palosarri et al., "Comparison Of Acetyl–Coenzyme A Carboxylase From Graminicide–Tolerant and Susceptible Maize Lines", *Plant Physiol.,* 99(1Suppl):59, Abstr. #352, 1992.

Pansegrau et al., "Nucleotide Sequence Of The Kanamycin Resistance Determinant Of Plasmid RP4: Homology To Other Aminoglycoside 3'–Phosphotransferases", *Plasmid,* 18:193–204, 1987.

Pecker et al., "A Single Polypeptide Catalyzing The Conversion Of Phytoene To z–Carotene Is Transcriptionally Regulated During Tomato Fruit Ripening", *Proc. Natl. Acad. Sci. USA,* 89:4962–4966, 1992.

Phung et al., "Genes For Fatty Acid Biosynthesis In The Cyanobacterium Synechococcus sp. Strain PCC 7942", *95th Gen. Meet. Am. Soc.Microbiol.,* May 21–25, 1995, Abstract H–182, ISSN:1060–2011, XP000601370.

Podkowinski et al., "Structure Of A Gene Encoding A Cytosolic Acetyl–CoA Carboxylase Of Hexaploid Wheat", *Proc. Natl. Acad. Sci.,* vol. 93(5):1870–1874, Mar. 1996, ISSN:0027–8424, XP002026103; and EMBL Sequence Database, Release 47, Accession No. U39321, Apr. 5, 1996, *Triticum aestivum* acetyl–CoA carboxylase gene, exons 1–30, complete cds.

Post–Beittenmiller et al., "In Vivo Pools Of Free And Acylated Acyl Carrier Proteins In Spinach", *J. Biol. Chem.,* 266(3):1858–1865, 1991.

Post–Beittenmiller et al., "Regulation Of Plant Fatty Acid Biosynthesis," *Plant. Physiol.,* 100:923–930, 1992.

Reitzel, L. and Nielsen, N.C., "Acetyl–Coenzyme A Carboxylase During Development Of Plastids In Wild–Type And Mutant Barley Seedlings," *Eur. J. Biochem.,* 65:131–138, 1976.

Rendina et al., "Kinetic Characterization, Stereoselectivity And Species Selectivity Of The Inhibition Of Plant Acetyl–Coa Carboxylase By The Aryloxyphenoxypropionic Acid Grass Herbicides," *Arch. Biochem. Biophys.,* 265:219–225, 1988.

Roesler et al., Structure And Expression Of An Arabidipsis Acetyl–Coenzyme A Carboxylase Gene, *Plant Physiol.,* 105:611–617, 1994 (XP 002013209).

Roesler, et al., Targeting Of The Arabidopsis Homomeric Acetyl–Coenzyme A Carboxylase To Plastids Of Rapeseeds, *Plant Physiol,* 113:75–81, 1997.

Roessler et al., "Characterization Of The Gene For Acetyl–CoA Carboxylase From The Alga *Cyclotella cryptica*", *Plant Physiol.,* 99(1 Suppl):19 Abstr. #113, 1992.

Roessler, P.G. and Ohlrogge, J.B., "Cloning And Characterization Of The Gene That Encodes Acetyl–Coenzyme A Carboxylase In The Alga *Cyclotella cryptica,*" *J. Biol. Chem.,* 268:19254–19259, Sep. 1993.

Roessler et al., "Purification And Characterization Of Acetyl–CoA Carboxylase from the Diatom *Cyclotella cryptica",* *Plant Physiol.,* 92:73–78, 1990.

Samols et al., "Evolutionary Conservation Among Biotin Enzymes", *J. Biol. Chem.,* 263(14):6461–6464, May 1988.

Sasaki et al., "Chloroplast–Encloded Protein As A Subunit Of Acetyl–CoA Carboxylase In Pea Plant," *J. Biol. Chem.,* 268(33):25118–25123, Nov. 1993.

Schneider and Haselkorn, "RNA Polymerase Subunit Homology Among Cyanobacteria, Other Eubacteria, And Archaebacteria," *J. Bacteriol.,* 170(9):4136–4140, Sep. 1988.

Schulte et al., "Multi–Functional Acetyl–CoA Carboxylase From *Brassica napus* Is Encoded By A Multi–Gene Family: Indication For Plastidic Localization Of At Least One Isoform", *Proc. Natl. Acad. Sci. USA,* 94:3465–3470, 1997.

Sedlak, "Iowa State Scientists Clone A Key Plant Oil Production Gene", *Genetic Eng. News,* May 1991.

Shorrosh, Basil S., et al., "Molecular Cloning, Characterization, And Elicitation Of Acetyl–CoA Carboxylase From Alfalfa", *Proc. Natl. Acad. Sci. USA,* 91:4323–4327, May 1994.

Slabas and Hellyer, "Rapid Purification Of A High Molecular Weight Subunit Polypeptide Form Of Rape Seed Acetyl CoA Carboxylase", *Plant Sci.,* 39:177–182, 1985.

Slabas et al., "The Biochemistry And Molecular Biology Of Plant Lipid Biosynthesis", *Plant Mol. Biol.,* 19:169–191, 1992.

Slabas, Hellyer and Bambridge, The Basic Polypeptide Subunit Of Rape Leaf Acetyl–CoA Carboxylase Is A 220 kDa Protein, *Biochem. Soc. Trans.,* 19:716, 1986.

Somers et al., "Expression Of The Acc1 Gene–Encoded Acetyl–Coenzyme A Carboxylase In Developing Maize (*Zea mays* L.) Kernels," *Plant Physiol,* 101:1097–1101, 1993.

Somerville, A. and Browse, J., "Plant Lipids: Metabolism, Mutants, And Membranes," *Science,* 252:80–87, 1991.

Suzuki et al., "Molecular Cloning Of cDNA For Human Poly(ADP–Ribose) Polymerase And Expression Of Its Gene During HL–60 Cell Differentiation", *Biochem. and Biophys. Communications,* 146:403–409, 1987.

Takai et al., "Primary Structure Of Chicken Liver Acetyl–CoA Carboxylase Deduced From cDNA Sequence", *J. Biol. Chem.,* 263(6):2651–2657, 1988.

Toh et al., "Molecular Evolution Of Biotin–Dependent Carboxylases," *Eur. J. Biochem.,* 215:687–696, 1993.

Tomasiewicz and McHenry, "Sequence Analysis Of The *Escherichia coli* dnaE Gene", *J. Bacteriol.,* 169(12):5735–5744, Dec. 1987.

Turnham, E., and Northcote, D.H., "Changes In The Activity Of Acetyl–CoA Carboxylase During Rape–Seed Formation," *Biochem. J.,* 212:223–229, 1983.

Valentin et al., Glutamate Synthase Is Plastid–Encoded In A Red Alga: Implications For The Evolution Of Glutamate Synthases, *Plant Mol. Biol.* 23:77–85, 1993; EMBL Sequence Database Release 39, 1994, Accession No. Z33874, XP002026098.

Vasil et al., "Herbicide Resistant Fertile Transgenic Wheat Plants Obtained By Microprojectile Bombardment Of Regenerable Embryogenic Callus", *Bio/Technology,* 10:667–674, 1992.

Walker et al., Fluazifop, "A Grass–Selective Herbicide Which Inhibits Acetyl–CoA Carboxylase In Sensitive Plant Species", *Biochem. J.,* 254:307–310, 1988.

Watson et al., "Recombination At The Molecular Level, *Molecular Biology of the Gene",* The Benjamin/Cummings Publishing Company, Inc., Menlo Park, California, Chapter 11, p. 313, 1987.

Weaver, Lisa M., et al., "Molecular Cloning Of The Biotinylated Subunit Of 3–Methylcrotonyl–Coenzyme A Carboxylase Of *Arabidopsis thaliana",* *Plant Physiol.,* 107:1013–1014, 1995.

Winz, Robert, et al., "Unique Structural Features And Differential Phosphorylation Of The 280–kDa Component (Isozyme) Of Rat Liver Acetyl–CoA Carboxylase", *J. Biol. Chem.,* 269(2)14438–14445, 1994.

Wood, H.G., and Barden, R.E., "Biotin enzymes," *Ann. Rev. Biochem.,* 46:385–413, 1977.

Wurtele et al., "Plants Contain Multiple Biotin Enzymes: Discovery Of 3–Methylcrotonyl–CoA Carboxylase, Propionyl–CoA Carboxylase And Pyruvate Carboxylase In The Plant Kingdom", *Arch. Biochem. Biophys.,* 278(1):179–186, Apr. 1990.

Wurtele, E.S., and Nikolau, B.J., "Differential Accumulation Of Biotin Enzymes During Carrot Somatic Embryogenesis," *Plant. Physiol.* 99:1699–1703, 1992.

Yanai, Yukihiro, et al., "Genomic Organization Of 251 kDa Acetyl–CoA Carboxylase Genes In Arabidopsis: Tandem Gene Duplication Has Made Two Differentially Expressed Isozymes", *Plant Cell Physiol.,* 36(5):779–787, 1995.

\* cited by examiner

Aryloxyphenoxypropionate:
Haloxyfop

Cyclohexanediones:
Sethoxydim
X=CH₂CH(CH₃)SCH₂CH₃;Y=CH₂CH₂CH₃;R=CH₂CH₃
Cethoxydim
X=C(SCH₃)CH₂;Y=CH₂CH₃;R=CH₂CH=CH₂Cl
        \\   /
         CH₂

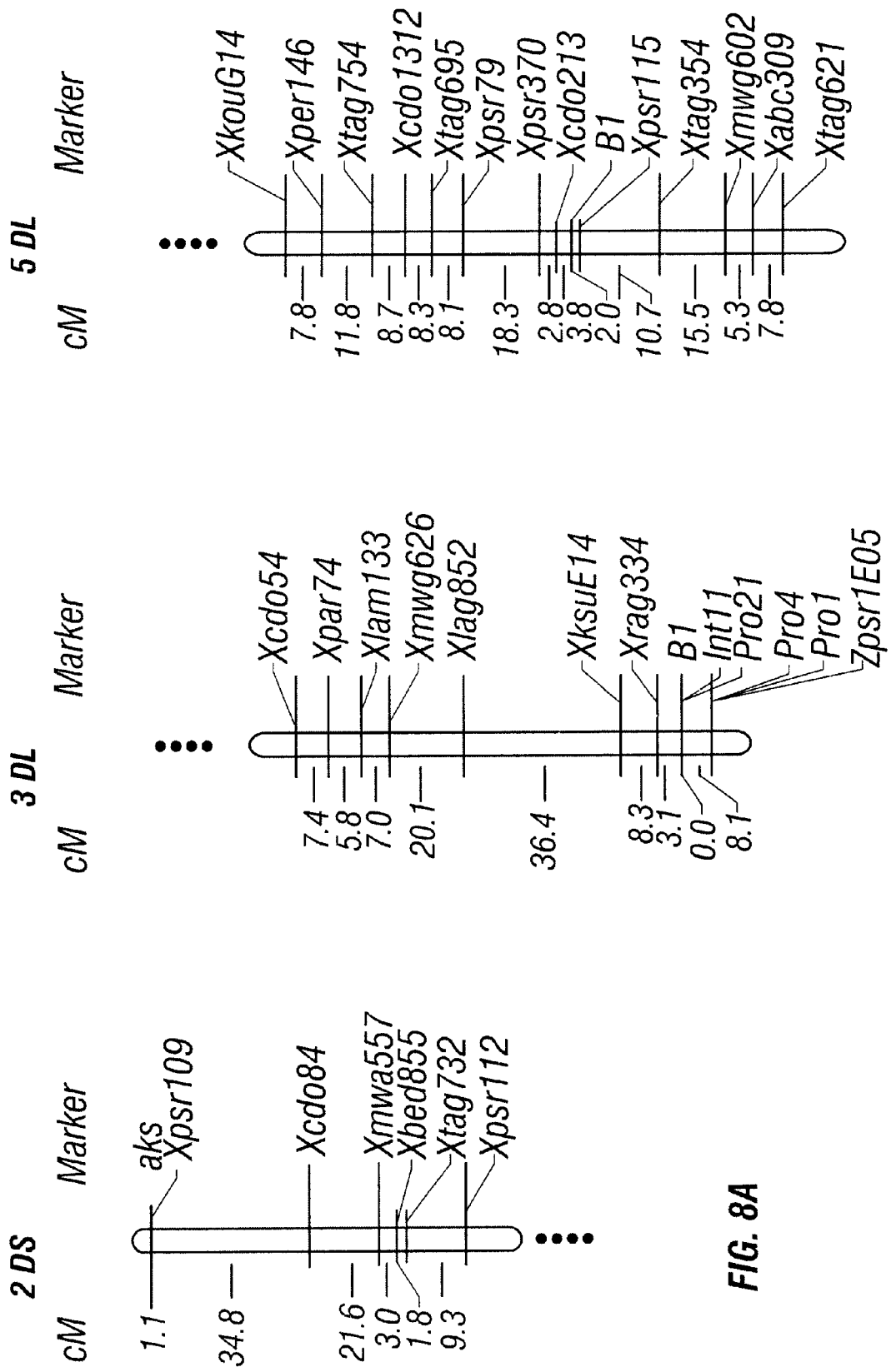

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
        (A) LENGTH: 1645 base pairs
        (B) TYPE: nucleic acid
        (C) STRANDEDNESS: single
        (D) TOPOLOGY: linear (xi) SEQUENCE DESCRIPTION: SEQ ID NO:1:

| | | | | | |
|---|---|---|---|---|---|
| TTCATCTCCC | ACACATAACA | CGAAAACCAG | AACAAAACAC | CCCGCGACTA | CGATTGGAGA | 60 |
| TGTAGGCATC | AAAGGCGTCG | AGACCTATGC | AAGCACACC | ATCCATCTGT | GACCATGAAG | 120 |
| CACAACTATT | CATCTTCCAC | CAGCCCCGCC | TCCATGAATG | CTGGACTAGA | ATGTGAATGT | 180 |
| GTACTGCCGC | GTGCGCGTGT | GTCCGTTTGC | CTCGGCGGAA | CACCACCAGC | CCGGTACAGC | 240 |
| AAGCGATTTG | TGACCGTCAA | CTAAATTTGG | AATCGTTGGC | GCATAATCAT | TGGAATATGC | 300 |
| ATGTCTCCGT | TACAAGGCAC | GGACAATTAG | CTAGACAACA | CACCCATGAT | GCAATTAGCT | 360 |
| AGACAATTAG | CTAGACAACA | CACCCACGGA | CAATTAGCAC | CGACGACTAC | GGGACGGCCG | 420 |
| GACGGTGACG | GGGACGTGGA | CGAAGCCGAG | CGGAGCACGC | CACCGGAGCG | GAGGGAGCGA | 480 |
| GCTGAGCACA | TCGAGTCCAG | GGCAGACACG | CCGGAGAGAC | AGGTGCAACG | ACGCACCCAT | 540 |
| CCGTCCATCC | GCCCGCCCAA | CCAGGGCCAT | GCGGCCCAAC | TACCCGTCGT | CCCCGTCTAG | 600 |
| ACCACGCCCC | CCACCTGCCC | CGCCCCACCC | CACCCCCAAC | TCCTCCATGA | ATGCACGCAT | 660 |
| TTCATCGCTC | CAACCACAAC | GCAGCAGCCC | CAGCACCAGC | GGCCTCGGCG | ACGCGGCGCG | 720 |
| CATTTATACC | ACGCAATTCC | ATCTGGATCT | CCACCTGGCC | GCAGCACGGG | TTTCCTCCTC | 780 |
| CCTCCCCGCG | CGGCATTCCG | TCGAACGGCT | TGGCGGCGCG | CCTCCGGACG | GACCCACGGT | 840 |
| AAGCTCCCCC | TGCCCTTGCT | ATGCCCCTGC | TTCTGCACGC | ATCTTCCGAT | TTTCGCTGGA | 900 |
| GCGCTCCGCC | TCCGCCTATG | CGTGCGGGCG | ATTGACTGGG | CCGGACTTGC | CATGGACTCG | 960 |
| TACTGACCAG | TGATGTACTC | GCTCGCTAGC | CTCTCCGCCC | ACGCCGGCCT | CAAATCGAGC | 1020 |
| GCGCGTAGGC | TGCCTCCAGG | CCCCAATCCA | AGCAGCGCAG | CGCAGGGCCT | TCCTGCTGAT | 1080 |
| TCTCTCTCAG | CGCCAGGAGA | TCACGGGACC | AGATACCACT | GCTAGCAGTC | GACCCGTGCC | 1140 |
| GTCGCCGGAT | TGCCGGGTTC | GCCCCGTCTG | GCATTACGTC | GAGCGGGTGG | TGGGCGCGCG | 1200 |
| CGACTGGCCG | GGTTTTGGGC | ACACTTGTTG | CTTACTTCCT | TCTGCTGAAT | GCCGGAATTC | 1260 |
| AAGTCCATTT | CCCTCTTTGC | TCCTGCTTGG | ACTAACCAGT | CCCCTAGTGT | GGACTACAGC | 1320 |
| ATTTTTTTCG | CGTATTTTTA | ATGTGATCTC | TGGTCTTGCT | CTTCTGGTTC | TGCTGGTTGT | 1380 |
| TGACTAGAAT | TCTGCACTCT | CCCATGGCAC | TCTTGCCGGA | GGAATTTCCC | GATTTAGCTA | 1440 |
| GCCGTTAATT | AGTGCCACCA | TGTTGTTGTT | TTCTGTAGTA | CCATTTTAGC | ATCTGGTACA | 1500 |
| GAAAAAGGGC | ACACACATGC | CAAACCGAAA | AGAAATATCC | CAGTGCTGCA | ATTCTACGCT | 1560 |
| AATCGGACAT | AAATGATTGA | TGCGCTAACG | GACGGACTTG | TTCTTTTGCT | TTTCCCAGCG | 1620 |
| CTGAAGGTTG | GAGGGGGCAA | TAATG | | | | 1645 |

(2) INFORMATION FOR SEQ ID NO:2:

(i) SEQUENCE CHARACTERISTICS:
        (A) LENGTH: 2220 base pairs
        (B) TYPE: nucleic acid
        (C) STRANDEDNESS: single
        (D) TOPOLOGY: linear (xi) SEQUENCE DESCRIPTION: SEQ ID NO:2:

| | | | | | |
|---|---|---|---|---|---|
| CAAAAGCATG | ATATGCCCTT | GTGGCAAAAC | CGGTGACACG | GGAGTACAAC | ATGTTTCACC | 60 |
| ACCAACACGT | CACCCGAGAA | ACGGAATAAA | CACCCCGCAG | TATGTTTGAG | GCGTTGGCAT | 120 |

-continued

| | |
|---|---|
| CAAAAGCGTT GGGACCTATG CTAGGCACAA CATCCATCCG TGACGGCGAA GCGCAACTAT | 180 |
| TGTCTTCAAG GGGAAATGGA ATCGACTCCG CACCAACGGG AGCGGAGGGA GTCTACATCA | 240 |
| CACCCGTCAC GTGTCCCCGC CCCGTAAATG CACGACTAGA AGGTGCACCA TTGCATCCTC | 300 |
| AAAAAAGAAA AAAAAAAGCG AATCAACCTG TGGTTGGTTG GTTAGAGGGA CTGTGGTATC | 360 |
| CCCAGCCCAC CATGGTTCAA ATCCTGGTGC TCGCATTTAT TTCTGGATTT ATTTTAGGAT | 420 |
| TTCCGGCGAT GCGCATTCAG TGGGAGGTTC ATAGGGATGA GTGTATACGC GTGTATATGA | 480 |
| GCGCTTGCGT CTGTACTGTG TTAAAAAAAA AGAAAAAAAA AGATTATGTA CCATTGCGCG | 540 |
| TGTATGTCCA TACACTTGAG CCGATTAGCT AGAGAACAGG GTCATGATGC AGTCCGAGTT | 600 |
| ACGGTAACGA ACAAACGGGA GTCAACAAGG CGGCACAAGA CGCCGTGGTG GCTTGGCCGA | 660 |
| CGACTACGGG ACGGCCGGAC GGGTCGGGGA CGTGAGCGAA GCCGAAGGGA GCACGCCACC | 720 |
| GGAGCGGAAG GAGCGAGCAC ATCGAAGGCG TTGGGGCCCT ACCTACACAC ACGCCGGAGA | 780 |
| GACAGGTGCA ACGACACACC AATCCGTCCA ACCAGGGCGA TGAGGCCCAA CAACCTGTCG | 840 |
| TCGACTCCTC CCCGTCTCCA CCTCCACCAC ACCCCCCACC TGCCCCGCCC CACCCCACCC | 900 |
| CACCCCCAAC TCCTCCATGA ATGCACGCAT TTCATCGCTC CTACCACAAC GCAGCAGCAC | 960 |
| CAGCGGCCTC GGCGACGCGC CGCGCATTTA TAGCAAGCAA TTCCCCGTTG CCTCCGCCTC | 1020 |
| CGCCGCCGCT GCCTCTCCTG GATCTCCATC TGGCCGCAGC ACGGCCTTCT TCCTCCTTCC | 1080 |
| TCCCTCCGCG GCATTCCGTC GAACGGCTTC GCGGCGCGGC TCCGGCCGAA CCGACGGTAC | 1140 |
| GCGCCCTGCC CGTCCCCCCT GCCCCCGCCG TGCCCCTGCT TCTGCCCCCA TCTTCCGGTT | 1200 |
| TTCGCTGGAG CACCGCGTGC GTGTGTGTAG GTGATTGAGC GAGTCGGTCT CGCTACTGGC | 1260 |
| TTCGGCCCGA GCTGCCGTGT CCCGGCGCGC GCGCGTAGGA GCAGTAGTAC TACCACCAGC | 1320 |
| TTCTCCGTCC CCGGGGCCTT CAAATCGAGC ACGAGCCGGC TAGCTCCAGG CCCCCCAGTC | 1380 |
| CCGCGCCGCG CAAGCGGCGC GGGGCCTTCC TGCTGGTTCT AGCGGCACGA GATCACGGAG | 1440 |
| CGGGATACTG CTCTCGCGCG CGCGATTCGA GCTAGTTCGT GCGCGCGGAG TCCTGCTGAC | 1500 |
| GCGGATCCT GCCGACGATC GACCCGCGCC GTCGCCGAAT TGGCGGGCGG CTTCTTCGTG | 1560 |
| CCGTCTGGCA TTACGTCGAA CGGGTGGTGG GCGTGCGTGA TTGGCCGGGT TTTGGGTGCT | 1620 |
| TGCTGCTTCC GTCCTTGTGC TGAATGTCGG AATTCAAGTC CCTTTTCCCC TTCGCTCCTG | 1680 |
| CTTGGAGTGG ACTAACCTTA GTGTGGACTT CAACATTTTT TTCATGTGAT CTAGGGTCTT | 1740 |
| GCTGTTCTGT TTCTGCTGGC TGTTGACTAT CAGCTTACTG TTGCGGATTG CGCACTTTCC | 1800 |
| CCTGGCACTG TTTCCGGAGG AATTTCCTGA TTTTTTTAGT TATTAGTGGT TAAATAGTAC | 1860 |
| CATTATGTCT TTGTTTGCTT TGTGCCATTT TTAGCATCCA GTACAGAAAA AAAGGAATAA | 1920 |
| ACGTGCAAAA CTGAAAAATA ATAACCCGGT GCTGTTTCGC TAACCAGACA GAATTGATTC | 1980 |
| CACCATTTTC CTGATTTAGT TAGTAGTTAA ATAGGACTAC TATGTTTTTG TTCTGTTTGT | 2040 |
| ACCATTTTAG CATCTAGTAC AGAAAAAGCG CACACACATG CCAAACCGAA AAGAAATATC | 2100 |
| CCAATGCTGC AATTCTACGC TAATCGGACA TAAATGATTG ATGCGCTAAC AGACGGATTT | 2160 |
| GTTCTTTTGC TTTTCCCAGT GCTGAAGGTT GGAGGGGGCA ATAATGGTGG AATCTGACCA | 2220 |

(2) INFORMATION FOR SEQ ID NO:3:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (xi) SEQUENCE DESCRIPTION: SEQ ID NO:3:

```
TTCCGGCCGA ACCGACGGTA CGCGCTAGCC TCTCCGCCCA CGCCGGCCTC AAATCGACCG    60
CGGTTCCGCT GCCCCCAGGC CCCAATCCGA GCAGCGCAGC GCAGGGCCTC CCTGCTGATT   120
CTAAGCGGCA CGGAACCAGA TACCACCGCT TTCCCGTGCG CGCGCGCGGC GTGAGATTCC   180
GAGTGCTCCA GCTAGTTCCT ACACGCGGAG CGGACGCGAG GCGAGATCCT GCTAGCAGTC   240
GACCCGTGCC GTCGCCGGAT TGGCGGGTTC GCGCCGTCTG GCATTACGTC GAGCGGGTGG   300
TGGGCGTGCG CGACTGGCCG GGTTTTGGGT ATACTTGTTG CTTACTTCCT TGTGCTGAAT   360
GTCGGAATTC AAGTCCAGTT CCCTCTTTAC TTCCTTGTGC TGGCCTGCTT CAACGTTTTT   420
TCACGTATTT TTAACGTGAT CTGTTGTGTG GTCTTGCTGG CTGTTGACTA TCAGCTCACT   480
GCTGCTAATT GTGCACTTTC CCGTGGCACT GTTGCTGGAG GAATTTCCCG ATTTAGGTAG   540
TCGTTAATTA GTGCCACCAT GTTGTTGTTT TCTGTACCAT TTAGCATCT GGTACAGAAA    600
AAGGGCACAC ACATGCCAAA CCGAAAAGAA ACATCCCAGT GCTGCAATTC TACGCTAATC   660
GGGCATAAAT GATTGATGCG CTAACAGACG GACTTGTTCT TTTGCTTTTC CCAGTGCTGC   720
AATTCTACGC TAATCGGACA TAAATGATTG ATGCGCTAAC AGACAGACTT GTTCTTTTGC   780
TTTTCCCAGT GCTGAAGGTC GGAGGGGGCA ATAATGGTGG AATCTGACCA GATAAACGGG   840
ACGCCCAACA GGATGTCCTC GGTCGAAGAG TTCTGTAAAG CGCTCGGGGG CGACTCGCCG   900
ATACACAGCG TGCTGGTTGC CAACAATGGG ATGGCTGCGG TCAAGTTCAT GCGCAGCATC   960
CGCACCTGGG CCTTGGAGAC CTTTGGGAAC GAGAAGGCCA TTCTCTTGGT GGCTATGGCA  1020
ACTCCA                                                            1026
```

(2) INFORMATION FOR SEQ ID NO:4:

(i) SEQUENCE CHARACTERISTICS:
        (A) LENGTH: 1778 base pairs
        (B) TYPE: nucleic acid
        (C) STRANDEDNESS: single
        (D) TOPOLOGY: linear (xi) SEQUENCE DESCRIPTION: SEQ ID NO:4:

```
CAAAAGCATG ATATGCCCTT GTGGCGCAAC CAGTGACACG AGAGCACACC ACGTTTGATC    60
CCCAACACAT CGCACGGAAA TTTGGAAGAA AAAAGCCACC CCCCGCAGCT ACGATTCGAA   120
GATGTCGGCA TCAAAGCCGT TTGGACCTGT GCGAGACAAC AGCATCCATC CATGACGGCG   180
AAGCGCAACT ATTTTCTTCA AGGGGAAATG GAATCGACTC CGCACGCCAT CCGGGACGGG   240
AGCACGCCAC CGGATGAGCG GAGCGAGCGA GCACATCCAA GGCGTTGGGG CCCTACCTAC   300
CCAAGGCAGA CACGCCGGAG AGACAGGTGC AACGACACAC CAATCCATCC GCCCAAGCAA   360
GCAAGCAGGG CCATGAGGAC CAACTACCCG TCGTCCCCGT CTAGACCACA CCCCCCACCT   420
GCCCCCACCC TCCCTCCCCC AACTCCTCCA TGAATGCACG CATTTCATCA TCGCCCCAAC   480
CACAACGCAG CAGCAGCGGC CTCGGCGACG CGCCGCGCAT TTATAGCACG CAATTCCTCG   540
TTGCCTCCGC CGCCGCCGCC TGCCTGCCTC TCCTGGATCT CCATCTCTCC TTCGCGGCGC   600
GGCATTCCGT CGAACGCCTC CGCGGCGCGC CTCCGGGCGG ACTCACGGTA AGCTCCCCCT   660
GCCCTTGCTG TGCCCCTGCT TCTGCTCGCA TCTTCCGATT TTCGCCGGAG CGCTCCGCCT   720
CCGCCTATAT GCGTGCGGGC GATTGACTGG GCCGGACCTG CCATGGACTC GTGCTTGACC   780
CGCCCGTGCC CCAGTGCGCG CGGGGAGGAC CAGTGATGTA CTCGCTCCCA GCCTCCCCGC   840
CCACGCCGGC CTCAAATCGA GCGCGCGTAG GCTGCCTCCA GGCCCCAATC CGAGTAGCGC   900
```

-continued

| | |
|---|---|
| AGCGCGGGGC CTTCCTGCTG ATTCTCTCTC AGCGCCAGGA GATCACGGCA CCAGATACCA | 960 |
| CTGCTTCTGC GTGCGCGCGC GCGGCGTCAG ATTCCGAGTG CTTCCACCTA GTCCGTACAC | 1020 |
| GCGGAGCTGC CGCGGGATCC TGCTGACAGT CGACCCGTGC CGTCGCCGGA TTGGCGGGTT | 1080 |
| CGTGCCGTCT GGCATTACGT CGAGCGGGTT GTGGGCGCGC GCGACCGGCC GGGTTTTGGG | 1140 |
| CACACTTGTT GCTTGCTTCC TTCTCCTGAA TGCCGGAATT CAAGTCCATT TCCCTCTTTG | 1200 |
| CTCCTGCTTG GAGTGGAGTA ACCCCTAGTG TGGACTTCAA CATTGTTTCA CGTATTTTTA | 1260 |
| ATGTCATCTG TGGTCTTGCT CTTCTGCTTC TGCTGGTTTG TCGACTATGA GCTTACTGTC | 1320 |
| GTGAATTGTG CACTTTCCCG TGGCACTGCT GCCCTAGGAA TTTCCGGATT TAGTTAGTCG | 1380 |
| TTAATTAGTG CCACCATGCT GTTGTTTTGT CTGTACCATT TTAGCATCTG GTACAGAAAA | 1440 |
| AGGGCACACA CATGCCAAAC CGAAAAGAAA TATCCCAGTG CTGCAATTCT ACGCTAATCA | 1500 |
| CCCATAAATG ATTGATGCGC TAACGGACGG ACTTGTTCTT TTGCTTTTCC CAGTGCTGAA | 1560 |
| GGTTGGAGGG GGCAATAATG GTGGAATCTG ACCAGATAAA CGGGAGGATG TCCTCGGTCG | 1620 |
| ACGAGTTCTG TAAAGCGCTC GGGGGCGACT CGCCGATACA CAGCGTGCTG GTTGCCAACA | 1680 |
| ATGGGATGGC TGCGGTCAAG TTCATGCGCA GCATCCGCAC CTGGGCCTTG GAGACCTTTG | 1740 |
| GGAACGAGAA GGCCATTCTC TTGGTGGCTA TGGCAACT | 1778 |

(2) INFORMATION FOR SEQ ID NO:5:

(i) SEQUENCE CHARACTERISTICS:
        (A) LENGTH: 1157 base pairs
        (B) TYPE: nucleic acid
        (C) STRANDEDNESS: single
        (D) TOPOLOGY: linear (xi) SEQUENCE DESCRIPTION: SEQ ID NO:5:

| | |
|---|---|
| TGGCGGCGCG CCTCCGGACG GACCCACGGT AAGCTCCCCC TGCCCTTGCT GTGCCCCTGC | 60 |
| TTCTGCTCGC ATCTTCCGAT TTTCGCCGGA GCGCTCCGCC TCCGCCTATA TGCGTGCGGG | 120 |
| CGATTGACTG GGCCGGACCT GCCATGGACT CGTGCTTGAC CCGCCCGTGC CCCAGTGCGC | 180 |
| GCGGGGAGGA CCAGTGATGT ACTCGCTCCC AGCCTCCCCG CCCACGCCGG CCTCAAATCG | 240 |
| AGCGCGCGTA GGCTGCCTCC AGGCCCCAAT CCGAGTAGCG CAGCGCGGGG CCTTCCTGCT | 300 |
| GATTCTCTCT CAGCGCCAGG AGATCACGGC ACCAGATACC ACTGCTTCTG CGTGCGCGCG | 360 |
| CGCGGCGTCA GATTCCGAGT GCTTCCACCT AGTCCGTACA CGCGGAGCTG CCGCGGGATC | 420 |
| CTGCTGACAG TCGACCCGTG CCGTCGCCGG ATTGGCGGGT TCGTGCCGTC TGGCATTACG | 480 |
| TCGAGCGGGT TGTGGGCGCG CGCGACCGGC CGGGTTTTGG GCACACTTGT TGCTTACTTC | 540 |
| CTTCTGCTGA ATGCCGGAAT TCAAGTCCAT TTCCCTCTTT GCTCCTGCTT GGACTAACCA | 600 |
| GTCCCCTAGT GTGGACTACA GCATTTTTTT CGCGTATTTT TAATGTGATC TCTGGTCTTG | 660 |
| CTCTTCTGGT TCTGCTGGTT GTTGACTAGA ATTCTGCACT CTCCCATGGC ACTCTTGCCG | 720 |
| GAGGAATTTC CCGATTTAGC TAGCCGTTAA TTAGTGCCAC CATGTTGTTG TTTTCTGTAG | 780 |
| TACCATTTTA GCATCTGGTA CAGAAAAAGG GCACACACAT GCCAAACCGA AAGAAATAT | 840 |
| CCCAGTGCTG CAATTCTACG CTAATCGGAC ATAAATGATT GATGCGCTAA CGGACGGACT | 900 |
| TGTTCTTTTG CTTTTCCCAG CGCTGAAGGT TGGAGGGGGC AATAATGGTG GAATCTGACC | 960 |
| AAATAAACGG GACGCCCAAC AGGATGTCCT CGGTCGATGA ATTCTGTAAA GCGCTCGGGG | 1020 |
| GTGACTCGCC GATACACAGC GTGCTGGTTG CCAACAATGG GATGGCTGCG GTCAAATTCA | 1080 |
| TGCGCAGCAT CCGCACCTGG GCCTTGGAGA CCTTTGGGAA CGAGAAGGCC ATTCTCTTGG | 1140 |

TGGCTATGGC AACTCCA                                                           1157

(2) INFORMATION FOR SEQ ID NO:6:

(i) SEQUENCE CHARACTERISTICS:
        (A) LENGTH: 6993 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(911, 1043)
        (D) OTHER INFORMATION: /note= "Y = C or T"

(ix) FEATURE:
        (A) NAME/KEY: modified_base
        (B) LOCATION: 986
        (D) OTHER INFORMATION: /note= "M = A or C"

(ix) FEATURE:
        (A) NAME/KEY: modified_base
        (B) LOCATION: one-of(1796, 1797)
        (D) OTHER INFORMATION: /note= "W = A or T"

(xi) SEQUENCE DESCRIPTION: SEQ ID NO:6:

GAACACTGCA TCTGCGCTGT TTGTCCAAAG GGAGGACGAT GGGATCCACA CATTTGCCCA        60

TTGTCGGCCT TAATGCCTCG ACAACACCAT CGCTATCCAC TATTCGCCCG GTAAATTCAG       120

CCGGTGCTGC ATTCCAACCA TCTGCCCCTT CTAGAACCTC CAAGAAGAAA AGTCGTCGTG       180

TTCAGTCATT AAGGGATGGA GGCGATGGAG GCGTGTCAGA CCCTAACCAG TCTATTCGCC       240

AAGGTCTTGC CGGCATCATT GACCTCCCAA AGGAGGGCAC ATCAGCTCCG GAAGTGGATA       300

TTTCACATGG GTCCGAAGAA CCCAGGGGCT CCTACCAAAT GAATGGGATA CTGAATGAAG       360

CACATAATGG GAGGCATGCT TCGCTGTCTA AGGTTGTCGA ATTTTGTATG GCATTGGGCG       420

GCAAAACACC AATTCACAGT GTATTAGTTG CGAACAATGG AATGGCAGCA GCTAAGTTCA       480

TGCGGAGTGT CCGAACATGG GCTAATGAAA CATTTGGGTC AGAGAAGGCA ATTCAGTTGA       540

TAGCTATGGC TACTCCAGAA GACATGAGGA TAAATGCAGA GCACATTAGA ATTGCTGATC       600

AATTTGTTGA AGTACCCGGT GGAACAAACA ATAACAACTA TGCAAATGTC CAACTCATAG       660

TGGAGATAGC AGTGAGAACC GGTGTTTCTG CTGTTTGGCC TGGTTGGGGC CATGCATCTG       720

AGAATCCTGA ACTTCCAGAT GCACTAAATG CAAACGGAAT TGTTTTTCTT GGGCCACCAT       780

CATCATCAAT GAACGCACTA GGTGACAAGG TTGGTTCAGC TCTCATTGCT CAAGCAGCAG       840

GGGTTCCGAC TCTTCCTTGG AGTGGATCAC AGGTGGAAAT TCCATTAGAA GTTTGTTTGG       900

ACTCGATACC YGCGGAGATG TATAGGAAAG CTTGTGTTAG TACTACGGAG GAAGCACTTG       960

CGAGTTGTCA GATGATTGGG TATCCMGCCA TGATTAAAGC ATCATGGGGT GGTGGTGGTA      1020

AAGGGATCCG AAAGGTTAAT AAYGACGATG ATGTCAGAGC ACTGTTTAAG CAAGTGCAAG      1080

GTGAAGTTCC TGGCTCCCCA ATATTTATCA TGAGACTTGC ATCTCAGAGT CGACATCTTG      1140

AAGTTCAGTT GCTTTGTGAT CAATATGGCA ATGTAGCTGC GCTTCACAGT CGTGACTGCA      1200

GTGTGCAACG GCGACACCAA AAGATTATTG AGGAAGGACC AGTTACTGTT GCTCCTCGCG      1260

AGACAGTGAA AGAGCTAGAG CAAGCAGCAA GGAGGCTTGC TAAGGCTGTG GGTTATGTTG      1320

GTGCTGCTAC TGTTGAATAT CTCTACAGCA TGGAGACTGG TGAATACTAT TTTCTGGAAC      1380

TTAATCCACG GTTGCAGGTT GAGCATCCAG TCACCGAGTG GATAGCTGAA GTAAACTTGC      1440

CTGCAGCTCA AGTTGCAGTT GGAATGGGTA TACCCCTTTG GCAGGTTCCA GAGATCAGAC      1500

GTTTCTATGG AATGGACAAT GGAGGAGGCT ATGACATTTG GAGGAAAACA GCAGCTCTTG      1560

```
CTACTCCATT TAACTTCGAT GAAGTGGATT CTCAATGGCC AAAGGGTCAT TGTGTAGCAG   1620

TTAGGATAAC CAGTGAGGAT CCAGATGACG GATTCAAGCC TACCGGTGGA AAAGTAAAGG   1680

AGATCAGTTT TAAAAGCAAG CCAAATGTTT GGGCCTATTT CTCTGTTAAG TCCGGTGGAG   1740

GCATTCATGA ATTTGCTGAT TCTCAGTTTG GACATGTTTT TGCATATGGA GTGTCWWGAG   1800

CAGCAGCAAT AACCAACATG TCTCTTGCGC TAAAAGAGAT TCAAATTCGT GGAGAAATTC   1860

ATTCAAATGT TGATTACACA GTTGATCTCT TGAATGCCTC AGACTTCAAA GAAAACAGGA   1920

TTCATACTGG CTGGCTGGAT AACAGAATAG CAATGCGAGT CCAAGCTGAG AGACCTCCGT   1980

GGTATATTTC AGTGGTTGGA GGAGCTCTAT ATAAAACAAT AACGAGCAAC ACAGACACTG   2040

TTTCTGAATA TGTTAGCTAT CTCGTCAAGG GTCAGATTCC ACCGAAGCAT ATATCCCTTG   2100

TCCATTCAAC TGTTTCTTTG AATATAGAGG AAAGCAAATA TACAATTGAA ACTATAAGGA   2160

GCGGACAGGG TAGCTACAGA TTGCGAATGA ATGGATCAGT TATTGAAGCA AATGTCCAAA   2220

CATTATGTGA TGGTGGACTT TTAATGCAGT TGGATGGAAA CAGCCATGTA ATTTATGCTG   2280

AAGAAGAGGC CGGTGGTACA CGGCTTCTAA TTGATGGAAA GACATGCTTG TTACAGAATG   2340

ATCACGATCC TTCAAGGTTA TTAGCTGAGA CACCCTGCAA ACTTCTTCGT TTCTTGGTTG   2400

CCGATGGTGC TCATGTTGAA GCTGATGTAC CATATGCGGA AGTTGAGGTT ATGAAGATGT   2460

GCATGCCCCT CTTGTCACCT GCTGCTGGTG TCATTAATGT TTTGTTGTCT GAGGGCCAGC   2520

CTATGCAGGC TGGTGATCTT ATAGCAAGAC TTGATCTTGA TGACCCTTCT GCTGTGAAGA   2580

GAGCTGAGCC ATTTAACGGA TCTTTCCCAG AAATGAGCCT TCCTATTGCT GCTTCTGGCC   2640

AAGTTCACAA AAGATGTGCC ACAAGCTTGA ATGCTGCTCG GATGGTCCTT GCAGGATATG   2700

ATCACCCGAT CAACAAAGTT GTACAAGATC TGGTATCCTG TCTAGATGCT CCTGAGCTTC   2760

CTTTCCTACA ATGGGAAGAG CTTATGTCTG TTTTAGCAAC TAGACTTCCA AGGCTTCTTA   2820

AGAGCGAGTT GGAGGGTAAA TACAGTGAAT ATAAGTTAAA TGTTGGCCAT GGGAAGAGCA   2880

AGGATTTCCC TTCCAAGATG CTAAGAGAGA TAATCGAGGA AAATCTTGCA CATGGTTCTG   2940

AGAAGGAAAT TGCTACAAAT GAGAGGCTTG TTGAGCCTCT TATGAGCCTA CTGAAGTCAT   3000

ATGAGGGTGG CAGAGAAAGC CATGCACACT TTATTGTGAA GTCCCTTTTC GAGGACTATC   3060

TCTCGGTTGA GGAACTATTC AGTGATGGCA TTCAGTCTGA TGTGATTGAA CGCCTGCGCC   3120

AACAACATAG TAAAGATCTC CAGAAGGTTG TAGACATTGT GTTGTCTCAC CAGGGTGTGA   3180

GAAACAAAAC TAAGCTGATA CTAACACTCA TGGAGAAACT GGTCTATCCA AACCCTGCTG   3240

TCTACAAGGA TCAGTTGACT CGCTTTTCCT CCCTCAATCA CAAAAGATAT TATAAGTTGG   3300

CCCTTAAAGC TAGCGAGCTT CTTGAACAAA CCAAGCTTAG TGAGCTCCGC ACAAGCATTG   3360

CAAGGAGCCT TTCAGAACTT GAGATGTTTA CTGAAGAAAG GACGGCCATT AGTGAGATCA   3420

TGGGAGATTT AGTGACTGCC CCACTGCCAG TTGAAGATGC ACTGGTTTCT TTGTTTGATT   3480

GTAGTGATCA AACTCTTCAG CAGAGGGTGA TCGAGACGTA CATATCTCGA TTATACCAGC   3540

CTCATCTTGT CAAGGATAGT ATCCAGCTGA AATATCAGGA ATCGGTGTT ATTGCTTTAT   3600

GGGAATTCGC TGAAGCGCAT TCAGAGAAGA GATTGGGTGC TATGGTTATT GTGAAGTCGT   3660

TAGAATCTGT ATCAGCAGCA ATTGGAGCTG CACTAAAGGG TACATCACGC TATGCAAGCT   3720

CTGAGGGTAA CATAATGCAT ATTGCTTTAT TGGGTGCTGA TAATCAAATG CATGGAACTG   3780

AAGACAGTGG TGATAACGAT CAAGCTCAAG TCAGGATAGA CAAACTTTCT GCGACACTGG   3840

AACAAAATAC TGTCACAGCT GATCTCCGTG CTGCTGGTGT GAAGGTTATT AGTTGCATTG   3900
```

-continued

| | | | | |
|---|---|---|---|---|
| TTCAAAGGGA | TGGAGCACTC | ATGCCTATGC | GCCATACCTT | CCTCTTGTCG | GATGAAAAGC | 3960 |
| TTTGTTATGA | GGAAGAGCCG | GTTCTCCGGC | ATGTGGAGCC | TCCTCTTTCT | GCTCTTCTTG | 4020 |
| AGTTGGGTAA | GTTGAAAGTG | AAAGGATACA | ATGAGGTGAA | GTATACACCG | TCACGTGATC | 4080 |
| GTCAGTGGAA | CATATACACA | CTTAGAAATA | CAGAGAACCC | CAAAATGTTG | CACAGGGTGT | 4140 |
| TTTTCCGAAC | TCTTGTCAGG | CAACCCGGTG | CTTCCAACAA | ATTCACATCA | GGCAACATCA | 4200 |
| GTGATGTTGA | AGTGGGAGGA | GCTGAGGAAT | CTCTTTCATT | TACATCGAGC | AGCATATTAA | 4260 |
| GATCGCTGAT | GACTGCTATA | GAAGAGTTGG | AGCTTCACGC | GATTAGGACA | GGTCACTCTC | 4320 |
| ATATGTTTTT | GTGCATATTG | AAAGAGCAAA | AGCTTCTTGA | TCTTGTTCCC | GTTTCAGGGA | 4380 |
| ACAAAGTTGT | GGATATTGGC | CAAGATGAAG | CTACTGCATG | CTTGCTTCTG | AAAGAAATGG | 4440 |
| CTCTACAGAT | ACATGAACTT | GTGGGTGCAA | GGATGCATCA | TCTTTCTGTA | TGCCAATGGG | 4500 |
| AGGTGAAACT | TAAGTTGGAC | AGCGATGGGC | CTGCCAGTGG | TACCTGGAGA | GTTGTAACAA | 4560 |
| CCAATGTTAC | TAGTCACACC | TGCACTGTGG | ATATCTACCG | TGAGGTCGAA | GATACAGAAT | 4620 |
| CACAGAAACT | AGTGTACCAC | TCTGCTCCAT | CGTCATCTGG | TCCTTTGCAT | GGCGTTGCAC | 4680 |
| TGAATACTCC | ATATCAGCCT | TTGAGTGTTA | TTGATCTGAA | ACGTTGCTCC | GCTAGAAATA | 4740 |
| ACAGAACTAC | ATACTGCTAT | GATTTTCCGT | TGGCATTTGA | AACTGCAGTG | CAGAAGTCAT | 4800 |
| GGTCTAACAT | TTCTAGTGAC | ACTAACCGAT | GTTATGTTAA | AGCGACGGAG | CTGGTGTTTG | 4860 |
| CTCACAAGAA | CGGGTCATGG | GGCACTCCTG | TAATTCCTAT | GGAGCGTCCT | GCTGGGCTCA | 4920 |
| ATGACATTGG | TATGGTAGCT | TGGATCTTGG | ACATGTCCAC | TCCTGAATAT | CCCAATGGCA | 4980 |
| GGCAGATTGT | TGTCATCGCA | AATGATATTA | CTTTTAGAGC | TGGATCGTTT | GGTCCAAGGG | 5040 |
| AAGATGCATT | TTTTGAAACT | GTTACCAACC | TAGCTTGTGA | GAGGAAGCTT | CCTCTCATCT | 5100 |
| ACTTGGCAGC | AAACTCTGGT | GCTCGGATCG | GCATAGCAGA | TGAAGTAAAA | TCTTGCTTCC | 5160 |
| GTGTTGGATG | GTCTGATGAT | GGCAGCCCTG | AACGTGGGTT | TCAATATATT | TATCTGACTG | 5220 |
| AAGAAGACCA | TGCTCGTATT | AGCGCTTCTG | TTATAGCGCA | CAAGATGCAG | CTTGATAATG | 5280 |
| GTGAAATTAG | GTGGGTTATT | GATTCTGTTG | TAGGGAAGGA | GGATGGGCTA | GGTGTGGAGA | 5340 |
| ACATACATGG | AAGTGCTGCT | ATTGCCAGTG | CCTATTCTAG | GGCCTATGAG | GAGACATTTA | 5400 |
| CGCTTACATT | TGTGACTGGA | AGGACTGTTG | GAATAGGAGC | ATATCTTGCT | CGACTTGGCA | 5460 |
| TACGGTGCAT | TCAGCGTACT | GACCAGCCCA | TTATCCTAAC | TGGGTTTTCT | GCCTTGAACA | 5520 |
| AGCTTCTTGG | CCGGGAAGTG | TACAGCTCCC | ACATGCAGTT | GGGTGGCCCC | AAAATTATGG | 5580 |
| CGACAAACGG | TGTTGTCCAT | CTGACAGTTT | CAGATGACCT | TGAAGGTGTA | TCTAATATAT | 5640 |
| TGAGGTGGCT | CAGCTATGTT | CCTGCCAACA | TTGGTGGACC | TCTTCCTATT | ACAAAATCTT | 5700 |
| TGGACCCACC | TGACAGACCC | GTTGCTTACA | TCCCTGAGAA | TACATGCGAT | CCTCGTGCTG | 5760 |
| CCATCAGTGG | CATTGATGAT | AGCCAAGGGA | AATGGTTGGG | GGGCATGTTC | GACAAAGACA | 5820 |
| GTTTTGTGGA | GACATTTGAA | GGATGGGCGA | AGTCAGTTGT | TACTGGCAGA | GCGAAACTCG | 5880 |
| GAGGGATTCC | GGTGGGTGTT | ATAGCTGTGG | AGACACAGAC | TATGATGCAG | CTCATCCCTG | 5940 |
| CTGATCCAGG | CCAGCTTGAT | TCCCATGAGC | GATCTGTTCC | TCGTGCTGGG | CAAGTCTGGT | 6000 |
| TTCCAGATTC | AGCTACTAAG | ACAGCGCAGG | CAATGCTGGA | CTTCAACCGT | GAAGGATTAC | 6060 |
| CTCTGTTCAT | CCTTGCTAAC | TGGAGAGGCT | TCTCTGGTGG | ACAAAGAGAT | CTTTTTGAAG | 6120 |
| GAATCCTTCA | GGCTGGGTCA | ACAATTGTTG | AGAACCTTAG | GACATACAAT | CAGCCTGCCT | 6180 |
| TTGTATATAT | CCCCAAGGCT | GCAGAGCTAC | GTGGAGGGGC | TTGGGTCGTG | ATTGATAGCA | 6240 |
| AGATAAATCC | AGATCGCATT | GAGTTCTATG | CTGAGAGGAC | TGCAAAGGGC | AATGTTCTCG | 6300 |

| | | | | |
|---|---|---|---|---|
| AACCTCAAGG | GTTGATCGAG | ATCAAGTTCA | GGTCAGAGGA | ACTCCAAGAG TGCATGGGTA | 6360 |
| GGCTTGATCC | AGAATTGATA | AATCTGAAGG | CAAAGCTCCA | GGGAGTAAAG CATGAAAATG | 6420 |
| GAAGTCTACC | TGAGTCAGAA | TCCCTTCAGA | AGAGCATAGA | AGCCCGGAAG AAACAGTTGT | 6480 |
| TGCCTTTGTA | TACTCAAATT | GCGGTACGGT | TCGCTGAATT | GCATGACACT TCCCTTAGAA | 6540 |
| TGGCTGCTAA | GGGTGTGATT | AAGAAGGTTG | TAGACTGGGA | AGATTCTAGG TCGTTCTTCT | 6600 |
| ACAAGAGATT | ACGGAGGAGG | ATATCCGAGG | ATGTTCTTGC | GAAGGAAATT AGAGGTGTAA | 6660 |
| GTGGCAAGCA | GTTTTCTCAC | CAATCGGCAA | TCGAGCTGAT | CCAGAAATGG TACTTGGCCT | 6720 |
| CTAAGGGAGC | TGAAACAGGA | AGCACTGAAT | GGGATGATGA | CGATGCTTTT GTTGCCTGGA | 6780 |
| GGGAAAACCC | TGAAAACTAC | CAGGAGTATA | TCAAAGAACT | CAGGGCTCAA AGGGTATCTC | 6840 |
| AGTTGCTCTC | AGATGTTGCA | GACTCCAGTC | CAGATCTAGA | AGCCTTGCCA CAGGGTCTTT | 6900 |
| CTATGCTATT | AGAGAAGATG | GATCCCTCAA | GGAGAGCACA | GTTTGTTGAG GAAGTCAAGA | 6960 |
| AAGTCCTTAA | ATGATCAGAT | GATACCGTCG | ACG | | 6993 |

(2) INFORMATION FOR SEQ ID NO:7:

(i) SEQUENCE CHARACTERISTICS:
        (A) LENGTH: 9361 base pairs
        (B) TYPE: nucleic acid
        (C) STRANDEDNESS: single
        (D) TOPOLOGY: linear (xi) SEQUENCE DESCRIPTION: SEQ ID NO:7:

| | | | | | |
|---|---|---|---|---|---|
| GATCTCGTTA | TCAATGACAT | CCAATGTCCA | TAGTCAGGAA | ACCATGACTA TCTGTTGATC | 60 |
| AACGAGCTAG | TCAACTAGAG | GCTTACTAGG | GACATGTTGG | TGTCTATGAA TTCACACATG | 120 |
| TATTACGATT | TCCGGATAAC | ACAATTATAG | CATGAATAAA | AGACAATTAT CATGAACAAG | 180 |
| GAAATATAAT | AATAATGCTT | TTATTATTGC | CTCTAGGGCA | TATTTCCAAC ATGCACCGTG | 240 |
| TCCGTAGTGT | CTCTCGCTTC | CTTGTCATCG | ACTCATGGGA | CACCCGGTAC CCGGGAGCGC | 300 |
| CCCACCATCT | TCTGCACGCA | TCCGCACACT | TCTCCTTTGC | ACCGGTATCT CAATCGAGTT | 360 |
| ACCGGAACCG | GAACATTGCC | GTGGCACCGT | TTTCGTTATC | GTTGTCGTGG CACCCCTTTT | 420 |
| CTTTCCACCA | CGGTGACAAA | TGCTTCATAA | TGCTCTTGTC | AACTTTTAAT AAAAATTGCA | 480 |
| TAAATTTGCA | CATGTCATCC | GCATCATGAT | AAAAACAATT | AAAATGTTTA AAATTGTTGT | 540 |
| TTGCATTAAA | TTGCTAAATG | CACATGAGGA | TTTACCGGAA | TTGTTGTTTG ATGTTTTCGG | 600 |
| CCTCATTTAA | AATGCCTAAC | TGTGTATTTT | ACTTATGCTT | CACCTCTTGC CATGCTAACC | 660 |
| AACATTTAAT | ATTGTTGAGT | ACATAAACGG | GAGAGAACTA | AATAAGTCAT GTGGTGTTCC | 720 |
| ATCAATATGC | AACTCGTTGC | ATATTGAGCT | CCACTTAATT | TGTAGTTTTG CTTGTTGCAC | 780 |
| TTTGCCATGC | CATGCATATT | TAAACCGGAC | ATGCATCATC | TTTGATTGTG CATCATGCCA | 840 |
| TGTTTATGCT | TGTTGGTTTA | CCATGTTGTT | TTCTTCTTTC | CGGTGTTGTT TCTTCGGATT | 900 |
| AGTTCCGATA | ACATCGCGTT | CGTGGGGATT | CGTTCGACTA | CGTTCGTTTG TTTCTTCTTC | 960 |
| ATGGACTCAT | TCTTCTTCCT | TGCGGGATCT | CAGGCAAGAT | GACCATATCC TCGAAATCAC | 1020 |
| TTCTATCTTT | GCTTGCTAGT | TGCTCGCTCT | ATTGCTATGC | TGCGATACCT ACCACTTGCT | 1080 |
| TTATCATGCC | TCCCATATTG | CCATGTCAAG | CCTCTAACCC | ACCCTTCCTA GCAAACCGTT | 1140 |
| GTTTGGCTAT | GTTACCGCTT | TGCTCAGCCC | CTCTTATAGC | ATTGCTAGTT GCAGGCGAAG | 1200 |
| ACGAAGTTTG | TTCCATGTTT | GAAACATGGA | TATGTTGGGA TATCACAATA TCTCTTATTT | | 1260 |
| ATATTAATGC | ATCTATATAC | TTGGTAAAGG | GTGGAAGGCT | CGGCCTTATG CCTGGTGTTT | 1320 |

```
TGTTCCACTC TTGCCGCCCT AGTTTCCGTC ATACCAGTGT TATGTTCCTT GATTTTGCGT    1380

TCCTTACACG GTTGGGTGTT ATGGGAACCC CTTGATAGTT CGCTTTGAAT AAAACTCCTC    1440

CAGCAAGGCC CAACCTTGGT TTTACATTTG CCTTACCTAG CCTTTTTCCC TTGGGTTTCC    1500

AGAGCCCGAG GGTCATCTTT ATTTTAACCC CCCCGGGCCA GTGCTTCTCT AAGTGTTGGT    1560

CCAACCTGAG CGATGTCCGG CGCCCCCTGG GCAACCAGGG TCTATGCCAA CCCGATGTCT    1620

GGCTCATCCG GTGTGCCCTG AGAATGAGAT ATGTGCAGCT CCTATCGGGA TTTGTCGGCA    1680

CATCGGACGG CTTTGCTGGT CTTGTTTTAC CATTGTTGAA ATGTCTTGTA ACCGGGATTC    1740

CGAGTCTGAT CGGGTTTTCC TGGGAGAAGG AATATCCTTT GTTGACCGTG AGAGCTTGTG    1800

ATGGGCTAAG TTGGGACACC CCTGCAGGGT TTTGAACTTT TGAAAGCCGT GCCCGCGGTT    1860

ATGGGCAGAT GGGGATTTGT TAATATCCGG TTGTAGAAAA CATGACACTT AACTTAATTT    1920

AAAATGCATC AACCGCGTGT GTAGCCGTGA CGGTCTCTTT CCGGCGGAGT CCGGGAAGTG    1980

AACACGGTTC TTGTGTTATG CTTCAACGTA AGTAGTTTCA GGATCACTTC TTGACCACTT    2040

TTAGTTCCTC GCCCGTGCTT TGCTTCTCTT ATCGCTCTCA TTTGCGTAAG TTAGCCACCA    2100

TATATGCTAG TGCTTGCTGC AGCTCCACCT CACTACCTCT TACCTACCCA TAAGCTTAAA    2160

TAGTCTTGAT CTCGCGGGTG TGAGATTGCT GAGTCCCCAT GACTCACAGA TTACTTCCAA    2220

AACCAGTTGC AGGTGCCGTT GATACCAGTG CAGATGACGC AGCTGAGCTC AAGTGGGAGC    2280

TCGATGAAGA CCATGTTTGT TGTGTTGTTT CGTTTCTTTT CGTTCAGTAG TGGAGCCCAG    2340

TTGGGGCGAT CGGGGATCTA GCATGAGGGG TGGTCTTCTT TTATTTTGGT TCCGTAGTCG    2400

GACCTTGATT GTATTCTGAA TGATGTAATG CTATATTTAT GTATTGTGTG AAGTGGCGAT    2460

TGTAAGCCAA CTCTGTATCC CTTTGTTATT CAGTACATGA GATGTGTAAA GATTATCCCT    2520

CTTGCGACAT GCCTACCATG TAGTTATGCC TCTAAGTCAT GCTCCGACAC GTGGATGTTA    2580

CAACATCCCT CACACCGTAT GTTCAAACTC AAGCAGGAAG TATCCATGTC GTCCTATGGG    2640

GGTCACGAGC TAGAACTAAC CGAACCGTTC GTAAAGCCCC ATGGTTGTCC TCGCGTGCTT    2700

GCCCTACCTC CCTCACACAG ACACTGGGCG AGGCGAAGTC CCTAAAGAAA CTGATACATG    2760

CACTATTTTT TGTAACATGG TAGTAATCAC GCCTTTAAAA CGAGCACAAC AGATGAAGTT    2820

AGGAGGTTGA TTTGCGTTCA ATAATGTAAC CGTGTATCAT ACTGTACAAA GTTTCAAAAT    2880

CCAAATTAAA TGTCGAGAAT CATTATTAGG TGAGCTTAGA CCTACAGAAT AGAACATGAA    2940

CGCATGTATT CCGATGACAA AGGAGGAGGA ACCAAGTGAG TTCACCCTAA CCTAATCATG    3000

GCGACAACCA ACATCCATTA AAGTGGCGAG AGGAGGTTCA TGCCCAGATT TCGGGTATTC    3060

GGGGGAAAGA AACGGTTGTG CCCCTCATGT TGGAGCAACG ATGACGTTGC TTCTGTGCTA    3120

GGTGCAAGGC AACGCCGTTT GCCAGCACAT TGGAAGTAAA CATAGGGTTA TGAGGAAAGG    3180

GGCGAGGGAA ATTGGATTGA GACAAGGAAG GGTGCTGGCA TGATCAAGAG ACGATGTGAT    3240

CATTGTGAAG GAGGTACTGT GGCCCACACG TCGGCATACA ATTGCGATGG GATAAGGCGG    3300

GTGCAGAGTA TGCACCATGA AAGATCACAT ACAATCGCCT ACCCCCTTCA ACAAGATGAC    3360

CGAACACCAC CGACGAGTTA AAACCAAAGA TACACGGGAC CTGCCAAAAA AAGGGTTCAA    3420

GCGCGTACAT TAACAAAACC GTTTATGGCT CCCAATCAAA ACCTAGGAAT CATGTACTTA    3480

TATATTTTAC ATAAGCACGA TAGGACGATG TCGAACGGAC GCCACAATCG CCAACCATGA    3540

TCGAACACCA CCCAAAGCCA CGAGCGCAGA GCAACGAAAA GTCGACGTGT TCCCCGAAAT    3600

TACGCGTGCC CATAAACAGA ACCTCCCGAC ATCGTCGACG ACGACGACGA CCAGCTCCAA    3660
```

```
CAACAGAAAC GGCACACGCG TTTCACACAC TGTTTTCTCC GGTGGCGACG ACGTTGCGCA    3720
TGGCAGGAAG GAATGTCACG ATCGCCCAAC CACTAAACCT TAATCCAACA ACGACACTGT    3780
TCTAATCCAC CTATGACGTT CTCCCCCTAC GGCCGCCTGC CACCGTCCTC CAAACCGGGA    3840
CACGCCAAGA CGCGCCGCGA GAGAGCGAGC GACCACGACC CATCACAATC ACAATCACAA    3900
GGAGAGAAAA ATCAAAACCC AAACCCCACG GCCAGCGCGG CGGGCAGGGG GCAGCGTGGG    3960
AGCCGTCGGA TGGGCGGATC GGGGCCGTCC GCTTGGCGGG GCGATGGGCG TCACGTGCGG    4020
GGGCGCCAGG GGGAGGCGGA GTCCCCGAAG AGGGCCGGGA ATTTATTATT TTAGGCCGCA    4080
CAGCCCCCAT CTCCGTCCCT CTCCCCTCAC CCCCTCGGGA TATCCGCCCG CGCTCCACTC    4140
TCCCCCCGTC TCCGGCACCG TGCGCGCCGC CGCCGCCGCT AAGATCCAGC CCCTCGTCCG    4200
CTCCGCCACG CGCCAGCGCC CAGCACGCGT CGGCCCGTCC GCCCCGCCG CCCCCGAGGT    4260
GCGCCTCTAT TTATCTCTTT CCCCCCTCGC GTCTCCCCCC ATTCCCCCTG TCGCTTCCCC    4320
CCAGGTCAGG TCAGGTCAGG CCAGGCCAGA TCCGCCGCCC GATCCGCCTC CGCTCCCGGA    4380
GGTGAGCCCG GCCGCCTTGG TCCGCCGTTG CTCTGTTTCC CGCGCGCTGA GCTGGGGCAC    4440
TGCTTAGGGT GCTTCGTCCG TGGGTGGCGG GGAGAGGGTT TAAGGGTTCT GCCCCGCGCG    4500
GGACTTACTG TACTAGGTGT TTGAAATTAC GCGGAGCTTG GGATTGGGTT CTTCGGAGCT    4560
TGCGCTGGCA TGCTTCGTGT TCATGAGTGC TCATGGAGGG AGTAATTATG GAATGTGGCT    4620
CCCGTACTGT ATGCACAGTA GACAATTATC GGTGATTATG GCTGGTGTGG CTCGTTGGAG    4680
GTGCCCTGCG CGTGCCTAAC ACTGTATTTC TTAGGTTAGG ACGGTGTGCT TCCATGGACA    4740
CATGCTCATG CTGAGTGCAA GCTCACCCAG GGTGGTTGCA CAACGACACG GTCATACATG    4800
GGTAGCGCGG TCCAGTGTTG TAGTCAGTTT GCCGCCGTAC GCATGCGAGG CAGGTGTTGT    4860
TTCTGCCGTG TTGATGCTAC CGGCTGTCAT AATGCACTTT GAGTGTTAGT ATTGAGCTGG    4920
AAATGGTAGA TGCTGTTTTT TCCCTTCTCT CCCCCTCTCA CCTGTTGATC TAGCTGCTGT    4980
AATACTTTAC CTGCCATCTT TTCTTTTTTG GCTGCATGTA TTAGCTGTGA AGCTTAGAA    5040
TCATTTGCCT TGTACTTTTT GTACGAACCT GTGTCATAGG AGTAATTGCA CACGTTATCT    5100
GTTTTGGTCA AGAGCATCTT GGATGTTCAA ACTTACAGAG GAAGGTCATG AATTAGCCCA    5160
TAAAGTACTT GTGTCTTGTC TCTGTGAACT AACAATTTGT ATTCACATGC ATCTGTCAGG    5220
TTCCAAGACC TGGGGTTTAC ACACCTTTGA TGGCACTGTC TCTTTGAAGA ACACTGCATC    5280
TGCGCTGTTT GTCCAAAGGG AGGACGATGG GATCCACACA TTTGCCCATC GTCGGCTTTA    5340
ATGCCTCAAC AACACCATCG CTATCCACTA TTCGCCCGGT AAATTCAGCT GGTGCTGCAT    5400
TCCAACCATC TGCCCCTTCT AGAACCTCCA AGAAGAAAAG TCGTCGTGTT CAGTCATTAA    5460
GGGATGGAGG CGATGGAGGC GTGTCAGACC CTAACCAGTC TATTCGCCAT GGTAACAACC    5520
TGAAAACCAT TTCCTTTCTA CAAACTACAC TTTGTTGTCA TCCTCAGACT TGTGTAGATA    5580
CTTTTATTGA CTGAGAGCAT GTTGGTTTTA GTGTAAGGTA TCTCAATGCT AGATCACAGA    5640
ATGGCGGTTA TTGACCTCGT TAAAGATGCA AATGACTGCA GCAATATTTA ACAATTTTTT    5700
TATGTGATAC GATAGTACTT TTTTATAACG AGTAATGAGT AAAGCCCAGT TTTTCTTGAT    5760
TAAATGGTTT TAGTGGAAGG AATGTTTAAT ATTCAAAATG ATGTTTTATA AGGGAAGGAA    5820
CATGAAAGTG CAAGAATACT TTTTTATAAC GAGTAATGAG TAAAGCCCAG TTTTTCTTGA    5880
TTAAATGGTT TTAGTGGAAG GAATGTTTAA TATTCAAAAT GATGTTTTAT AAGGGAAGGA    5940
ACATGAAAGT GCAAGAATAC ATATAAGCAG CATATTAGTT ATGTATGACT GAGTCATTTT    6000
CCTTATATAA TACTTCTAAA AGAGAAGAAT GTCTAGAAAC CTTTTCTGAT AATTTACTAG    6060
```

```
CATGAAGAAC AATAACATTC ATAAAGTTGT CACCTGTGCT TCTTCTTAGC TATCGTGTAA    6120

ACTTGCTCAG TTTCTAATGC ATATCTGGAT GTAGGTCTTG CCGGCATCAT TGACCTCCCA    6180

AAGGAGGGCA CATCAGCTCC GGAAGTGGAT ATTTCACAGT AAGTACTTTA GCATTTAAA    6240

ATTAGAATTA GCATCTCTCT TTAAAATGGA AAAATATCTA TAATTTAATA TAGAATTATT    6300

ATAGATTATG CTTATTTTAT TATTCGCACA TGCTGATATT TTGAATTGCA TTTGATATAT    6360

TTTTATAGAT TTTTACTGAA CTACTCCCTC CGTAAACTAA TATAAGAGCG TTTAGAACAC    6420

TATTTTAGTG ATCTAAACAC TCTTATATTG GTTTACAGAG GGAGTACATT ATAGTTGCCA    6480

TACACAATGC ATTTGCTCAG GCACATCACT GTTGCACTGC ATGGAGTATT TTTGTGCACT    6540

TAGGAATCAT TTTCAGAAAG CCTTTTGCCT ATAATTTTAA AAATAATAAT TTAATTACCA    6600

TCTGAAACCC GTACCCACAT GACGGATGAA AGCTCATTTG AAGTTTTCGA TTTATAGTAG    6660

CCAAGTATTT GTTATGTTAT ATTGTTATGG TCACCATCGT AATGAATTTG TTCTTTTTTC    6720

TCTAGTGGGT CCGAAGAACC CAGGGGCTCC TACCAAATGA ATGGGATACT GAATGAAGCA    6780

CATAATGGGA GGCATGCTTC GCTGTCTAAG GTTGTTGAAT TTTGTATGGC ATTGGGCGGC    6840

AAAACACCAA TTCACAGTGT ATTAGTTGCG AACAATGGAA TGGCAGCAGC TAAGTTCATG    6900

CGGAGTGTCC GAACATGGGC TAATGAAACA TTTGGGTCAG AGAAGGCAAT TCAGTTGATA    6960

GCTATGGCTA CTCCAGAAGA CATGAGGATA AATGCAGAGC ACATTAGAAT TGCTGATCAA    7020

TTTGTTGAAG TACCCGGTGG AACAAACAAT AACAACTATG CAAATGTCCA ACTCATAGTG    7080

GAGGTTAGTA TTGCTCATCC GTTGATGTGC AACCGATGCA CAAGTTGTTC ATTTAGCATG    7140

ACATGACAAT TTTGCTGTTG CAGATAGCAG TGAGAACCGG TGTTTCTGCT GTTTGGCCTG    7200

GTTGGGGCCA TGCATCTGAG AATCCTGAAC TTCCAGATGC ACTAAATGCA AACGGAATTG    7260

TTTTTCTTGG GCCACCATCA TCATCAATGA ACGCACTAGG TGACAAGGTT GGTTCAGCTC    7320

TCATTGCTCA AGCAGCAGGG GTTCCGACTC TTCCTTGGAG TGGATCACAG GTGAATCTCA    7380

CATTCTCTGA TAACTCATCG TCTGATCTTT GTACTGGACA CATTTAAAAA CCGAAAGACA    7440

CTATATTATA GGTGGAAATT CCATTAGAAG TTTGTTTGGA CTCGATACCT GCGGAGATGT    7500

ATAGGAAAGC TTGTGTTAGT ACTACAGAGG AAGCACTTGC GAGTTGTCAG ATGATTGGGT    7560

ATCCCGCCAT GATTAAAGCA TCATGGGGTG GTGGTGGTAA AGGGATCCGA AAGGTACATC    7620

ATTCATTTGA TTGGACTATA TTTGAAAGAT TGTGTGGGTT GTTGTGTGAT ATATTATGCC    7680

CAGAGTTAGC TCTAACCTTT TCAACATATT AACTCAATAT CTGTTGCAGG TTAATAATGA    7740

CGATGATGTC AGAGCACTGT TTAAGCAAGT GCAAGGTGAA GTTCCTGGCT CCCCAATATT    7800

TATCATGAGA CTTGCATCTC AGGTTAGACT TCTCAGCAAG TTGCATTTTT TCCAAGCATG    7860

TTATTCCCGA GTTGTATATT ACACGCCTGG AAGCTTCATA TGTTATTCCT TGCAGGCTAG    7920

AAATGTATGC TGGAACATGT GCTCATATGG TATATTATGT TTTAATCCTC CCCTTTTTTC    7980

TTTTGTAGAG TCGACATCTT GAAGTTCAGT TGCTTTGTGA TCAATATGGC AATGTAGCTG    8040

CGCTTCACAG TCGTGACTGC AGTGTGCAAC GGCGACACCA AAAGGTAACG CTGGTCCAGA    8100

TCTGAAAACA TCACGTGTAT TGCATGTTCT ACTTCATACT TGTAGTTGTT TATCAAAAGG    8160

ACCAATTGCG TCCATTTTTT GTTTATACCA GATTATTGAG GAAGGACCAG TTACTGTTGC    8220

TCCTCGCGAG ACAGTGAAAG AGCTAGAGCA AGCAGCAAGG AGGCTTGCTA AGGCTGTGGG    8280

TTATGTTGGT GCTGCTACTG TTGAATATCT CTACAGCATG GAGACTGGTG AATACTATTT    8340

TCTGGAACTT AATCCACGGT TGCAGGTATA TTCTTTTGAA CATTCCTCTG GACTTAGTTT    8400
```

```
TTTGTCGTCA GTTATTTACA TTGTTAAATG GCATACATCC AGGTTGAGCA TCCAGTCACC      8460

GAGTGGATAG CTGAAGTAAA CTTGCCTGCA GCTCAAGTTG CAGTTGGAAT GGGTATACCC      8520

CTTTGGCAGG TTCCAGGTAA TAATTATATT ATTGTAAGTT TTTTAGTTAC TTTCCCATGT      8580

TACTTCTGTG CCTAACTTTC TCCTTATACA GAGATCAGAC GTTTCTATGG AATGGACAAT      8640

GGAGGAGGCT ATGACATTTG GAGGACAACA GCAGCTCTTG CTACTCCATT TAACTTCGAT      8700

GAAGTGGATT CTCAATGGCC AAAGGGTCAT TGTGTAGCAG TTAGGATAAC CAGTGAGGAT      8760

CCAGATGACG GATTCAAGCC TACCGGTGGA AAAGTAAAGG TGAGATTTCA TGATGCCGTC      8820

TATGGTTCTA GCACATTAGA TTTGTAAACT GACCGGACCT TGATTTTCTT ATAATTCAGG      8880

AGATCAGTTT TAAAAGCAAG CCAAATGTTT GGGCCTATTT CTCTGTTAAG GTAAGCTGTT      8940

CATGGCTCTG TTGCACTGTT ATATTGTTGA GTTGGGCTTT GACCAAGTAT TAACCAAATC      9000

GAACACATTT TTGTTCCCCC TTTTATCTGT TTTCAGTCCG GTGGAGGCAT TCATGAATTT      9060

GCTGATTCTC AGTTTGGTAT GCAAAATTTG ACCCTGTGAA TATTCCTCTT TGCTATTTGT      9120

ATTGGTCCTT ACGTTTGGAA GATTACTCTT TTCATTTCAG GACATGTTTT TGCATATGGA      9180

GTGTCTAGAG CAGCAGCAAT AACCAACATG TCTCTTGCGC TAAAAGAGAT TCAAATTCGT      9240

GGAGAAATTC ATTCAAATGT TGATTACACA GTTGATCTCT TGAATGTAAG AAATACTACC      9300

TGTATATTGA ATCCCTGCTT TTGATGTAAT ACAACCATTT TACATCTGGC ATTCCTTTAA      9360

A                                                                      9361

(2) INFORMATION FOR SEQ ID NO:8:

(i) SEQUENCE CHARACTERISTICS:
        (A) LENGTH: 5058 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 175
        (D) OTHER INFORMATION: /note= "Y = C or T"

(xi) SEQUENCE DESCRIPTION: SEQ ID NO:8:

GATCCAGCCC CTCGTCCGCT CCGCCACGCG CCAGCGCCCA GCACGCGTCG GCCCGTCCGC        60

CCCCGCCGCC CCCGCCCGAG GTGCGCCTCT ATTTATCTCT TTCCCCCCTC GCGTCTCCCC       120

CCATTCCCCC TGTCGCTTCC CCCCATGTCA GGCCAGATCC GCCGCCCGAT CCGCYTCAGC       180

TCCCGGAGGT GAGCCCGGCC GCCCGCCGCC TTCCTCCGCC GTTGCTCTGT TTCCAGCGGG       240

CCCAGCTGTG GCACTGCGTA GGGTGCTTCG TTCGTGGGTG GCGGGGAGAG GGTTTAAGGG       300

TTCTGCGCCT GCGCTGCTCT GCTCCGCCCG GGACTTACTG TACTAGGTGT TTGAAATTAT       360

GCGGAGCTTG GAATTGGGAT CTTCGGAGCT TGCGCTGGCA TGCTCCGTGT TCGTAAGTGC       420

TCATGGAGGG AGTAATTATG GAATGTGGCT CCCGCACTGT ATGCACAGTA GTCAATTATC       480

GGTAATTATG GCTGGTGTGG CTCGCCGGAG CTGCCCTGTG CGTGCCTGCC ACTGTATTTT       540

GTAGGTTGGG TCGGTGTGCT TCCATGGACA CATGCTCATG CTAAGTGCAA GCTGACCCAG       600

GGTGGTTGCA CAACGACACG GTGATACAGG GGTAGCGGTC CACTGTTGTA GCCAGTTTGC       660

CGCCGTACGC ATGCCTTTTC TGCCGTTCAG TCTCCACTTC TTTGGGTGAG GGAGTCGCGT       720

ATCGTTTCGG TCGTGTTGAT GCTACCTGCT GTCATAATGC ACTGTGAGCA GTAGTATTGC       780

ACTGGGAATG GTAGTTGCTG TTTTTTCCCC CTCTCTCTCT AACCTGGTGA TCTAGCCACC       840

CTATTACTTT GCCTGCCATC TTCTCTTTTT GGCTGCATGT GTTAGTTGTG AAAGCGTAGA       900
```

-continued

```
ATCATTTGCG TTGGTACTTG TTTTACGTAC CTGTGTCATA GGAGTAATTG CACACGTTAT    960

CTGTTTTGGT CAAGAGCATC TTGGATGTTC AAACTTGCAG AGGAAGGTCA TGAATTAGCC   1020

CATAAAGTAC TTGTGTCTTG TCTCTATGGA CTAATAATTT GTATTCACAT GCTTCTGTCA   1080

GGTTTCAAAA CCCGGGGTTT ACACACCTTT GATGGCACTG TCTCTTTGAA GAACACTGCA   1140

TCTGCGCTGT TTGTCCAAAG GGAGGACGAT GGGATCCACA CATTTGCCCA TTGTCGGCCT   1200

TAATGCCTCG ACAACACCAT CGCTATCCAC TATTCGCCCG GTAAATTCAG CCGGTGCTGC   1260

ATTCCAACCA TCTGCCCCTT CTAGAACCTC AAGAAGAAA AGTCGTCGTG TTCAGTCATT    1320

AAGGGATGGA GGCGATGGAG GCGTGTCAGA CCCTAACCAG TCTATTCGCC AAGGTAAACT   1380

GAAAACCATT TCCTTCCTAC AAACTACACT TTGTTGTCAT CCTCAAACTT GTGTAGATAC   1440

TTTTATTGAC TGAGAGCATG CTGGTGTTAG TGTAAGATAT CTCAATGCTA GATCACAGAA   1500

TGGCGGTTAT TGACCTTGTT AAAGATGCAA ATGACTGCAG CAATATTTAA CACTTTTTTA   1560

TGCGATACAA ATACAATAGT AGTTCTTCTA TATAATGAGT AATGAGTAAA GCCCAGTTTT   1620

TCTTGATTAA ATGGTTTTAG TGGAAGGAAT GTTTAATGTT CAAATGATG GTTTATAAGG    1680

GAAAGGAACA TGAAAGTGCA AGAATACATA TAAGCAGCAT ATTAGTTATG CAAGACTGAA   1740

TCATTTTCCT TATATAATAC TTCTAAAAGA GAAGGATGTC TAGAAACCTT TTCTGATAAT   1800

TTACTAGCAT GAAGAACAAT AACATTCGTA AATTGACACC TGTGCTTCTT CTTAGCTATC   1860

GTGTTGCTCA GTTTCTAATG CATATCTGGA TGTAGGTCTT GCCGGCATCA TTGACCTCCC   1920

AAAGGAGGGC ACATCAGCTC CGGAAGTGGA TATTTCACAG TAAGTACTTG AGCATTTTAA   1980

AATTAGAATT AGCATATCTC TCTTTAAAAA GGAAAAATAT GTATAGTTTA ATATAGAATT   2040

ATTATAGATT ATGCTTATTT TATTATTCGC ATATGCTGAT ATTTTGAATT GCATTTGATA   2100

TATTTTTATA GATTTTTACT GAACTACATT ATAGTTGCCA TACACAATGC ATTTGCTCAG   2160

GCACATCACT GTTGCACTGC ATGGAGTATT TTTGTGCACT TAGGAATCAT TTTCAGAAAG   2220

CCTTTTGCCT ATAATTTTAA AAATAATAAT TTAATTACCA TCTGAAACCC GTACCCGCAT   2280

GACGGATGAA AGCTCATTTG AAGTTTTCGA TTTATAGTAG CCAAGTGTTT GTTATGTTAT   2340

ATTGTTATGG TCACCATCGT AATGATTTTG TTCTTTTTTC TCTAGTGGGT CCGAAGAACC   2400

CAGGGGCTCC TACCAAATGA ATGGGATACT GAATGAAGCA CATAATGGGA GGCATGCTTC   2460

GCTGTCTAAG GTTGTCGAAT TTTGTATGGC ATTGGGCGGC AAAACACCAA TTCACAGTGT   2520

ATTAGTTGCG AACAATGGAA TGGCAGCAGC TAAGTTCATG CGGAGTGTCC GAACATGGGC   2580

TAATGAAACA TTTGGGTCAG AGAAGGCAAT TCAGTTGATA GCTATGGCTA CTCCAGAAGA   2640

CATGAGGATA AATGCAGAGC ACATTAGAAT TGCTGATCAA TTTGTTGAAG TACCCGGTGG   2700

AACAAACAAT AACAACTATG CAAATGTCCA ACTCATAGTG GAGGTTAGTA TTGCTCACCC   2760

GTTGATGTGC AATTGATGCG CAAGTTGTTC ATTTAGCATG ACATGACAAT TTTGCTGTTG   2820

CAGATAGCAG TGAGAACCGG TGTTTCTGCT GTTTGGCCTG GTTGGGGCCA TGCATCTGAG   2880

AATCCTGAAC TTCAGATGCA ACTAAATGCA AACGGAATTG TTTTTCTTGG GCCACCATCA   2940

TCATCAATGA ACGCACTAGG TGACAAGGTT GGTTCAGCTC TCATTGCTCA AGCAGCAGGG   3000

GTTCCGACTC TTCCTTGGAG TGGATCACAG GTGAATCTCA CATTCTCTGA TAACTCATCG   3060

TCTGATCTTT GTACTGGACA CATTTTATAA CAGAAAGACA CTATATTATA GGTGGAAATT   3120

CCATTAGAAG TTTGTTTGGA CTCGATACCT GCGGAGATGT ATAGGAAAGC TTGTGTTAGT   3180

ACTACGGAGG AAGCACTTGC GAGTTGTCAG ATGATTGGGT ATCCAGCCAT GATTAAAGCA   3240
```

```
TCATGGGGTG GTGGTGGTAA AGGGATCCGA AAGGTACATC ATTCATTTGA TTGGACTATA    3300

TTCAAAAGAT TGTGTGGGTT GTTGTGTGAT ATTTTATGCC CAGAGTTAGC TCTAACCTTT    3360

TCAACATATT AACTCAATAT CTGTTGCAGG TTAATAACGA CGATGATGTC AGAGCACTGT    3420

TTAAGCAAGT GCAAGGTGAA GTTCCTGGCT CCCCAATATT TATCATGAGA CTTGCATCTC    3480

AGGTTAGACT TCTCTGCAAG TTGCATTTTT TCCAAGCATG TTGTTCCCGA GTTGTATATT    3540

ATACGCCTGG AAGCTTCATA TGTTATTCCT TGCAGGCTAG AAATGTATGC TGGAACATGT    3600

GCTCATATGG TATATTATGT TTTAATCCTC CCCTTTTTTC TTTTGTAGAG TCGACATCTT    3660

GAAGTTCAGT TGCTTTGTGA TCAATATGGC AATGTAGCTG CGCTTCACAG TCGTGACTGC    3720

AGTGTGCAAC GGCGACACCA AAAGGTAACG CTGGTCCAGA TCTGAAAACA TCACGTGTAT    3780

TACATGTTCT ACTTCATACT TGTAGTTGTT TATCAAAAGG ACCAATTGCG TCCATTTTTT    3840

GTTTATACCA GATTATTGAG GAAGGACCAG TTACTGTTGC TCCTCGCGAG ACAGTGAAAG    3900

AGCTAGAGCA AGCAGCAAGG AGGCTTGCTA AGGCTGTGGG TTATGTTGGT GCTGCTACTG    3960

TTGAATATCT CTACAGCATG GAGACTGGTG AATACTATTT TCTGGAACTT AATCCACGGT    4020

TGCAGGTATA TTCTTTTGAA CATTCCTCTG GACTTAGTTT TTTGTCGTCA GTTATTTACA    4080

TTGTTAAATG GCATACATCC AGGTTGAGCA TCCAGTCACC GAGTGGATAG CTGAAGTAAA    4140

CTTGCCTGCA GCTCAAGTTG CAGTTGGAAT GGGTATACCC CTTTGGCAGG TTCCAGGTAA    4200

TAATTATATT ATTGTAAGTT TTTTAGTTAC TTTCCCATGT TATTTCTGTG CCTAACTTTC    4260

TCCTTATACA GAGATCAGAC GTTTCTATGG AATGGACAAT GGAGGAGGCT ATGACATTTG    4320

GAGGAAAACA GCAGCTCTTG CTACCCCATT TAACTTTGAT GAAGTGGATT CTCAATGGCC    4380

AAAGGGTCAT TGTGTAGCAG TTAGGATAAC CAGTGAGGAT CCAGATGACG GATTCAAGCC    4440

TACCGGTGGA AAAGTAAAGG TGAGATTTCA TGATGCCGTC TATGGTTCTA GCACATTAGA    4500

TTTGTAAACT GACCGGATCT TGATTTTCTT ATAATTCAGG AGATCAGTTT TAAAAGCAAG    4560

CCAAATGTTT GGGCCTATTT CTCTGTTAAG GTAAGCTGTT CATGGCTCTG TTGCACTGTT    4620

ATATTGTTGA GTTGGGCAGA AAATTGGGCT GCGTTTTTTT TGAACTATTT TTTCCATTTG    4680

GGCTTTGACC AAGTACTAAC CAAATCGAAC ACATTTTTGT CCCCCCTTTT ATCTGTTTTC    4740

AGTCCGGTGG AGGCATTCAT GAATTTGCTG ATTCTCAGTT TGGTATGCAA AATTTGACCC    4800

TGTGTATATT CCTCTTTGCT ATTTGTATTG GTCCTTACGT TTGGAAGATT ACTCTTTTCA    4860

TTACAGGACA TGTTTTTGCA TATGGAGTGT CTAGAGCAGC AGCAATAACC AACATGTCTC    4920

TTGCGCTAAA AGAGATTCAA ATTCGTGGAG AAATTCATTC AAATGTTGAT TACACAGTTG    4980

ATCTCTTGAA TGTAAGAAAT ACCTCCTGTA TATGCTTTTG ATGTAATACA ACCATTTTAC    5040

ATCTGGCATT CCTTTAAA                                                  5058
```

(2) INFORMATION FOR SEQ ID NO:9:

(i) SEQUENCE CHARACTERISTICS:
        (A) LENGTH: 2311 amino acids
        (B) TYPE: amino acid
        (C) STRANDEDNESS:
        (D) TOPOLOGY: linear (ix) FEATURE:
        (A) NAME/KEY: Modified-site
        (B) LOCATION: one-of(291, 316, 335, 586, 587)
        (D) OTHER INFORMATION: /note= "Xaa = Any Amino Acid"

(xi) SEQUENCE DESCRIPTION: SEQ ID NO:9:

Met Gly Ser Thr His Leu Pro Ile Val Gly Leu Asn Ala Ser Thr Thr

-continued

```
1               5                   10                  15

Pro Ser Leu Ser Thr Ile Arg Pro Val Asn Ser Ala Gly Ala Ala Phe
                20                  25              30

Gln Pro Ser Ala Pro Ser Arg Thr Ser Lys Lys Ser Arg Arg Val
            35                  40              45

Gln Ser Leu Arg Asp Gly Gly Asp Gly Val Ser Asp Pro Asn Gln
        50                  55              60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90              95

Gly Ser Tyr Gln Met Asn Gly Ile Leu Asn Glu Ala His Asn Gly Arg
                100                 105             110

His Ala Ser Leu Ser Lys Val Val Glu Phe Cys Met Ala Leu Gly Gly
            115                 120             125

Lys Thr Pro Ile His Ser Val Leu Val Ala Asn Asn Gly Met Ala Ala
    130                 135             140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170             175

Arg Ile Asn Ala Glu His Ile Arg Ile Ala Asp Gln Phe Val Glu Val
            180                 185             190

Pro Gly Gly Thr Asn Asn Asn Tyr Ala Asn Val Gln Leu Ile Val
        195                 200             205

Glu Ile Ala Val Arg Thr Gly Val Ser Ala Val Trp Pro Gly Trp Gly
    210                 215             220

His Ala Ser Glu Asn Pro Glu Leu Pro Asp Ala Leu Asn Ala Asn Gly
225                 230             235                 240

Ile Val Phe Leu Gly Pro Pro Ser Ser Met Asn Ala Leu Gly Asp
                245                 250             255

Lys Val Gly Ser Ala Leu Ile Ala Gln Ala Ala Gly Val Pro Thr Leu
            260                 265             270

Pro Trp Ser Gly Ser Gln Val Glu Ile Pro Leu Glu Val Cys Leu Asp
        275                 280             285

Ser Ile Xaa Ala Glu Met Tyr Arg Lys Ala Cys Val Ser Thr Thr Glu
    290                 295             300

Glu Ala Leu Ala Ser Cys Gln Met Ile Gly Tyr Xaa Ala Met Ile Lys
305                 310                 315                 320

Ala Ser Trp Gly Gly Gly Lys Gly Ile Arg Lys Val Asn Xaa Asp
                325                 330             335

Asp Asp Val Arg Ala Leu Phe Lys Gln Val Gln Gly Glu Val Pro Gly
            340                 345             350

Ser Pro Ile Phe Ile Met Arg Leu Ala Ser Gln Ser Arg His Leu Glu
        355                 360             365

Val Gln Leu Leu Cys Asp Gln Tyr Gly Asn Val Ala Ala Leu His Ser
    370                 375             380

Arg Asp Cys Ser Val Gln Arg His Gln Lys Ile Ile Glu Glu Gly
385                 390             395                 400

Pro Val Thr Val Ala Pro Arg Glu Thr Val Lys Glu Leu Glu Gln Ala
                405                 410             415

Ala Arg Arg Leu Ala Lys Ala Val Gly Tyr Val Gly Ala Ala Thr Val
            420                 425             430
```

-continued

```
Glu Tyr Leu Tyr Ser Met Glu Thr Gly Glu Tyr Tyr Phe Leu Glu Leu
            435                 440                 445
Asn Pro Arg Leu Gln Val Glu His Pro Val Thr Glu Trp Ile Ala Glu
        450                 455                 460
Val Asn Leu Pro Ala Ala Gln Val Ala Val Gly Met Gly Ile Pro Leu
465                 470                 475                 480
Trp Gln Val Pro Glu Ile Arg Arg Phe Tyr Gly Met Asp Asn Gly Gly
                485                 490                 495
Gly Tyr Asp Ile Trp Arg Lys Thr Ala Ala Leu Ala Thr Pro Phe Asn
            500                 505                 510
Phe Asp Glu Val Asp Ser Gln Trp Pro Lys Gly His Cys Val Ala Val
        515                 520                 525
Arg Ile Thr Ser Glu Asp Pro Asp Gly Phe Lys Pro Thr Gly Gly
530                 535                 540
Lys Val Lys Glu Ile Ser Phe Lys Ser Lys Pro Asn Val Trp Ala Tyr
545                 550                 555                 560
Phe Ser Val Lys Ser Gly Gly Ile His Glu Phe Ala Asp Ser Gln
                565                 570                 575
Phe Gly His Val Phe Ala Tyr Gly Val Xaa Xaa Ala Ala Ala Ile Thr
            580                 585                 590
Asn Met Ser Leu Ala Leu Lys Glu Ile Gln Ile Arg Gly Glu Ile His
            595                 600                 605
Ser Asn Val Asp Tyr Thr Val Asp Leu Leu Asn Ala Ser Asp Phe Lys
        610                 615                 620
Glu Asn Arg Ile His Thr Gly Trp Leu Asp Asn Arg Ile Ala Met Arg
625                 630                 635                 640
Val Gln Ala Glu Arg Pro Pro Trp Tyr Ile Ser Val Val Gly Gly Ala
                645                 650                 655
Leu Tyr Lys Thr Ile Thr Ser Asn Thr Asp Thr Val Ser Glu Tyr Val
            660                 665                 670
Ser Tyr Leu Val Lys Gly Gln Ile Pro Pro Lys His Ile Ser Leu Val
        675                 680                 685
His Ser Thr Val Ser Leu Asn Ile Glu Glu Ser Lys Tyr Thr Ile Glu
        690                 695                 700
Thr Ile Arg Ser Gly Gln Gly Ser Tyr Arg Leu Arg Met Asn Gly Ser
705                 710                 715                 720
Val Ile Glu Ala Asn Val Gln Thr Leu Cys Asp Gly Gly Leu Leu Met
                725                 730                 735
Gln Leu Asp Gly Asn Ser His Val Ile Tyr Ala Glu Glu Ala Gly
            740                 745                 750
Gly Thr Arg Leu Leu Ile Asp Gly Lys Thr Cys Leu Leu Gln Asn Asp
            755                 760                 765
His Asp Pro Ser Arg Leu Leu Ala Glu Thr Pro Cys Lys Leu Leu Arg
        770                 775                 780
Phe Leu Val Ala Asp Gly Ala His Val Glu Ala Asp Val Pro Tyr Ala
785                 790                 795                 800
Glu Val Glu Val Met Lys Met Cys Met Pro Leu Leu Ser Pro Ala Ala
                805                 810                 815
Gly Val Ile Asn Val Leu Leu Ser Glu Gly Gln Pro Met Gln Ala Gly
            820                 825                 830
Asp Leu Ile Ala Arg Leu Asp Leu Asp Asp Pro Ser Ala Val Lys Arg
            835                 840                 845
```

-continued

```
Ala Glu Pro Phe Asn Gly Ser Phe Pro Glu Met Ser Leu Pro Ile Ala
    850                 855                 860
Ala Ser Gly Gln Val His Lys Arg Cys Ala Thr Ser Leu Asn Ala Ala
865                 870                 875                 880
Arg Met Val Leu Ala Gly Tyr Asp His Pro Ile Asn Lys Val Val Gln
                    885                 890                 895
Asp Leu Val Ser Cys Leu Asp Ala Pro Glu Leu Pro Phe Leu Gln Trp
                900                 905                 910
Glu Glu Leu Met Ser Val Leu Ala Thr Arg Leu Pro Arg Leu Leu Lys
            915                 920                 925
Ser Glu Leu Glu Gly Lys Tyr Ser Glu Tyr Lys Leu Asn Val Gly His
        930                 935                 940
Gly Lys Ser Lys Asp Phe Pro Ser Lys Met Leu Arg Glu Ile Ile Glu
945                 950                 955                 960
Glu Asn Leu Ala His Gly Ser Glu Lys Glu Ile Ala Thr Asn Glu Arg
                965                 970                 975
Leu Val Glu Pro Leu Met Ser Leu Leu Lys Ser Tyr Glu Gly Gly Arg
                980                 985                 990
Glu Ser His Ala His Phe Ile Val Lys Ser Leu Phe Glu Asp Tyr Leu
            995                 1000                1005
Ser Val Glu Glu Leu Phe Ser Asp Gly Ile Gln Ser Asp Val Ile Glu
        1010                1015                1020
Arg Leu Arg Gln Gln His Ser Lys Asp Leu Gln Lys Val Val Asp Ile
1025                1030                1035                1040
Val Leu Ser His Gln Gly Val Arg Asn Lys Thr Lys Leu Ile Leu Thr
                1045                1050                1055
Leu Met Glu Lys Leu Val Tyr Pro Asn Pro Ala Val Tyr Lys Asp Gln
                1060                1065                1070
Leu Thr Arg Phe Ser Ser Leu Asn His Lys Arg Tyr Tyr Lys Leu Ala
            1075                1080                1085
Leu Lys Ala Ser Glu Leu Leu Glu Gln Thr Lys Leu Ser Glu Leu Arg
        1090                1095                1100
Thr Ser Ile Ala Arg Ser Leu Ser Glu Leu Glu Met Phe Thr Glu Glu
1105                1110                1115                1120
Arg Thr Ala Ile Ser Glu Ile Met Gly Asp Leu Val Thr Ala Pro Leu
                1125                1130                1135
Pro Val Glu Asp Ala Leu Val Ser Leu Phe Asp Cys Ser Asp Gln Thr
                1140                1145                1150
Leu Gln Gln Arg Val Ile Glu Thr Tyr Ile Ser Arg Leu Tyr Gln Pro
            1155                1160                1165
His Leu Val Lys Asp Ser Ile Gln Leu Lys Tyr Gln Glu Ser Gly Val
        1170                1175                1180
Ile Ala Leu Trp Glu Phe Ala Glu Ala His Ser Glu Lys Arg Leu Gly
1185                1190                1195                1200
Ala Met Val Ile Val Lys Ser Leu Glu Ser Val Ser Ala Ala Ile Gly
                1205                1210                1215
Ala Ala Leu Lys Gly Thr Ser Arg Tyr Ala Ser Ser Glu Gly Asn Ile
            1220                1225                1230
Met His Ile Ala Leu Leu Gly Ala Asp Asn Gln Met His Gly Thr Glu
        1235                1240                1245
Asp Ser Gly Asp Asn Asp Gln Ala Gln Val Arg Ile Asp Lys Leu Ser
    1250                1255                1260
Ala Thr Leu Glu Gln Asn Thr Val Thr Ala Asp Leu Arg Ala Ala Gly
```

-continued

```
            1265                1270                1275                1280

Val Lys Val Ile Ser Cys Ile Val Gln Arg Asp Gly Ala Leu Met Pro
                1285                1290                1295

Met Arg His Thr Phe Leu Leu Ser Asp Glu Lys Leu Cys Tyr Glu Glu
                1300                1305                1310

Glu Pro Val Leu Arg His Val Glu Pro Pro Leu Ser Ala Leu Leu Glu
                1315                1320                1325

Leu Gly Lys Leu Lys Val Lys Gly Tyr Asn Glu Val Lys Tyr Thr Pro
                1330                1335                1340

Ser Arg Asp Arg Gln Trp Asn Ile Tyr Thr Leu Arg Asn Thr Glu Asn
1345                1350                1355                1360

Pro Lys Met Leu His Arg Val Phe Phe Arg Thr Leu Val Arg Gln Pro
                1365                1370                1375

Gly Ala Ser Asn Lys Phe Thr Ser Gly Asn Ile Ser Asp Val Glu Val
                1380                1385                1390

Gly Gly Ala Glu Glu Ser Leu Ser Phe Thr Ser Ser Ile Leu Arg
                1395                1400                1405

Ser Leu Met Thr Ala Ile Glu Glu Leu Glu Leu His Ala Ile Arg Thr
                1410                1415                1420

Gly His Ser His Met Phe Leu Cys Ile Leu Lys Glu Gln Lys Leu Leu
1425                1430                1435                1440

Asp Leu Val Pro Val Ser Gly Asn Lys Val Val Asp Ile Gly Gln Asp
                1445                1450                1455

Glu Ala Thr Ala Cys Leu Leu Lys Glu Met Ala Leu Gln Ile His
                1460                1465                1470

Glu Leu Val Gly Ala Arg Met His His Leu Ser Val Cys Gln Trp Glu
                1475                1480                1485

Val Lys Leu Lys Leu Asp Ser Asp Gly Pro Ala Ser Gly Thr Trp Arg
                1490                1495                1500

Val Val Thr Thr Asn Val Thr Ser His Thr Cys Thr Val Asp Ile Tyr
1505                1510                1515                1520

Arg Glu Val Glu Asp Thr Glu Ser Gln Lys Leu Val Tyr His Ser Ala
                1525                1530                1535

Pro Ser Ser Ser Gly Pro Leu His Gly Val Ala Leu Asn Thr Pro Tyr
                1540                1545                1550

Gln Pro Leu Ser Val Ile Asp Leu Lys Arg Cys Ser Ala Arg Asn Asn
                1555                1560                1565

Arg Thr Thr Tyr Cys Tyr Asp Phe Pro Leu Ala Phe Glu Thr Ala Val
                1570                1575                1580

Gln Lys Ser Trp Ser Asn Ile Ser Ser Asp Thr Asn Arg Cys Tyr Val
1585                1590                1595                1600

Lys Ala Thr Glu Leu Val Phe Ala His Lys Asn Gly Ser Trp Gly Thr
                1605                1610                1615

Pro Val Ile Pro Met Glu Arg Pro Ala Gly Leu Asn Asp Ile Gly Met
                1620                1625                1630

Val Ala Trp Ile Leu Asp Met Ser Thr Pro Glu Tyr Pro Asn Gly Arg
                1635                1640                1645

Gln Ile Val Val Ile Ala Asn Asp Ile Thr Phe Arg Ala Gly Ser Phe
                1650                1655                1660

Gly Pro Arg Glu Asp Ala Phe Phe Glu Thr Val Thr Asn Leu Ala Cys
1665                1670                1675                1680

Glu Arg Lys Leu Pro Leu Ile Tyr Leu Ala Ala Asn Ser Gly Ala Arg
                1685                1690                1695
```

-continued

```
Ile Gly Ile Ala Asp Glu Val Lys Ser Cys Phe Arg Val Gly Trp Ser
        1700                1705                1710

Asp Asp Gly Ser Pro Glu Arg Gly Phe Gln Tyr Ile Tyr Leu Thr Glu
        1715                1720                1725

Glu Asp His Ala Arg Ile Ser Ala Ser Val Ile Ala His Lys Met Gln
        1730                1735                1740

Leu Asp Asn Gly Glu Ile Arg Trp Val Ile Asp Ser Val Val Gly Lys
1745                1750                1755                1760

Glu Asp Gly Leu Gly Val Glu Asn Ile His Gly Ser Ala Ala Ile Ala
            1765                1770                1775

Ser Ala Tyr Ser Arg Ala Tyr Glu Glu Thr Phe Thr Leu Thr Phe Val
            1780                1785                1790

Thr Gly Arg Thr Val Gly Ile Gly Ala Tyr Leu Ala Arg Leu Gly Ile
            1795                1800                1805

Arg Cys Ile Gln Arg Thr Asp Gln Pro Ile Ile Leu Thr Gly Phe Ser
        1810                1815                1820

Ala Leu Asn Lys Leu Leu Gly Arg Glu Val Tyr Ser Ser His Met Gln
1825                1830                1835                1840

Leu Gly Gly Pro Lys Ile Met Ala Thr Asn Gly Val Val His Leu Thr
            1845                1850                1855

Val Ser Asp Asp Leu Glu Gly Val Ser Asn Ile Leu Arg Trp Leu Ser
            1860                1865                1870

Tyr Val Pro Ala Asn Ile Gly Gly Pro Leu Pro Ile Thr Lys Ser Leu
            1875                1880                1885

Asp Pro Pro Asp Arg Pro Val Ala Tyr Ile Pro Glu Asn Thr Cys Asp
        1890                1895                1900

Pro Arg Ala Ala Ile Ser Gly Ile Asp Asp Ser Gln Gly Lys Trp Leu
1905                1910                1915                1920

Gly Gly Met Phe Asp Lys Asp Ser Phe Val Glu Thr Phe Glu Gly Trp
            1925                1930                1935

Ala Lys Ser Val Val Thr Gly Arg Ala Lys Leu Gly Gly Ile Pro Val
            1940                1945                1950

Gly Val Ile Ala Val Glu Thr Gln Thr Met Met Gln Leu Ile Pro Ala
            1955                1960                1965

Asp Pro Gly Gln Leu Asp Ser His Glu Arg Ser Val Pro Arg Ala Gly
        1970                1975                1980

Gln Val Trp Phe Pro Asp Ser Ala Thr Lys Thr Ala Gln Ala Met Leu
1985                1990                1995                2000

Asp Phe Asn Arg Glu Gly Leu Pro Leu Phe Ile Leu Ala Asn Trp Arg
        2005                2010                2015

Gly Phe Ser Gly Gly Gln Arg Asp Leu Phe Glu Gly Ile Leu Gln Ala
            2020                2025                2030

Gly Ser Thr Ile Val Glu Asn Leu Arg Thr Tyr Asn Gln Pro Ala Phe
            2035                2040                2045

Val Tyr Ile Pro Lys Ala Ala Glu Leu Arg Gly Gly Ala Trp Val Val
            2050                2055                2060

Ile Asp Ser Lys Ile Asn Pro Asp Arg Ile Glu Phe Tyr Ala Glu Arg
2065                2070                2075                2080

Thr Ala Lys Gly Asn Val Leu Glu Pro Gln Gly Leu Ile Glu Ile Lys
            2085                2090                2095

Phe Arg Ser Glu Glu Leu Gln Glu Cys Met Gly Arg Leu Asp Pro Glu
            2100                2105                2110
```

```
Leu Ile Asn Leu Lys Ala Lys Leu Gln Gly Val Lys His Glu Asn Gly
        2115                2120                2125
Ser Leu Pro Glu Ser Glu Ser Leu Gln Lys Ser Ile Glu Ala Arg Lys
        2130                2135                2140
Lys Gln Leu Leu Pro Leu Tyr Thr Gln Ile Ala Val Arg Phe Ala Glu
2145                2150                2155                2160
Leu His Asp Thr Ser Leu Arg Met Ala Ala Lys Gly Val Ile Lys Lys
                2165                2170                2175
Val Val Asp Trp Glu Asp Ser Arg Ser Phe Phe Tyr Lys Arg Leu Arg
        2180                2185                2190
Arg Arg Ile Ser Glu Asp Val Leu Ala Lys Glu Ile Arg Gly Val Ser
        2195                2200                2205
Gly Lys Gln Phe Ser His Gln Ser Ala Ile Glu Leu Ile Gln Lys Trp
        2210                2215                2220
Tyr Leu Ala Ser Lys Gly Ala Glu Thr Gly Ser Thr Glu Trp Asp Asp
2225                2230                2235                2240
Asp Asp Ala Phe Val Ala Trp Arg Glu Asn Pro Glu Asn Tyr Gln Glu
                2245                2250                2255
Tyr Ile Lys Glu Leu Arg Ala Gln Arg Val Ser Gln Leu Leu Ser Asp
                2260                2265                2270
Val Ala Asp Ser Ser Pro Asp Leu Glu Ala Leu Pro Gln Gly Leu Ser
        2275                2280                2285
Met Leu Leu Glu Lys Met Asp Pro Ser Arg Arg Ala Gln Phe Val Glu
        2290                2295                2300
Glu Val Lys Lys Val Leu Lys
2305                2310
```

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:10:

CGCTATAGGG AAACGTTAGA AGGATGGG                                    28

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:11:

ATCGATCGGC CTCGGCTCCA ATTTCATT                                    28

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

GTTCCCAAAG GTCTCCAAGG                                                20

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:13:

```
GCGGACTCGA GTCGACAAGC TTTTTTTTTT TTTTTTT                          37
```

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

```
ACGCGTCGAC TAGTAGGTGC GGATGCTGCG CATG                             34
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

```
GCGGACTCGA GTCGACAAGC                                             20
```

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:16:

```
ACGCGTCGAC CATCCCATTG TTGGCAACC                                   29
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

```
GACTCATTGA GATCAAGTTC                                             20
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

```
CCTCCGAGTT TCGCTCTG                                               18
```

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

TTTCCCTTGG CTATCATCA                                                19

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

TATTCTAGGG CCTATGAG                                                 18

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:21:

AGCATTGCTT GAGCTGTCTT AGTA                                          24

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:22:

CAGCGCACAT GGTACAGCAA G                                             21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

CATGGTGTCC GACTTATGCC C                                             21

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:24:

GGCGAATAGA CTGGTTAGGG TCTG                                          24

(2) INFORMATION FOR SEQ ID NO:25:

```
        (i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:25:

GCGGACTCGA GTCGACAAGC TTTTTTTTTT TTTTTTTT                                    38

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:26:

GCGGACTCGA GTCGACAAGC                                                        20

(2) INFORMATION FOR SEQ ID NO:27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:27:

GAACACGACG ACTTTTCTTC TTGG                                                   24

(2) INFORMATION FOR SEQ ID NO:28:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:28:

GGGCAGATGG TTGGAATGCA GCAC                                                   24

(2) INFORMATION FOR SEQ ID NO:29:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:29:

GACTGTGAAG CGCAGCTACA TTGC                                                   24

(2) INFORMATION FOR SEQ ID NO:30:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:30:

GAACACTGCA TCTGCGCTGT TTG                                                    23

(2) INFORMATION FOR SEQ ID NO:31:

(i) SEQUENCE CHARACTERISTICS:
```

(A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:31:

GCAACTGAAC TTCAAGATGT CGAC                                              24

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:32:

GCGCAAGAGA CATGTTGGTG AGTGC                                             25

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:33:

GCTGCTCTAG ACACTCCATA TGC                                               23

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:34:

TCAAGCAGCA GGGGTTCCGA CTCTT                                             25

(2) INFORMATION FOR SEQ ID NO:35:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:35:

GCTCATGACA CTCCATATGC AAAAACATG                                         29

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:36:

TATATGCAAC GGGTCTGTCA GGTG                                              24

(2) INFORMATION FOR SEQ ID NO:37:

(i) SEQUENCE CHARACTERISTICS:
        (A) LENGTH: 25 base pairs (B) TYPE: nucleic acid
        (C) STRANDEDNESS: single
        (D) TOPOLOGY: linear (xi) SEQUENCE DESCRIPTION: SEQ ID NO:37:

AGGATCCAGA TGACGGATTC AAGCC                                              25

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:38:

ACTGCATGTG GGAGCTGTAC ACTT                                               24

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:39:

GGATGCGTTG GTATCATCTG ATC                                                23

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:40:

GGTCGGTTAC AGCCGAATAG TATCC                                              25

(2) INFORMATION FOR SEQ ID NO:41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:41:

ACTTGGCATA CGGTGCATAC AGCGTA                                             26

(2) INFORMATION FOR SEQ ID NO:42:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:42:

CGTCGACGGT ATCATCTGAT CATTTAAGGA C                                       31

(2) INFORMATION FOR SEQ ID NO:43:

(i) SEQUENCE CHARACTERISTICS:
        (A) LENGTH: 21 base pairs
        (B) TYPE: nucleic acid

```
            (C) STRANDEDNESS: single
            (D) TOPOLOGY: linear (xi) SEQUENCE DESCRIPTION: SEQ ID NO:43:

CCAGCGGGCC ATGTCACTAC C                                              21

(2) INFORMATION FOR SEQ ID NO:44:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:44:

AACAGCTATG ACCATG                                                    16

(2) INFORMATION FOR SEQ ID NO:45:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:45:

TGGCGGCGCG CCTCCGGACG GACC                                           24

(2) INFORMATION FOR SEQ ID NO:46:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:46:

CAGACGGGGC GAACCCGGCA ATCC                                           24

(2) INFORMATION FOR SEQ ID NO:47:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:47:

TCCGGCCGAA CCGACGGTAC GCGC                                           24

(2) INFORMATION FOR SEQ ID NO:48:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:48:

CAGACGGCAC GAAGAAGCCG CCCG                                           24

(2) INFORMATION FOR SEQ ID NO:49:

(i) SEQUENCE CHARACTERISTICS:
            (A) LENGTH: 24 base pairs
            (B) TYPE: nucleic acid
            (C) STRANDEDNESS: single
```

(D) TOPOLOGY: linear (xi) SEQUENCE DESCRIPTION: SEQ ID NO:49:

GATTAAATCA TTCGCTCCAG AACT                                          24

(2) INFORMATION FOR SEQ ID NO:50:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:50:

CATTCTAGTC CAACATTCAT GGAG                                          24

(2) INFORMATION FOR SEQ ID NO:51:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:51:

CAAGGGGAAA TGGAATCGAC TCCG                                          24

(2) INFORMATION FOR SEQ ID NO:52:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:52:

TCAAGTGTAT GGACATACAC GCGC                                          24

(2) INFORMATION FOR SEQ ID NO:53:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:53:

TTCTTATTTG ATTGTTTAAT AGTA                                          24

(2) INFORMATION FOR SEQ ID NO:54:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:54:

TTTTTGAGGA TGCAATGGTG CAC                                           23

(2) INFORMATION FOR SEQ ID NO:55:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:55:

CCCTTGTGGC GCAACCAGTG ACAC                                              24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:56:

GTAGGTAGGG CCCCAACGCC TTGG                                              24

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:57:

TGGTCAGATT CCACCATTAT TGCC                                              24

(2) INFORMATION FOR SEQ ID NO:58:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:58:

TTCATCTCCC ACACATAACA CGAA                                              24

(2) INFORMATION FOR SEQ ID NO:59:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:59:

CAAAAGCATG ATATGCCCTT GTGGC                                             25

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:60:

TCCGGCCGAA CCGACGGTAC GCGC                                              24

(2) INFORMATION FOR SEQ ID NO:61:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:61:

CAAAAGCATG ATATGCCCTT GTGGC                                    25

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:62:

TGGCGGCGCG CCTCCGGACG GACC                                     24

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:63:

TTAGTCCAGG ATGATAGGAT TCTG                                     24

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:64:

CATTCTAGTC CAACATTCAT GGAG                                     24

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:65:

AGAGAAGATA TGTTTTCAGC CGAG                                     24

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:66:

TTTTTGAGGA TGCAATGGTG CAC                                      23

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:67:

```
GCGGAGCGGA CGAGGGGCTG GATC                                              24

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:68:

CGCCACAATC GCCAACCATG ATCG                                              24
```

NUCLEIC ACID SEGMENTS ENCODING WHEAT ACETYL-COA CARBOXYLASE

The United States government has certain rights in the present invention pursuant to Grant Number 90-34190-5207 from the United States Department of Agriculture.

1. BACKGROUND OF THE INVENTION

1.1 Field of the Invention

The present invention relates to plant genetics and enzymes. More specifically, it concerns methods for identifying nucleic acid segments encoding polypeptides having acetyl-CoA carboxylase (ACCase) activity, and methods for detecting ACCase polypeptides which are resistant to herbicides of the aryloxyphenoxypropionate or cyclohexanedione classes.

1.2 Description of the Related Art

1.2.1 Acetyl-CoA Carboxylase

Acetyl-CoA carboxylase [ACCase; acetyl-CoA:carbon dioxide ligase (ADP-forming), EC 6.4.1.2] catalyzes the first committed step in de novo fatty acid biosynthesis, the addition of $CO_2$ to acetyl-CoA to yield malonyl-CoA. It belongs to a group of carboxylases that use biotin as cofactor and bicarbonate as a source of the carboxyl group. ACCase catalyzes the addition of $CO_2$ to acetyl-CoA to yield malonyl-CoA in two steps as shown below.

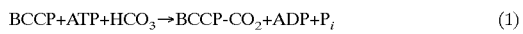

$$BCCP+ATP+HCO_3 \rightarrow BCCP\text{-}CO_2+ADP+P_i \quad (1)$$

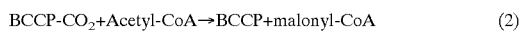

$$BCCP\text{-}CO_2+Acetyl\text{-}CoA \rightarrow BCCP+malonyl\text{-}CoA \quad (2)$$

First, biotin becomes carboxylated at the expense of ATP. The carboxyl group is then transferred to Ac-CoA (Knowles, 1989). This irreversible reaction is the committed step in fatty acid synthesis and is a target for multiple regulatory mechanisms. Reaction (1) is catalyzed by biotin carboxylase (BC); reaction (2) by transcarboxylase (TC); BCCP=biotin carboxyl carrier protein. In eukaryotic ACCase, all domains are located on one large polypeptide (e.g., animal, plant and yeast ACCase).

Yeast, rat, chicken and human ACCs are cytoplasmic enzymes consisting of 250- to 280-kDa subunits while diatom ACCase is most likely a chloroplast enzyme consisting of 230-kDa subunits. Their primary structure has been deduced from cDNA sequences (Al-feel et al., 1992; Lopez-Casillas et al., 1988; Takai et al., 1988; Roessler and Ohlrogge, 1993; Ha et al., 1994). In eukaryotes, homologs of the four bacterial genes are fused in the following order: accC, accB, accD and accA. Animal ACCase activity varies with the rate of fatty acid synthesis or energy requirements in different nutritional, hormonal and developmental states. In the rat, ACCase mRNA is transcribed using different promoters in different tissues and can be regulated by alternative splicing. The rat enzyme activity is also allosterically regulated by a number of metabolites and by reversible phosphorylation (Ha et al, 1994, Kim, 1997). The expression of the yeast gene was shown to be coordinated with phospholipid metabolism (Chirala, 1992; Haslacher et al., 1993).

While strong evolutionary conservation exists among biotin carboxylases and biotin carboxylase domains of all biotin-dependent carboxylases, BCCP domains show very little conservation outside the conserved sequence E(A/V)MKM (lysine residue is biotinylated) (Knowles, 1989; Samols et al, 1988). Although the three functional domains of the E. coli ACCase are located on separate polypeptides, plant ACCase is quite different, having all 3 domains on a single polypeptide.

At least one form of plant ACCase is located in plastids, the primary site of fatty acid synthesis. The gene encoding it, however, must be nuclear because no corresponding sequence has been seen in the complete chloroplast DNA sequences of tobacco, liverwort or rice. The idea that in some plants plastid ACCase consisted of several smaller subunits was revived by the discovery of an accD homolog in some chloroplast genomes (Li and Cronan, 1992). Indeed, it has been shown that the product of this gene in pea binds two other peptides, one of which is biotinylated. The complex may be a chloroplast isoform of ACCase in pea and some other plants (Sasaki et al., 1993).

It has been shown recently that plants have indeed more than one form of ACCase (reviewed in Sasaki et al., 1995, Konishi et al., 1996). The one located in plastids, the primary site of plant fatty acid synthesis, can be either a eukaryotic-type high molecular weight multi-functional enzyme (e.g., in wheat and maize) or a prokaryotic-type multi-subunit enzyme (e.g., in pea, soybean, tobacco and Arabidopsis). The other plant ACCase, located in the cytoplasm, is of the eukaryotic type. In Graminae, genes for both cytosolic and plastid eukaryotic-type ACCase are nuclear. No ACCase coding sequence can be found in the complete sequence of rice chloroplast DNA.

In other plants, subunits of ACCase other than the carboxyltransferase subunit encoded by a homolog of the E. coli accD gene, present in the chloroplast genome (Sasaki et al., 1995; Li and Cronan, 1992, Konishi et al., 1996), also is encoded in the nuclear DNA. Like the vast majority of plastid proteins, plastid ACCases are synthesized in the cytoplasm and then transported into the plastid. The amino acid sequence of the cytosolic and some subunits of the plastid ACCases from several plants have been deduced from genomic or cDNA sequences (e.g., Egli el al., 1995; Li and Cronan, 1992; Gornicki et al., 1994; Schulte et al., 1994; Shorrosh et al., 1994; Shorrosh et al., 1995; Roesler et al., 1994; Anderson et al., 1995). In plants, ACCase activity controls carbon flow through the fatty acid pathway and therefore may serve as an important regulation point of plant metabolism (Page et al., 1994; Post-Beitenmiller et al., 1992; Shintani and Ohlrogge, 1995).

The possibility of different ACCase isoforms, one present in plastids and another in the cytoplasm, is now accepted (Konishi et al., 1996). The rationale behind the existence of a cytoplasmic ACCase isoform is the requirement for malonyl-CoA in this cellular compartment, where it is used in fatty acid elongation and synthesis of secondary metabolites. Two isoforms of the multi-domain eukaryotic-type ACCase were found in maize, both consisting of >200-kDa subunits but differing in size, herbicide sensitivity and immunological properties. The major form was found to be located in mesophyll chloroplasts. It is also the major ACCase in the endosperm and in embryos (Egli et al., 1993).

Many more genes and cDNAs encoding ACCases from various organisms have been cloned and sequenced. These sequences are available on Genbank.

1.2.2 Herbicide Resistance

Although the mechanisms of inhibition and resistance are unknown (Lichtenthaler, 1990), it has been shown that aryloxyphenoxypropionates and cyclohexane-1,3-dione derivatives, powerful herbicides effective against monocot weeds, inhibit fatty acid biosynthesis in sensitive plants.

The aryloxyphenoxypropionate class comprises derivatives of aryloxyphenoxy-propionic acid such as diclofop, fenoxaprop, fluazifop, haloxyfop, propaquizafop and quizalofop. Several derivatives of cyclohexane-1,3-dione are also important post-emergence herbicides which also selectively inhibit monocot plants. This group comprises such compounds as oxydim, cycloxydim, clethodim, sethoxydim, and tralkoxydim.

It is known that ACCase is the target enzyme for both of these classes of herbicide in Graminae monocots (grasses). Dicotyledonous plants, on the other hand, such as soybean, rape, sunflower, tobacco, canola, bean, tomato, potato, lettuce, spinach, carrot, alfalfa and cotton are resistant to these compounds, as are other eukaryotes and prokaryotes.

Important grain crops, such as wheat, rice, maize, barley, rye, and oats, however, are monocotyledonous plants, sensitive to these herbicides. Thus herbicides of the aryloxyphenoxypropionate and cyclohexane-1,3-dione groups are not useful in the agriculture of these important grain crops owing to the inactivation of monocot ACCase by such chemicals.

1.2.3 Deficiencies in the Prior Art

The genetic transformation of important commercial monocotyledonous agriculture crops with DNA segments encoding herbicide-resistant ACCase enzymes would be a revolution in the farming of such grains as wheat, rice, maize. barley, rye, and oats. Methods of identifying ACCase-encoding nucleic acid segments, and methods of identifying ACCase polypeptides resistant to herbicides would also be important in genetically engineering grain crops and the like with desirable herbicide-resistant qualities. Likewise the availability of DNA segments encoding monocotyledonous and dicotyledonous ACCase and nucleic acid segments derived therefrom would provide a much-needed means of genetically altering the activity of ACCase in vivo and in vitro.

What is lacking in the prior art, therefore, is the development of methods and processes for their use in creation of modified, transgenic plants which have altered herbicide resistance. Moreover, novel methods providing transgenic plants using DNA segments encoding ACCase polypeptides to modulate ACCase activity, fatty acid biosynthesis in general, and oil content of plant cells in specific, are greatly needed to provide transformed plants altered in such activity. Methods for determining ACCase activity in vivo and quantitating herbicide resistance in plants would also represent major improvements over the current state of the art.

2. SUMMARY OF THE INVENTION

The present invention seeks to overcome these and other inherent deficiencies in the prior art by providing compositions comprising novel ACCase polypeptides and DNA segments encoding them from eukaryotic, and particularly, plant species. Also disclosed are methods for determining herbicide resistance and kits for identifying the presence of plant ACCase polypeptides and DNA segments.

The ACCase of a method of the present invention include, but is not limited to, wheat cytosolic ACCases such as ACC C1, ACC C2, ACC C3, ACC C4, or ACC C5, or wheat plastid ACCases such as ACC P1 or ACC P2, or proteins which are functionally-equivalent and/or homologous to those disclosed herein. The inventors contemplate that virtually any nucleic acid segment encoding an ACCases may be useful in the practice of the present invention.

While the inventors contemplate that a desirable vector for the expression of an ACCase in a yeast cell may include a vector existing in a cell in a high or relatively high copy number, in certain applications of the method, one may desire a medium, low or even single copy-number vector.

The present invention also may be utilized for the purification and structural study of ACCase polypeptides, ACCase polypeptide fragments, or variants thereof. The inventors contemplate the use of peptide "tags", such as a His tag, an antibody, a biotin/avidin tag, or even a maltose binding protein tag may facilitate the purification of said polypeptide. Peptide tags are amino acid segments that may be added to a polypeptide and are generally used to facilitate the purification of the peptide. Methods of purifying polypeptides containing peptide tags are well known to those of skill in the art.

2.1 ACCase-Encoding Genes and Polynucleotides

The present invention provides polynucleotides and polypeptides relating to a whole or a portion of acetyl-CoA carboxylase (ACCase) of a plant as well as processes using those polynucleotides and polypeptides.

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 150,000 base pairs. Preferred lengths of particular polynucleotides are set forth hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

In an important embodiment, the present invention contemplates isolated and purified polynucleotides comprising DNA segments encoding an acetyl-CoA carboxylase protein of a plant. Preferably, the plant is a monocotyledonous plant, and in particular, a monocotyledonous plant such as wheat, rice, maize, barley, rye, oats or timothy grass, or alternatively, a dicotyledonous plant such as soybean, rape, sunflower, tobacco, Arabidopsis, petunia, pea, canola, bean, tomato. potato, lettuce, spinach, alfalfa, cotton or carrot.

Preferably, a polypeptide is an acetyl-CoA carboxylase (ACCase) protein of a plant. This polypeptide participates in the carboxylation of acetyl-CoA. In a preferred embodiment, an ACCase polypeptide is encoded by a polynucleotide comprising an ACCase gene which has the nucleic acid sequence of SEQ ID NO:1 (ACCase C1), SEQ ID NO:2 (ACCase C2), SEQ ID NO:3 (ACCase C3), SEQ ID NO:4 (ACCase C4), SEQ ID NO:5 (ACCase C5), SEQ ID NO:6 (wheat plastid ACCase cDNA, pcw), SEQ ID NO:7 (ACCase P1), or SEQ ID NO:8 (ACCase P2) or functional equivalents thereof. The ACCase polypeptide preferably comprises the amino acid sequence of SEQ ID NO:9 or functional equivalents thereof.

In a further embodiment, the present invention provides a method of selecting a nucleic acid segment encoding a polypeptide having ACCase activity. The method generally involves obtaining a nucleic acid segment suspected of encoding a polypeptide having ACCase activity; transforming a yeast cell lacking ACCase activity with the nucleic acid segment; expressing the nucleic acid segment in the yeast cell; identifying transformed yeast that contain ACCase activity; and characterizing nucleic acid segment that encodes ACCase activity from the yeast cell of step, such that the detection of ACCase activity in the transformed cell is an indication of the presence in the cell, a nucleic acid segment that encodes a polypeptide having ACCase activity.

In a further embodiment, the present invention provides a method of analyzing ACCase polypeptides for acetyl coenzyme-A carboxylase activity. Activity may be accessed in vivo by determining the ability of the expressed ACCase polypeptide, ACCase polypeptide fragment, or variant thereof to complement a mutation in a yeast ACCase gene. Alternatively, activity may be accessed in vitro by expressing the ACCase polypeptide, ACCase polypeptide fragment, or variant thereof in yeast and biochemically purifying the polypeptide. Methods of determining activity of purified ACCase polypeptides are well known to those of skill in the art. The method of the present invention may be used to determine the activity of chimeric polypeptides made up of a combination of ACCase polypeptides. Chimeric proteins may comprise, but are not limited to, cytosolic or plastid ACCase sequences. Furthermore, the present invention provides for a method of determining the acetyl coenzyme A carboxylase activity of ACCase polypeptides containing mutations.

2.2 ACCase Transformation and Identification of Herbicide-Resistant Variants

In yet another aspect, the present invention provides a process of modulating the herbicide resistance of a plant cell by a process of transforming the plant cell with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a host cell, such as a yest cell, animal cell, bacterial cell, or a plant cell.

Preferably, a polypeptide is an acetyl-CoA carboxylase enzyme and, more preferably, a plant acetyl-CoA carboxylase. In a preferred embodiment, a coding region includes the DNA sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 and a promoter is a GAL promoter most preferably GAL 10.

In a preferred embodiment, a cell is a yeast cell and a plant polypeptide is a monocotyledonous plant acetyl-CoA carboxylase enzyme such as wheat acetyl-CoA carboxylase enzyme. The enzyme may be cytosolic or plastid. The present invention also provides a transformed yeast cell produced in accordance with such a process.

Preferably, the acetyl-CoA carboxylase is a dicotyledonous plant acetyl-CoA carboxylase enzyme or a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a monocotyledonous plant acetyl-CoA carboxylase or one or more domains of a cyanobacterial acetyl-CoA carboxylase. The plant acetyl-CoA carboxylase, or portions thereof, may be cytosolic or plastid.

Where a yeast cell is transformed with a nucleic acid segment encoding a polypeptide having ACCase activity, that yeast cell may be used to identify a herbicide resistant ACCase. In another embodiment, the yeast cell may be used to identify herbicide resistant mutations in a gene encoding an ACCase. In accordance with such a use, the present invention provides a method for identifying a herbicide resistant ACCase. The method generally involves obtaining a nucleic acid segment suspected of encoding a polypeptide having ACCase activity; transforming a yeast cell lacking ACCase activity with the nucleic acid segment to form transformed or transfected yeast; expressing the nucleic acid in the transformed yeast cell; exposing the transformed yeast cell to a effective amount of a herbicide that inhibits ACCase activity; identifying the transformed yeast that are resistant to the herbicide; and characterizing the nucleic acid segment from the transformed yeast of step.

Means for transforming yeast as well as expression vectors used for such transformation are preferably the same as set forth above. In a preferred embodiment, yeast cells are transformed or transfected with an expression vector comprising a coding region that encodes wheat ACCase. Yeast cells resistant to the herbicide are identified. Identifying comprises growing or culturing transformed cells in the presence of the herbicide and recovering those cells that survive herbicide exposure. Transformed, herbicide-resistant cells are then grown in culture, collected and total DNA extracted using standard techniques. ACCase DNA is isolated, amplified if needed and then characterized by comparing that DNA with DNA from ACCase known to be inhibited by that herbicide.

In another embodiment, the present invention provides a method of analyzing the susceptibility of ACC polypeptides, ACC polypeptide fragments, or variants thereof to inhibitors. In preferred embodiments, the inhibitors belong to the classes of aryloxyphenoxypropionates or cyclohexanediones. The method of the present invention may be used to determine the sensitivity of chimeric polypeptides made up of a combination of ACC polypeptides to inhibitors. Chimeric proteins may comprise, but are not limited to, cytosolic or plastid ACC sequences. Furthermore, the present invention provides for a method of determining the sensitivity of ACC polypeptides containing mutations to inhibitors.

In an further embodiment, the present invention provides methods for developing new selectable markers for use in a transformed host cell, and in particular for herbicide sensitive cells, such as monocotyledonous plants (Graminae) including wheat. The method generally involves cotransformation of the host cell with a herbicide-resistant ACCase gene and a gene of interest. and culturing the transformed cell in the presence of the herbicide.

2.3 ACCase Transgenes and Transgenic Plants

In yet another aspect, the present invention provides a process of altering the carboxylation of acetyl-CoA in a cell comprising transforming the cell with a DNA molecule comprising a promoter operatively linked to a coding region that encodes a plant polypeptide having the ability to catalyze the carboxylation of acetyl-CoA, which coding region is operatively linked to a transcription-terminating region, whereby the promoter is capable of driving the transcription of the coding region in the cell. The invention also provides a means of reducing the amount of ACCase in plants by expression of ACCase antisense mRNA.

An important aspect of the present invention involves operatively linking a ACCase polypeptide to a targeting signal to ensure translocation of the ACCase to one or more desired cell compartments (e.g., plastids, or plastids). In yet another aspect, the inventors contemplate the use of a tissue-specific promoter to express a nucleic acid segment encoding a polypeptide having ACCase activity in a particular location of the plant or plant tissues, (e.g., roots, shoots, seeds, tubers, etc.). Likewise, a developmental- or cell-cycle-specific promoter may be used to permit expression of the polypeptide in a particular tissue or particular stage(s) of plant development.

The inventors contemplate that targeting of polypeptides having ACCase activity to plastids (plastids) may alter fatty acid biosynthesis within them. Furthermore, the inventors contemplate that the use of tissue-specific expression of polypeptides having ACCase activity may permit the altering of a particular cellular component (such as oil) in specific tissues (e.g., seeds, fruit. root, etc.) without affecting the production of the component in the whole plant.

Another aspect of the invention relates generally to transgenic plants which express genes or gene segments encoding the novel polypeptide compositions disclosed herein. As used herein, the term "transenic plants" is intended to refer to plants that have incorporated DNA sequences. including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

A preferred gene which may be introduced includes, for example, the ACCase DNA sequences from plant species such as wheat, of any of those sequences which have been genetically engineered to decrease or increase the activity of the ACCase in such transgenic species.

Vectors, plasmids, cosmids, YACs (yeast artificial chromosomes) and DNA segments for use in transforming such cells will, of course, generally comprise either the cDNA, gene or gene sequences of the present invention, and particularly those encoding ACCase. These DNA constructs can further include structures such as promoters, enhancers, polylinkers, or even regulatory genes as desired. The DNA segment or gene may encode either a native or modified ACCase, which will be expressed in the resultant recombinant cells, and/or which will impart an improved phenotype to the regenerated plant.

Such transgenic plants may be desirable for increasing the herbicide resistance of a monocotyledonous plant, by incorporating into such a plant, a transgenic DNA segment encoding a plant acetyl-CoA carboxylase enzyme which is resistant to herbicide inactivation, e.g., a dicotyledonous ACCase gene. Alternatively a cyanobacterial ACCase polypeptide-encoding DNA segment could also be used to prepare a transgenic plant with increased resistance to herbicide inactivation.

Alternatively transgenic plants may be desirable having an decreased herbicide resistance. This would be particularly desirable in creating transgenic plants which are more sensitive to such herbicides. Such a herbicide-sensitive plant could be prepared by incorporating into such a plant, a transgenic DNA segment encoding a plant acetyl-CoA carboxylase enzyme which is sensitive to herbicide inactivation, e.g., a monocotyledonous ACCase gene, or a mutated dicotyledonous or cyanobacterial ACCase-encoding gene.

In other aspects of the present invention, the invention concerns processes of modifying the oil content of a plant cell. Such modifications generally involve expressing in such plant cells transgenic DNA segments encoding a plant or cyanobacterial acetyl-CoA carboxylase composition of the present invention. Such processes would generally result in increased expression of ACCase and hence, increased oil production in such cells. Alternatively, when it is desirable to decrease the oil production of such cells, ACCase-encoding transgenic DNA segments or antisense (complementary) DNA segments to genomic ACCase-encoding DNA sequences may be used to transform cells. Either process may be facilitated by introducing into such cells DNA segments encoding a plant or cyanobacterial acetyl-CoA carboxylase polypeptide, as long as the resulting transgenic plant expresses the acetyl-CoA carboxylase-encoding transgene.

The present invention also provides a transformed plant produced in accordance with the above process as well as a transgenic plant and a transgenic plant seed having incorporated into its genome a transgene that encodes a herbicide resistant polypeptide having the ability to catalyze the carboxylation of acetyl-CoA. All such transgenic plants having incorporated into their genome transgenic DNA segments encoding plant or cyanobacterial acetyl-CoA carboxylase polypeptides are aspects of this invention.

Alternatively, one may desire to alter transcription activity of a native ACCase gene promoter. Genomic clones disclosed herein comprise such promoters.

2.4 DNA Segments

The present invention also concerns DNA segments, that can be isolated from virtually any source, that are free from total genomic DNA and that encode the novel peptides disclosed herein. DNA segments encoding these peptide species may prove to encode proteins, polypeptides, subunits, functional domains, and the like of ACCase-related or other non-related gene products. In addition these DNA segments may be synthesized entirely in vitro using methods that are well-known to those of skill in the art.

As used herein the term "DNA segment" refers to a DNA molecule that has been isolated free of total genomic DNA of a particular species. Therefore, a DNA segment encoding an ACCase peptide refers to a DNA segment that contains ACCase coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified ACCase gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding ACCase, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an ACCase peptide species that includes within its amino acid sequence an amino acid sequence essentially as set forth in any of SEQ ID NO:9.

The term "a sequence essentially as set forth in any of SEQ ID NO:9" means that the sequence substantially corresponds to a portion of the sequence of either SEQ ID NO:9 and has relatively few amino acids that are not identical to, or a biologically functional equivalent of, the amino acids of any of these sequences. The term "biologically functional equivalent" is well understood in the art and is further defined in detail herein (for example, see Section 2.10). Accordingly, sequences that have between about 70% and about 80%, or more preferably between about 81% and about 90%, or even more preferably between about 91% and about 99% amino acid sequence identity or functional equivalence to the amino acids of any of SEQ ID NO:9 will be sequences that are "essentially as set forth in any of SEQ ID NO:9"

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1, SEQ ID NO:2, SEQ ID NO:3, SEQ ID NO:4, SEQ ID NO:5, SFQ ID NO:6, SEQ ID NO:7, or SEQ ID NO:8, such as about 14 or 15 or 16 or 17, or 18 nucleotides, and that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, 33 etc.; 40, 41, 42, 43, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

The various probes and primers designed around the disclosed nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It will also be understood that this invention is not limited to the particular nucleic acid sequences which encode peptides of the present invention, or which encode the amino acid sequence of SEQ ID NO:9, including the DNA sequence which is particularly disclosed in SEQ ID NO:6. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as plastid targeting signals, or "tags" for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an ACCase peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of ACCase peptides or epitopic core regions, such as may be used to generate anti-ACCase antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from a sequence such as SEQ ID NO:9.

In addition to their use in directing the expression of ACCase peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region such as about 14 or 15 or 16 or 17, or 18 nucleotide long contiguous sequence that has the same sequence as, or is complementary to, a such as about 14 or 15 or 16 or 17, or 18 nucleotide long contiguous DNA segment any of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 will find particular utility. Longer contiguous identical or complementary sequences, e.g., those of about 19, 20, 21, 22, 23, etc.; 30, 31, 32, 33 etc.; 40, 41, 42, 43, etc.; 50, 51, 52, 53, etc.; 100, 101, 102, 103, etc.; 150, 151, 152, 153, etc.; including all integers through the 200–500; 500–1,000; 1,000–2,000; 2.000–3,000; 3,000–5,000; 5,000–10,000 ranges, up to and including sequences of about 12,001, 12,002, 13,001, 13,002 and the like will also be of use in certain embodiments.

The ability of such nucleic acid probes to specifically hybridize to ACCase-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of such as 14, 15, 16, 17, 18, 19, 20, etc.; 21, 22, 23, etc.; 30, 31, 32, 33 etc.; 40, 41, 42, 43, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like nucleotides or so, identical or complementary to DNA sequences of any of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 are particularly contemplated as hybridization probes for use in, e.g, Southern and Northern blotting. Smaller fragments will generally find use in hybridization embodiments, wherein the length of the contiguous complementary region may be varied, such as between about 10 to 14 and about 100 or 200 nucleotides, but larger contiguous complementarity stretches may be used, according to the length complementary sequences one wishes to detect.

The use of a hybridization probe of about 14, 15, 16, 17, 18, or 19 nucleotides in length allows the formation of a duplex molecule that is both stable and selective. Molecules having contiguous complementary sequences over stretches greater than 14, 15, 16, 17, 18, or 19 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating ACCase-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1990; 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate ACCase-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.5 Biological Functional Equivalents

Modification and changes may be made in the structure of the peptides of the present invention and DNA segments which encode them and still obtain a functional molccule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons listed in Table 1.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example. their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1A. Structure of yeast expression plasmids encoding yeast and wheat cytosolic ACCase.

Figure 1B:
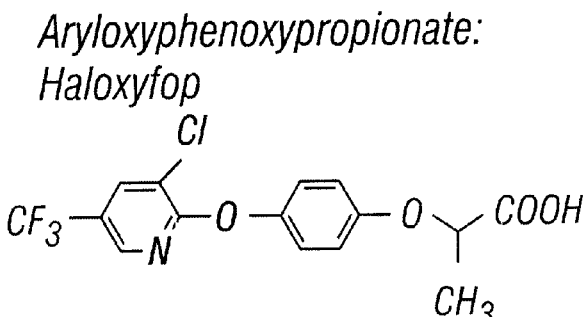
Figure 1B:
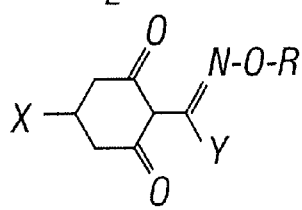

FIG. 1B Structure of ACCase inhibitors used.

Figure 2:
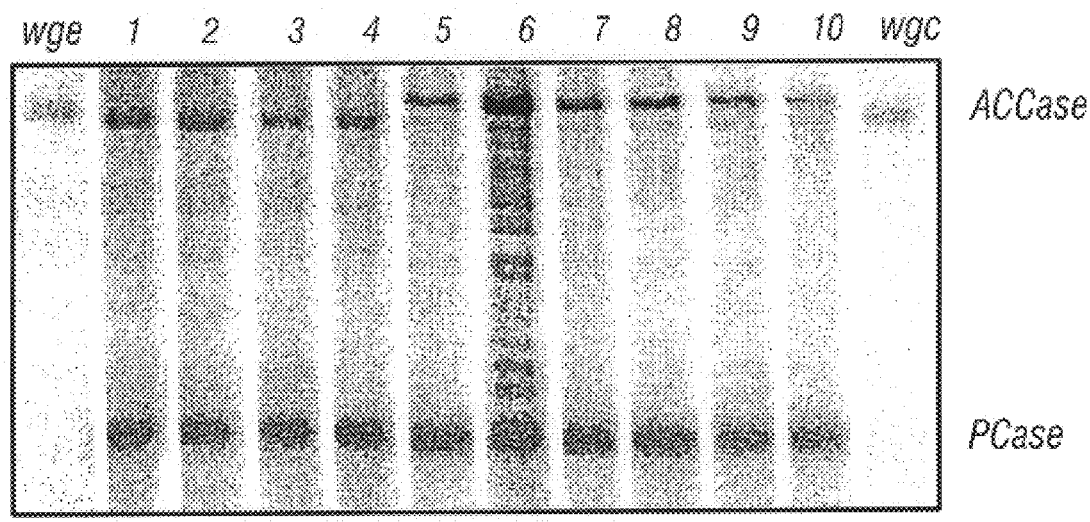

FIG. 2. Biotinylated proteins in yeast strains. Western blot was probed with $^{35}$S-streptavidin to reveal biotinylated peptides. Equal amounts of protein from strains 1–10 listed in Table 3 were loaded (lane 1–10); wge, wheat germ extract; PCase, pyruvate carboxylase (lane 1–10).

Figure 3A:
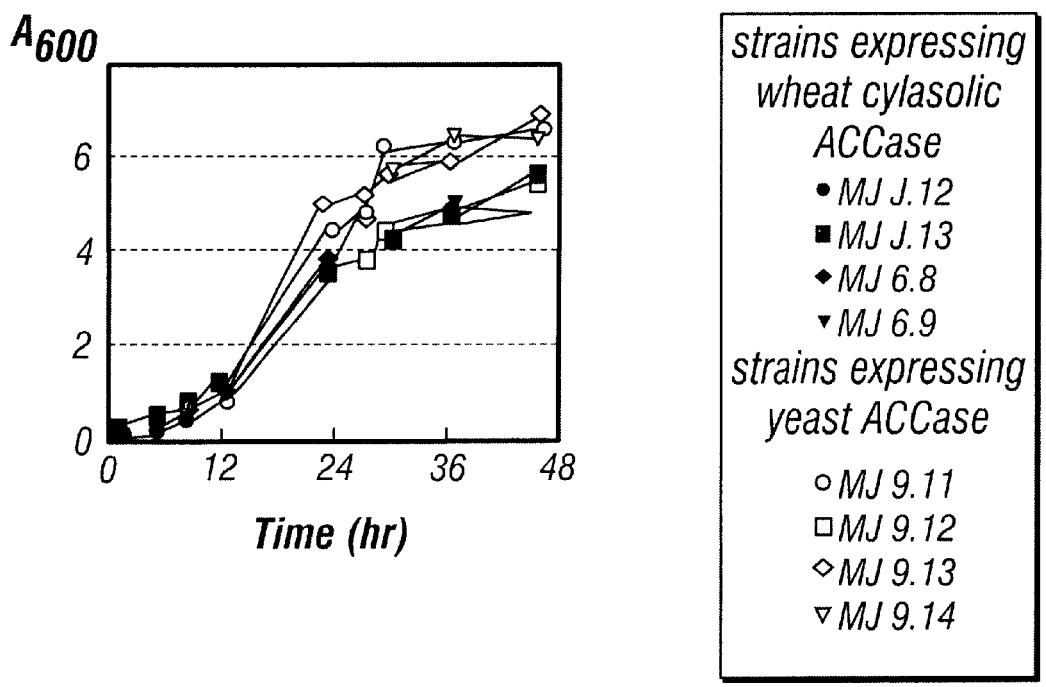
Figure 3B:
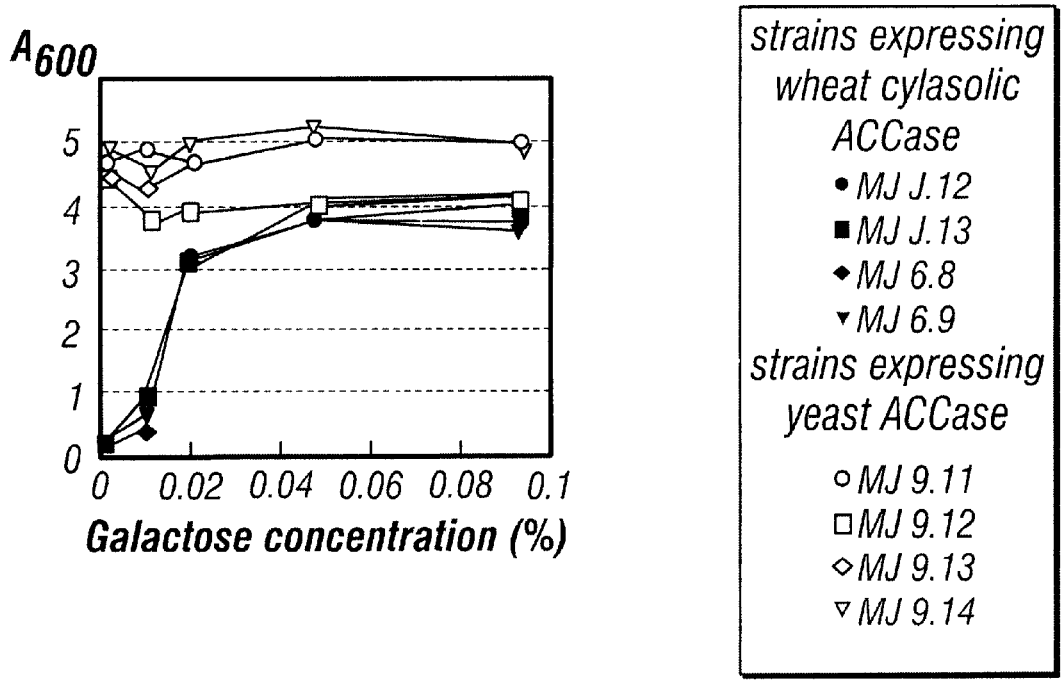

FIG. 3A and FIG. 3B. Growth curves (FIG. 3A) and galactose dependence (FIG. 3B) of gene-replacement and wild-type yeast strains. Growth in YPRG medium (FIG. 3A) or in the presence of various amounts of galactose in YPR medium (FIG. 3B) was monitored by $A_{600}$ measurements. Galactose induction was measured 24 hrs after inoculation from cultures grown in YPR medium for about 24 hrs.

Figure 4A:
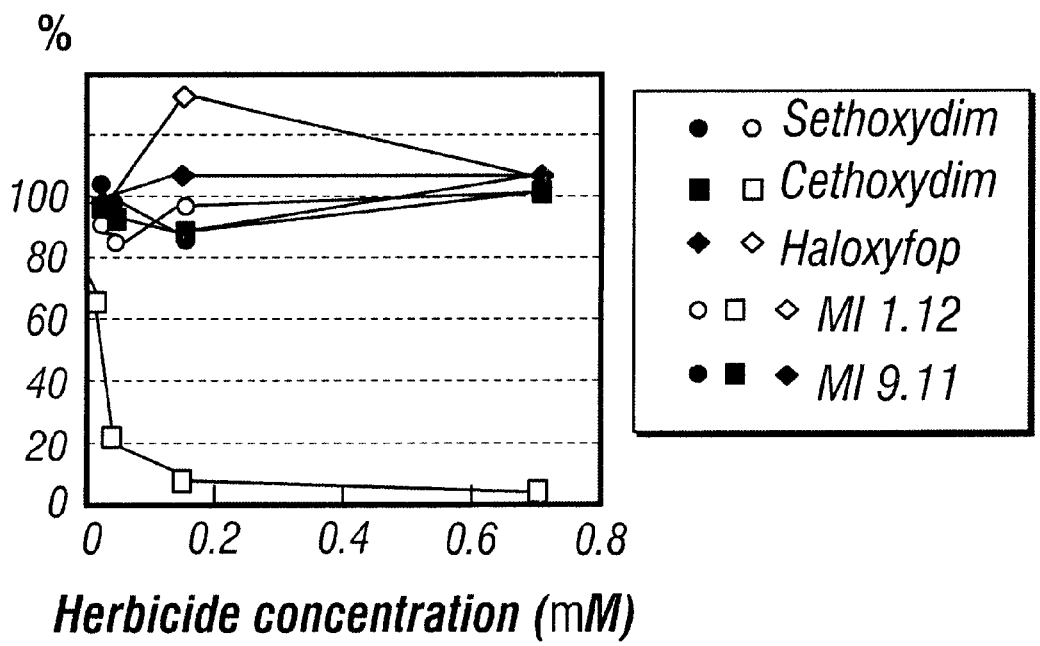
Figure 4B:
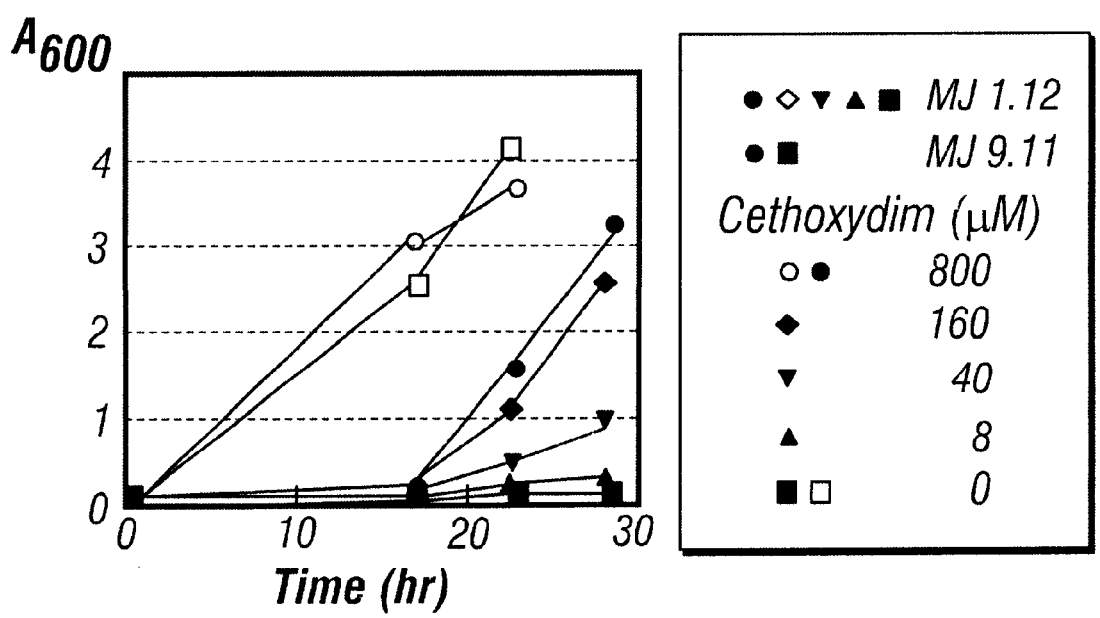

FIG. 4A and FIG. 4B. Growth inhibition of yeast strains expressing wheat cytosolic or yeast ACCase. Growth in YPR medium containing 0.01% galactose and various amounts of inhibitors was monitored by $A_{600}$ measurements. Relative culture densities 24 hrs after inoculation are shown in (FIG. 4A). Growth curves in the presence of cethoxydim are shown in (FIG. 4B).

Figure 5:
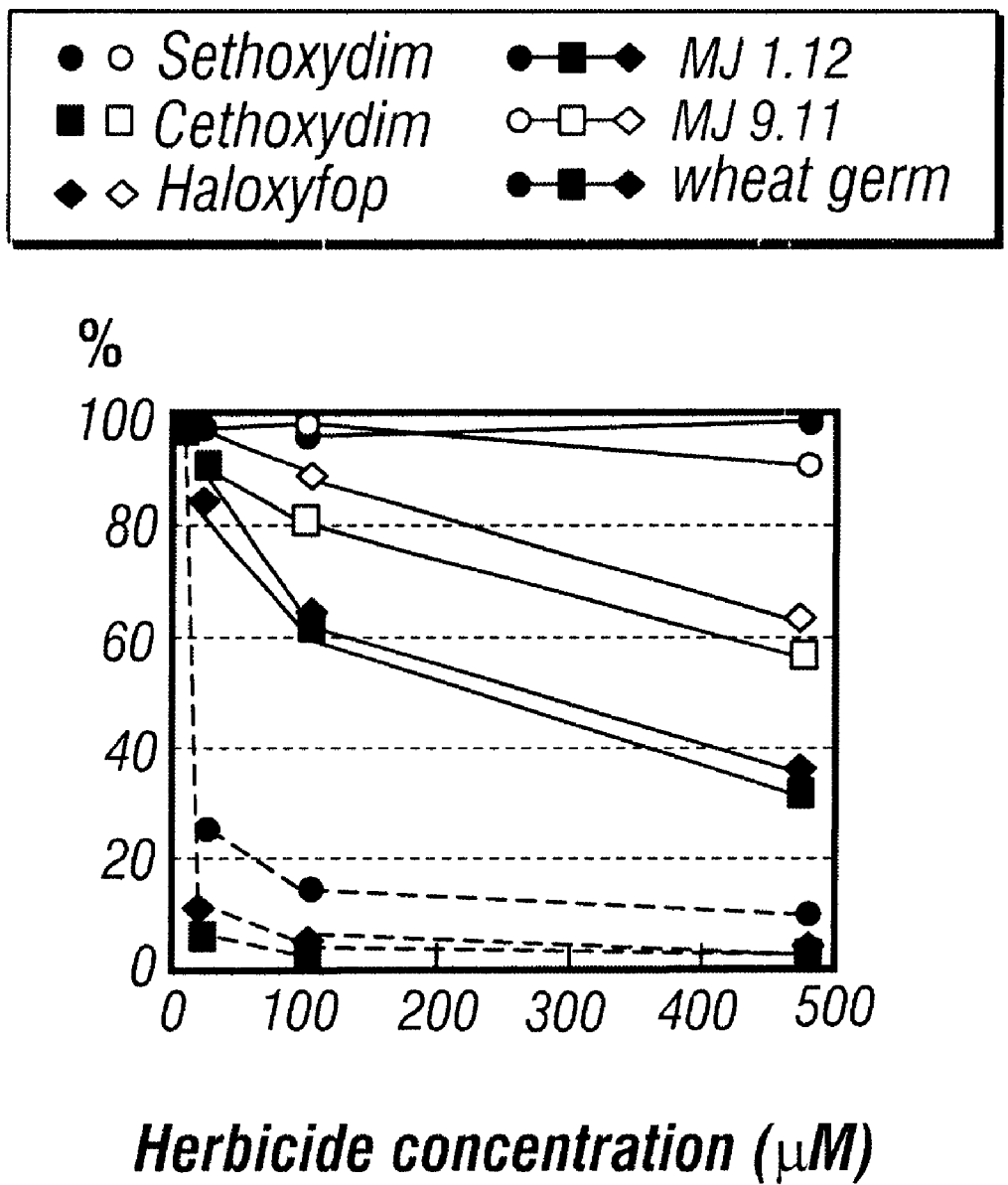

FIG. 5. In vitro inhibition of wheat cytosolic ACCase expressed in the yeast gene-replacement strain, along with yeast and wheat germ ACCases. Relative acetyl CoA-dependent conversion of radioactive bicarbonate into acid-stable malonyl-CoA was measured in the presence of various amounts of the inhibitors.

Figure 6:
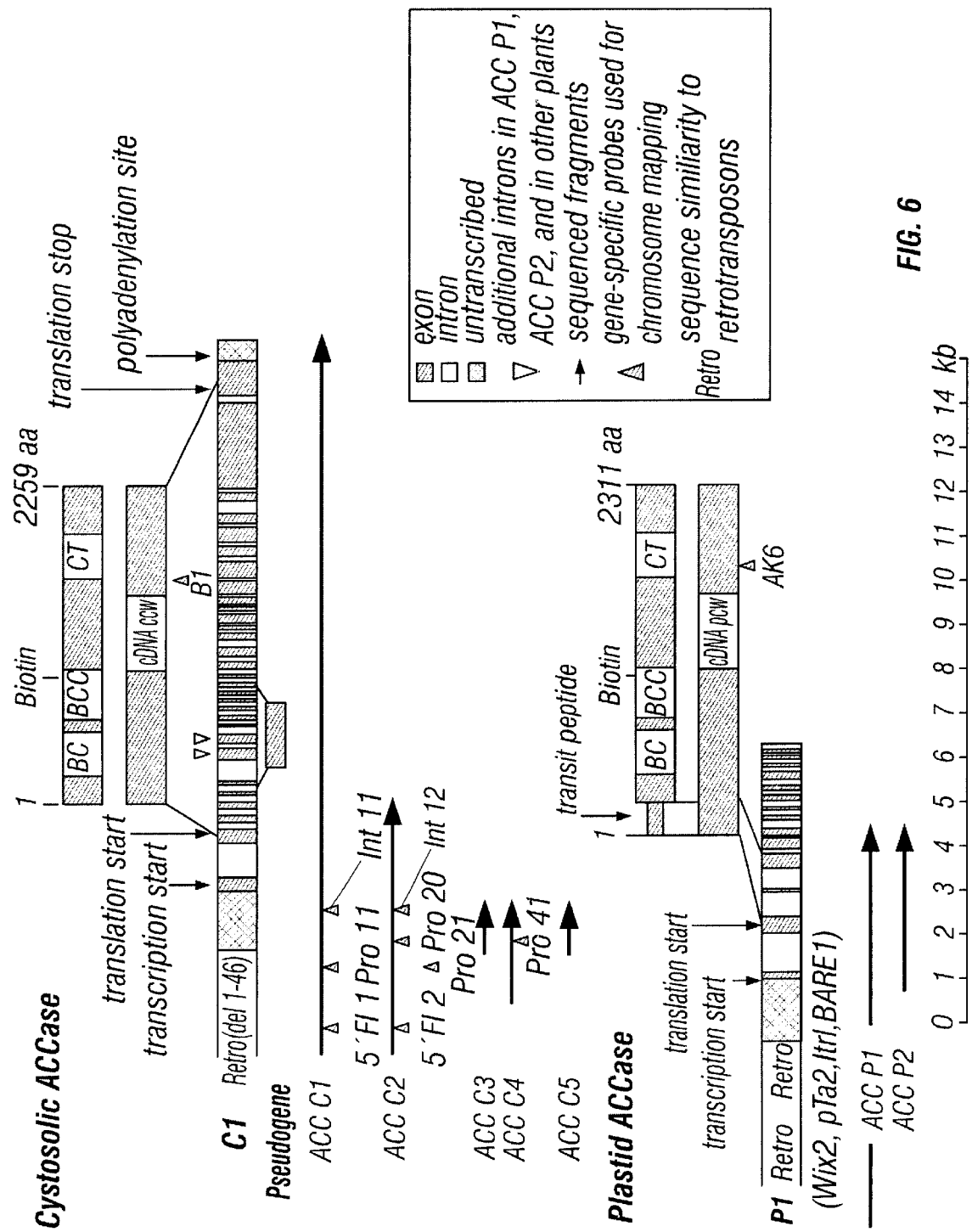

FIG. 6. Structure of wheat cytosolic and plastid ACCases and their genes. Arrows indicate sequenced fragments of genomic clones. Localization of the ACCase functional domains was established before (Gornicki el al., 1994). BC, biotin carboxylase; BCC, biotin carboxyl carrier; CT, carboxyltransferase. cDNA ccw, coding sequence of cytosolic ACCase from wheat, cDNA pcw, coding sequence of plastid ACCase from wheat.

Figure 7:
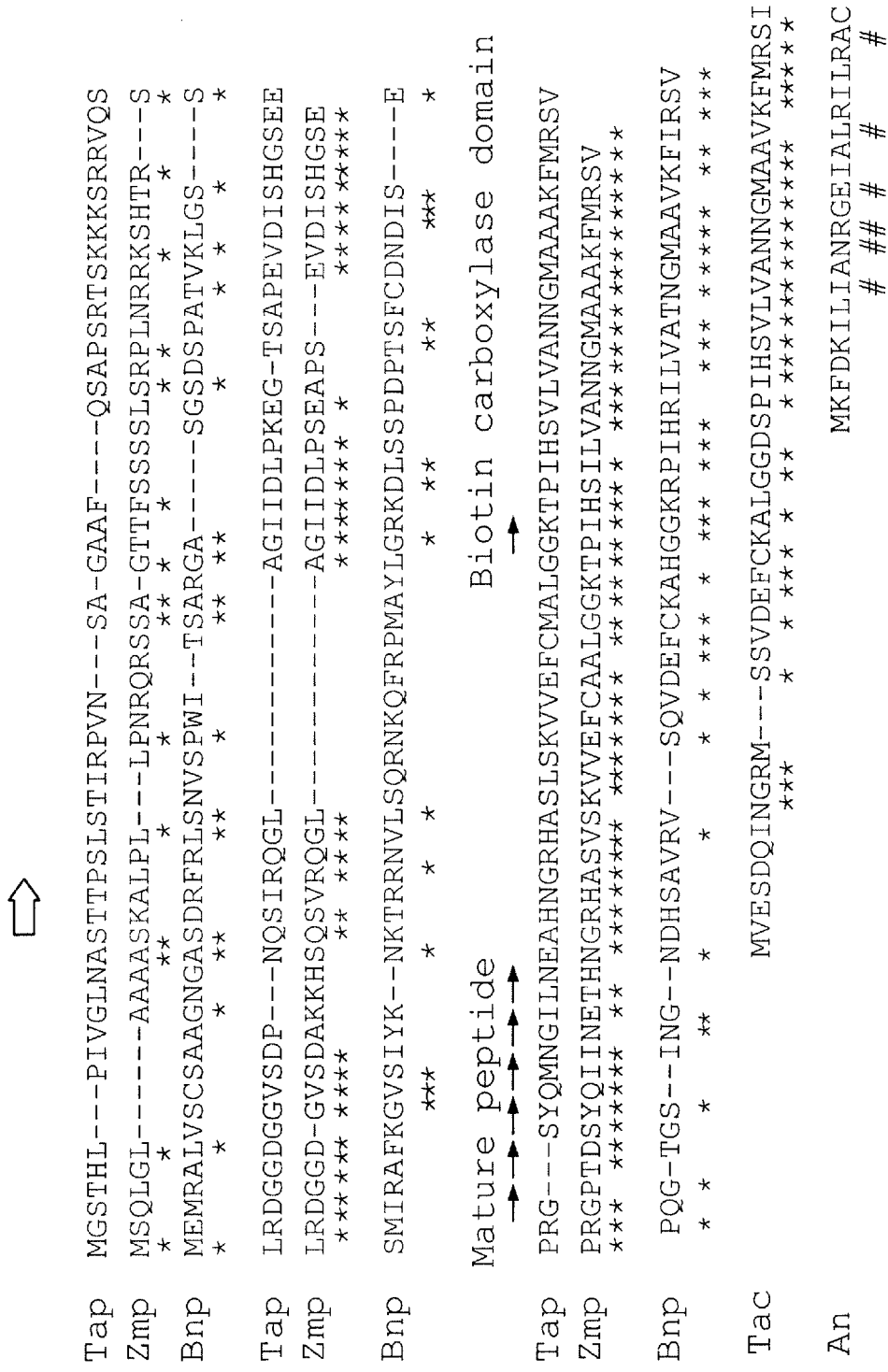

FIG. 7. Alignment of amino acid sequences of the N-termini of *T. aestivum* plastid ACCase (Tap), *Zea mays* plastid ACCase (Zmp), *Brassica napus* plastid ACCase, (Bnp), *T. aestivum* cytosolic ACCase (Tac), and the biotin-carboxylase subunit of Anabaena 7120 ACCase (An). "*" indicates aminoacid identity with the *T. aestivum* plastid ACCase, "#" indicates amino acid identical in all the sequences. The first amino acid present in all sequences identifies the beginning of the biotin carboxylase domain. The beginning of the mature ACCase (processing site) has not yet been established for any of the plastid ACCases.

FIG. 8A, FIG. 8B, and FIG. 8C. Genetic linkage analysis of wheat ACCase genes in *Aegilops tauschii* the D genome progenitor of the D genome of common bread wheat. Maps of only one arm of chromosome 2, 3 and 5 are shown in detail. Probes specific for plastid (AK6) and cytosolic (B1, Intl1, Pro21, Pro4 and Pro 1) ACCase genes are indicated in bold. Names of markers and distances in centimorgans (cM) are shown.

4. DESCRIPTION OF ILLUSTRATIVE EMBODIMENTS

4.1 Definitions

The following words and phrases have the meanings set forth below:

A, an: In accordance with long standing patent law convention, the words "a" and "an" when used in this application, including the claims, denotes "one or more".

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant. A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

4.2 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide disclosed herein, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP Carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van TIunen et al., 1988), bean olycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransfcrase II and nopaline synthase 3' nontranslated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

In one embodiment, an expression vector comprises a coding region that encodes a plant polypeptide having the ability to catalyze the carboxylation of acetyl-CoA. Such a plant polypeptide is preferably a monocotylcdonous or a dicotyledonous plant acetyl-CoA carboxylase enzyme. A preferred monocotyledonous plant polypeptide encoded by such a coding region is preferably wheat ACCase, which ACCase includes the amino acid residue sequence of SEQ ID NO:9 or functional equivalents thereof. A preferred coding region includes the DNA sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. Alternatively, a preferred plant ACCase, such as wheat ACCase, is also preferred. Such an ACCase enzyme is encoded by the DNA segment of SEQ ID NO:6 and has the amino acid sequence of SEQ ID NO:9.

4.3 Production and Characterization of Stable Transgenic Plants 4.3.1 Selection

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. The above techniques also could be utilized if the screenable marker is the green fluorescent protein.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. Therefore it is proposed that combinations of selection and screening will enable one to identify transfoimants in a wider variety of cell and tissue types.

4.3.2 Characterization

To confirm the presence of the exogenous DNA or "transgene (s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

4.3.2.1 DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transformant, but does not prove integration of the introduced gene into the host cell genome. It is the experience of the inventors, however, that DNA has been integrated into the genome of all transformants that demonstrate the presence of the gene through PCR™ analysis. In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transforrnants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™ e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Whereas DNA analysis techniques may be conducted using DNA isolated from any part of a plant, RNA will only be expressed in particular cells or tissue types and hence it will be necessary to prepare RNA for analysis from these tissues. PCR™ techniques may also be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

4.3.2.2 Gene Expression

While Southern blotting and PCR™ may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays. An example is to evaluate resistance to insect feeding.

4.4 Transformed or Transgenic Plant Cells

A bacterium, a yeast cell, or a plant cell or a plant transformed with an expression vector is also contemplated. A transgenic bacterium, yeast cell, plant cell or plant derived from such a transformed or transgenic cell is also contemplated. Means for transforming bacteria and yeast cells are well known in the art. Typically, means of transformation are similar to those well known means used to transform other bacteria or yeast such as *E. coli* or *Saccharomyces cerevisiae*.

Methods for DNA transformation of plant cells include Agrobacteriuim-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993) by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson 1988a; 1988b); and (4) receptor-mediated mechanisms (Curiel et al., 1991; 1992; Wagner et al., 1992).

4.4.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.4.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment. in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultuled in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/ microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.4.3 Agrobacterium-Mediated Transfer

Agrobacterium-mediated transfer is a widely applicable system for introducing (genes into plant cells because the DNA can be introduced into whole plant tissues, thereby bypassing the need for regeneration for an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee el al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobactceriurn containing both arrned and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agr 07obacterimn naturally infects. Agrobacterium-mediated transformation is most efficient in dicotyledonous plants. Few monocots appear to be natural hosts for Agrobacterium, although transgenic plants have been produced in asparagus using Agrobacterium vectors. Therefore. commercially important cereal grains such as rice, corn, and wheat must usually be transformed using alternative methods. However, as mentioned above, the transformation of asparagus using Agrobacterium can also be achieved.

A transgenic plant formed using Agrobacterium transformation methods typically contains a single gene on one chromosome. Such transgenic plants can be referred to as being heterozygous for the added gene. However, inasmuch as use of the word "heterozycous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (, e.g., Potrykus et al., 1985; Lorz et al., 1985; Fromm et al., 1985; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.5 Methods for Preparing Mutagenized DNA Segments

In certain circumstances, it may be desirable to modify or alter one or more nucleotides in one or more of the promoter sequences disclosed herein for the purpose of altering or changing the transcriptional activity or other property of the promoter region. In general, the means and methods for mutagenizing a DNA segment are well-known to those of skill in the art. Modifications to such segments may be made by random, or site-specific mutagenesis procedures. The promoter region may be modified by altering its structure through the addition or deletion of one or more nucleotides from the sequence which encodes the corresponding un-modified promoter region.

Mutagenesis may be performed in accordance with any of the techniques known in the art such as and not limited to synthesizing an oligonucleotide having one or more mutations within the sequence of a particular promoter region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent neucleotides, to provide a primer sequence of sufficient size and sequence complexity to form a stable duplex on both sides of the deletion junction being traversed. Typically, a primer of about 17 to about 75 nucleotides or more in length is preferred with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired promoter region or peptide. An oligonucleotide primer bearing the desired mutated sequence is prepared, generally synthetically. Thlis primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (refelTed to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method. in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes tliroughout a region targeted for amplification, followed by a repair reaction in which only two of the four bases are present. The other two bases can be added as biotinylated derivatives for easy detection. A similar approach is used in SDA.

Still other amplification methods described in Great Britain Pat. Appl. No. 2 202 328, and in Intl. Pat. Appl. Publ. No. PCT/US89/01025, each of which is incorporated herein by reference in its entirety, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; Intl. Pat. Appl. Pubt. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACF" (Frohman, 1990) and "one-sided PCR™" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.6 Regulatory Elements

Constructs will include the promoters of the present invention functionally linked to a gene of interest, and optionally including a 3' end DNA sequence that acts as a signal to terminate transcription and allow for the polyadenylation of the resultant mRNA. The most preferred 3' elements are contemplated to be those from the nopalinc synthase gene of *Agrobacterium tumefasciens* (Bevan et al., 1983), the terminator for the T7 transcript from the octopine synthase gene of *Agrobacteriutm tumefasciens*, and the 3' end of the protease inhibitor I or II genes from potato or tomato. Regulatory elements such as Adh intron 1 (Callis et al., 1987), sucrose synthase intron (Vasil el al., 1989) or TMV omega element (Gallie, et al., 1989), may further be included where desired.

As the DNA sequence between the transcription initiation site and the start of the coding sequence, i.e. the untranslated leader sequence, can influence gene expression, one may also wish to employ a particular leader sequence. Preferred leader sequences are contemplated to include those which include sequences predicted to direct optimum expression of the attached gene, i.e. to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in alfalfa in particular, will be most preferred.

In one embodiment, the inventors contemplate that vectors comprising the promoters of the present invention may be constructed to include an enhancer element such as an ocs element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of plant transformation.

4.7 Process of Increasing Herbicide Resistance

Herbicides such as aryloxyphenoxypropionates and cyclohexane-1,3-dione derivatives inhibit the growth of monocotyledonous weeds by interfering with fatty acid biosynthesis of herbicide sensitive plants. ACCase is the target enzyme for those herbicides. Dicotyledonous plants, other eukaryotic organisms and prokaryotic organisms are resistant to those compounds.

Thus, the resistance of sensitive monocotyledonous plants to herbicides can be increased by providing those plants with ACCase that is not sensitive to herbicide inhibition. The present invention therefore provides a process of increasino the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a herbicide resistant polypeptide, a dicotyledonous plant polypeptide such as an acetyl-CoA carboxylase enzyme from soybean, rape, sunflower, tobacco, Arabidopsis, petunia, canola, pea, bean, tomato, potato, lettuce, spinach, alfalfa, cotton or carrot, or functional equivalent thereof. A promoter and a transcription-terminating region are preferably the same as set forth above.

Transformed monocotyledonous plants can be identified using herbicide resistance. A process for identifying a transformed monocotyledonous plant cell involves transforming the monocotyledonous plant cell with a DNA molecule that encodes a dicotyledonous acetyl-CoA carboxylase enzyme, and determining the resistance of the plant cell to a herbicide and thereby the identification of the transformed monocotyledonous plant cell. Means for transforming a monocotyledonous plant cell are the same as set forth above.

The inventors also contemplate that a similar strategy may be employed to develop new selectable markers for transformation of herbicide-sensitive plants, such as members of the Graminiae, including wheat, by using co-transformation of a desired gene and a herbicide-resistant ACCase, and selecting in the presence of the herbicide.

The resistance of a transformed plant cell to a herbicide is preferably determined by exposing such a cell to an effective herbicidal dose of a preselected herbicide and maintaining that cell for a period of time and under culture conditions sufficient for the herbicide to inhibit ACCase, alter fatty acid biosynthesis or retard growth. The effects of the herbicide can be studied by measuring plant cell ACCase activity, fatty acid synthesis or growth.

An effective herbicidal dose of a given herbicide is that amount of the herbicide that retards growth or kills plant cells not containing herbicide-resistant ACCase or that amount of a herbicide known to inhibit plant growth. Means for determining an effective herbicidal dose of a given herbicide are well known in the art. Preferably, a herbicide used in such a process is an aryloxyphenoxypropionate or cyclohexanedione herbicide.

4.8 Process of Altering ACCase Activity

ACCase catalyzes the carboxylation of acetyl-CoA. Thus, the carboxylation of acetyl-CoA in a cyanobacterium or a plant can be altered by, for example, increasing an ACCase gene copy number or changing the composition (e.g., nucleotide sequence) of an ACCase gene. Changes in ACCase gene composition may alter gene expression at either the transcriptional, translational, or post-translational level. Alternatively, changes in gene composition can alter ACCase function (e.g., activity, binding) by changing primary, secondary or tertiary structure of the enzyme. By way of example, certain changes in ACCase structure are associated with changes in the resistance of that altered ACCase to herbicides. The copy number of such a gene can be increased by transforming a yeast cell or a plant cell with an appropriate expression vector comprising a DNA molecule that encodes ACCase.

In one embodiment, therefore, the present invention contemplates a process of altering the carboxylation of acetyl-CoA in a cell comprising transforming the cell with a DNA molecule comprising a promoter operatively linked to a coding region that encodes a polypeptide having the ability to catalyze the carboxylation of acetyl-CoA, which coding region is operatively linked to a transcription-terminating region, whereby the promoter is capable of driving the transcription of the coding region in the host cell.

5. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should. in light of the present disclosure, appreciate that many changes can be made in the specific embodiments which are disclosed and still obtain a like or similar result without departing from the spirit and scope of the invention.

5.1 Example 1

Effects of Haloxyfop of Wheat Cytosolic ACCase

The effect of haloxyfop, one of the aryloxyphenoxypropionate herbicides has been tested, on the activity of ACCase from wheat germ and from wheat seedling leaves. For the in vitro assay of ACCase activity, 1–8 $\mu$l aliquots of ACCase preparations were incubated for 45 min at 37° C. with 20 $\mu$l of 100–200 mM KCl, 200 mM Tris-HCl pH 8.0, 10 mM MgCl$_2$, 2 mM ATP, 2 mM DTT, 2 mM $^{14}$C-NaHCO$_3$, and where indicated 1 mM Ac-CoA, in a final volume of 40 $\mu$l. The reaction was stopped by adding 4 $\mu$l of concentrated HCl 30–40 $\mu$l aliquots of the reaction mixture were spotted on filter paper and dried, and acid-stable radioactivity was measured using scintillation cocktail. Haloxyfop was added as the Tris salt of the acid, generously supplied by J. Secor of Dow-Elanco.

For the in vivo assay of ACCase activity, 2-week old seedlings of wheat (*Triticum aestivum* cv. Era) were cut about 1 cm below the first leaf and transferred to a 1.5 ml micro tube containing $^{14}$C-sodium acetate and haloxyfop (Tris salt) for 4–6 h. The leaves were then cut into small pieces and treated with 0.5 ml of 40% KOH for 1 h at 70° C., and then with 0.3 ml of $H_2SO_4$ and 20 μl of 30% TCA on ice. Fatty acids were extracted with three 0.5 ml aliquots of petroleum ether. The organic phase was washed with 1 ml of water. Incorporation of $^{14}$C-acetate into fatty acids is expressed as the percentage of the total radioactivity taken up by the seedlings. present in the organic phase.

As expected, the enzyme from wheat germ or from wheat chloroplasts was sensitive to the herbicide at very low levels. 50% inhibition occurs at about 5 and 2 μM haloxyfop, respectively. For comparison, the enzyme from pea chloroplasts is relatively resistant (50% inhibition occurs at >50:M haloxyfop). Finally, the in vivo incorporation of $^{14}$C-acetate into fatty acids in freshly cut wheat seedling leaves is even more sensitive to the herbicide (50% inhibition occurs at <1:M haloxyfop), which provides a convenient assay for both ACCase and haloxyfop.

5.2 Example 2
Cloning and Sequencing of Wheat Cytosolic ACCase cDNA
5.2.1 Materials and Methods
5.2.1.1 PCR™ Amplification Degenerate PCR™ primers were based on the alignment of amino acid sequences of the following proteins (accession numbers in brackets): rat (J03808) and chicken (J03541) ACCases; *E. coli* (M80458, M79446, X14825, M32214), Anabaena 7120 (L14862, L14863) and Synechococcus 7942 BCs and BCCPs; rat (M22631) and human (X14608) propionyl-coenzyme A carboxylase ("subunit): yeast (J03889) pyruvate carboxylase: *Propionibacterium shermanii* (M11738) transcarboxylase (1.3S subunit) and *Klebsiella pneutmonia* (J03885) oxaloacetate decarboxylase (a subunit). Each primer consisted of a 14-nucleotide specific sequence based on the amino acid sequence and a 6- or 8-nucleotide extension at the 5'-end.

Poly(A)$^+$ RNA from 8-day old plants (*Triticum aestivum* var. Era) was used for the synthesis of the first strand of cDNA with random hexamers as primers for AMV reverse transcriptase (Haymerle et al., 1986). Reverse transcriptase was inactivated by incubation at 90° C. and low molecular weight material was removed by filtration. All components of the PCR™ (Cetus/Perkin-Elmer), except the Taq DNA polymerase, were incubated for 3–5 min at 95° C. The PCR™ was initiated by the addition of polymerase. Conditions were optimized by amplification of the BC gene from Anabaena 7120. Amplification was for 45 cycles, each 1 min at 95° C., 1 min at 42–46° C. and 2 min at 72° C. $MgCl_2$ concentration was 1.5 mM. Both the reactions using Anabaena DNA and the single-stranded wheat cDNA as template yielded the expected 440-bp products. The wheat product was separated by electrophoresis on LMP-agarose and reamplified using the same primers and a piece of the LMP-agarose slice as a source of the template. That product, also 440-bp, was cloned into the Invitrogen vector pCR1000 using their A/T tail method, and sequenced.

In eukaryotic ACCases, the BCCP domain is located about 300 amino acids downstream from the end of the BC domain. Therefore, it was possible to amplify the cDNA encoding that interval between the two domains usinu primers, one from the C-terminal end of the BC domain and the other from the conserved biotinylation site. The expected 1.1-kb product of the first low yield PCR™ with primers III and IV was separated by electrophoresis on LMP-agarose and reamplified by another round of PCR™, then cloned into the Invitrogen vector pCRII® and sequenced. The PCR™ conditions were the same as those described above.

5.2.1.2 Isolation and Analysis of ACCase cDNA

A wheat cDNA library (*Triticum aestivum*, var. Tam 107, Hard Red Winter, 13-day light grown seedlings) was purchased from Clontech. This 8gt11 library was prepared using both oligo(dT) and random primers. Colony Screen-Plus® (DuPont) membrane was used according to the manufacturers' protocol (hybridization at 65° C. in 1 M NaCl and 10% dextran sulfate). The library was first screened with the 1.1-kb PCR™-amplified fragment of ACCase-specific cDNA. Fragments of clones 39-1, 45-1 and 24-3 were used in subsequent rounds of screening. In each case, ~2.5×10$^6$ plaques were tested. More than fifty clones containing ACCase-specific cDNA fragments were purified, and EcoRI fragments of the longest cDNA inserts were subcloned into pBluescriptSK® for further analysis and sequencing. A subset of the clones was sequenced on both strands by the dideoxy chain termination method with Sequenase® (United States Biochemicals) or using the Perkin Elmer/Applied Biosystems Taq DyeDeoxy Terminator cycle sequencing kit and an Applied Biosystems 373A DNA Sequencer.

5.2.1.3 RNA and DNA

Total RNA from 10-day old wheat plants was prepared as described in (Haymerle et al., 1986). RNA was separated on a glyoxal denaturing gel (Sambrook et al., 1989). Gene-Screen Plus® (DuPont) blots were hybridized in 1M NaCl and 10% dextran sulfate at 65° C. (wheat RNA and DNA) or 58–60° C. (soybean and canola DNA). All cloning, DNA manipulation and gel electrophoresis were as described (Sambrook et al., 1989).

5.2.2 Results
5.2.2.1 PCR™ Cloning of the Wheat (*Triticum Aestivum*) ACCase cDNA A 440-bp cDNA fragment encoding a part of the biotin carboxylase domain of wheat cytosolic ACCase and a 1.1-kb cDNA fragment encoding the interval between the biotin carboxylase domain and the conserved biotinylation site were amplified. These fragments were cloned and sequenced. In fact, three different 1.1-kb products, corresponding to closely related sequences that differ from each other by 1.5%, were identified. The three products most likely represent transcription products of three different genes, the minimum number expected for hexaploid wheat. These two overlapping DNA fragments (total length of 1473 nucleotides) wele used to screen a wheat cDNA library.

5.2.2.2 Analysis of Wheat Cytosolic ACCase cDNAs

A set of overlapping cDNA clones covering the entire ACCase coding sequence was isolated and a subset of these clones has been sequenced. The nucleotide sequence within overlapped regions of clones 39-1, 20-1 and 45–1 differ at 1.1% of the nucleotides within the total of 2.3 kb of the overlaps. The sequence within the overlap of clones 45-1 and 24-3 is identical. The sequence contains a 2257-amino acid reading frame encoding a protein with a calculated molecular mass of 251 kDa. In wheat gern the active ACCase has an apparent molecular mass of ~500 kDa and the individual polypeptides have an apparent molecular mass (measured by SDS-PAGE) of about 220 kDa (Gornicki and Haselkorn, 1993).

5.2.2.3 Northern Analysis of ACCase mRNA

Northern blots with total RNA from 10–14 day old wheat leaves were probed using different cDNA fragments (the 1.1-kb PCR™-amplified fragment and parts of clones 20-1, 24-3 and 01-4). In each case the only hybridizing mRNA species was 7.9 kb in size. This result shows clearly that all the cDNA clones correspond to mRNA of large, eukaryotic ACCase and that there are no other closely related biotin-dependent carboxylases, consisting of small subunits that are encoded by smaller mRNAs, in wheat.

Northern analysis of total RNA prepared from different sectors of 10-day old wheat seedlings indicates very high steady-state levels of ACCase-specific mRNA in cells of leaf sectors I and II near the basal meristem. The ACCase mRNA level is significantly higher in sectors I and II than in sectors III–VI. This cannot be explained by dilution of specific mRNA by increased levels of total RNA in older cells. Based on published results (Dean and Leech, 1982), the increase in total RNA between sectors I and VI is expected to be only about two-fold.

All cell division occurs in the basal meristem and cells in other sectors are in different stages of development. Differences between these young cells and the mature cells at the tip of the leaf include cell size, number of chloroplasts and amount of total RNA and protein per cell (Dean and Leech, 1982). Expression of some genes is correlated with the cell age. It is not surprising that the level of ACCase-specific mRNA is highest in dividing cells and in cells with increasing number of chloroplasts. The burst of ACCase mRNA synthesis is necessary to supply enough ACCase to meet the demand for malonyl-coenzyme A. The levels of ACCase mRNA decrease significantly in older cells where the demand is much lower. The same differences in the level of ACCase specific mRNA between cells in different sectors were found in plants grown in the dark and in plants illuminated for one day at the end of the dark period.

5.2.2.4 Southern Analysis of Plant DNA

Hybridization, under stringent conditions, of wheat total DNA digests with wheat cytosolic ACCase cDNA probes revealed multiple bands. This was expected due to the hexaploid nature of wheat (*Triticum aestivum*). Some of the wheat cDNA probes also hybridize with ACCase-specific DNA from other plants. The specificity of this hybridization was demonstrated by sequencing several fragments of canola genomic DNA isolated from a library using wheat cDNA probe 20-1 and by Northern blot of total canola RNA using one of the canola genomic clones as a probe. The Northern analysis revealed a large ACCase-specific messa (ge in canola RNA similar in size to that found in wheat.

5.2.2.5 ACCase mRNA

The putative translation start codon was assigned to the first methionine of the open reading frame. An in-frame stop codon is present 21 nucleotides up-stream from this AUG. The nucleotide sequence around this AUG fits quite well with the consensus for a monocot translation initiation site derived from the sequence of 93 genes, except for U at position +4 of the consensus which was found in only 3 of the 93 sequences. The ACCase mRNA stop codon UGA is also the most frequently used stop codon found in monocot genes, and the surrounding sequence fits the consensus well.

5.2.2.6 Lack of Targeting Sequence in Wheat Cytosolic ACCase cDNA

The wheat cDNA does not encode an obvious chloroplast targetingy sequence unless this is an extremely short peptide. There are only 12 amino acids preceding the first conserved amino acid found in all eukaryotic ACCases (a serine residue). The conserved core of the BC domain begins about 20 amino acids further down-stream. The apparent lack of a transit peptide poses the question of whether and how the ACCase described in this paper is transported into chloroplasts. It was shown recently that the large ACCase polypeptide purifies with chloroplasts of wheat and maize (Gornicki and Haselkorn, 1993; Egli et al., 1993). No obvious chloroplast transit peptide between the ER signal peptide and the mature protein was found in diatom ACCase either (Roessler and Ohlrogge, 1993).

The number of ACCase genes in wheat have been assessed by Southern analysis and by sequence analysis of the 5'- and 3'-untranslated portions of ACCase cDNA representing transcripts of different genes. These cDNA fragments may be obtained by PCR™ amplification using the 5'- and 3'-RACE methodology. The genome structure of wheat (*Triticum aestivum*) suggests the presence of at least three copies of the ACCase gene, i.e. one in each ancestral genome. Sequence analysis of the 5'-untranscribed parts of the gene may determine whether any familiar promoter and regulatory elements are present. The structure of introns within the control region and in the 5'-fragment of the coding sequence is also of interest.

The plant ACCase genes are full of introns and their transcripts undergo alternative splicing. In some plant genes, introns have been found both within the sequence encoding the transit peptide, and at the junction between the transit peptide and the mature protein.

5.3 Example 3

DNA Compositions Encoding a Wheat Cytosolic ACCase

This example describes the cloning and DNA sequence of the entire gene encoding wheat (var. flard Red Winter Tam 107) acetyl-CoA carboxylase (ACCase). Comparison of the 12-kb genomic sequence with the 7.4-kb cDNA sequence reported in Example 2 revealed 29 introns. Within the coding region, the exon sequence is 98% identical to the wheat cDNA sequence. A second ACCase gene was identified by sequencing fragments of genomic clones that include the first two exons and the first intron. Additional transcripts were detected by 5'- and 3'-RACE analysis. One set of transcripts had 5'-end sequence identical to the cDNA found previously and another set was identical to the gene reported here. The 3'-RACE clones fall into four distinguishable sequence sets, bringing the number of ACCase sequences to six. None of these cDNA or genomic clones encode a chloroplast targeting signal. Identification of six different sequences suggests that either the cytosolic ACCase genes are duplicated in the three chromosome sets in hexaploid wheat or that each of the six alleles of the cytosolic ACCase gene has a readily distinguishable DNA sequence.

5.3.1 Materials and Methods 5.3.1.1 Isolation and Analysis of ACCase Genomic Clones A wheat genomic library (*T. aestivum*, var. Hard Red Winter Tam 107, 13-day light grown seedlings) was purchased from Clontech. This λ EMBO3 library was prepared from genomic DNA partially digested with Sau3A. Colony ScreenPlus (DuPont) membrane was used according to the manufacturers' protocol (hybridization at 65° C. in 1M NaCl and 10% dextran sulfate). The library was screened with a 440-bp PCR™-amplified fragment of ACCase-specific cDNA and with cDNA clone 24-3 (Gornicki et al., 1994). In each case, ~1.2×10$^6$ plaques were tested. 24 clones containing ACCase-specific DNA fragments were purified and mapped. Selected restriction fragments of these genomic clones were subcloned into pBluescriptSK® for further analysis and sequencing. The 3'-terminal fragment of the gene (clone 145) was amplified by PCR™ using wheat genomic DNA as a template. Primers were based on the sequence of genomic clone 233:

5'-CGCTATAGGGAAACGTTAGAAGGATGGG-3' (SEQ ID NO:10) and 3'-RACE clone 4:

5'-ATCGATCGGCCTCGGCTCCAATTTCATT-3' (SEQ ID NO:11).

All PCR™ components except Taq polymerase were incubated for 5 min. at 95° C. The reactions were initiated by the addition of the polymerase followed by 35 cycles of incubation at 94° C. for 1 min, 55° C. for 2 min and 72° C. for 2 min. A 1.8-kb PCR™ product was gel-purified, reamplified using the same primers, cloned into the Invitrogen vector pCRII™ and sequenced.

5.3.1.2 Analysis of mRNA by Rapid Amplification of cDNA Ends (RACE)

Two sets of 15 and 20 cDNA fragments corresponding to mRNA 5'- and 3'-ends, respectively, were prepared by T/A cloning of RACE products into the vector pCRII. Total RNA from 15-day old wheat (*Triticum aestivum* var. Tam 107, Hard Red Winter) plants was prepared as described in Chirgwin et al. (1979). A Gibco BRL 5'-RACE kit was used according to the manufacturers' protocol. For the 5'-end amplification, the first strand of cDNA was prepared using a gene-specific primer:

5'-GTTCCCAAAGGTCTCCAAGG-3' (SEQ ID NO:12);

followed by the addition of a homopolymeric dA-tail. dT-Anchor primer:

5'-GCGGACTCGAGTCGACAAGCTTTTTTTTTTTT-TTTT-3' (SEQ ID NO:13)

and a gene-specific primer,

5'-ACGCGTCGACTAGTAGGTGCGGATGCTGCGCA-TG-3' (SEQ ID NO:14)

were used in the first round of PCR™.

Universal primer,

5'-GCGGACTCGAGTCGACAAGC-3' (SEQ ID NO:15)

and another gene-specific primer,

5'-ACGCGTCGACCATCCCATTGTTGGCAACC-3' (SEQ ID NO:16)

were used for reamplification. The gene-specific primers were targeted to a stretch of 5'-end coding sequence identical in clones 39 and 71 that were available.

Clone 71 was isolated from a 8gt11 cDNA library using a fragment of cDNA 39 as probe. The same dT-anchor primer and universal primer together with a gene specific primer

5'-GACTCATTGAGATCAAGTTC-3' (SEQ ID NO:17)

were used for the first strand cDNA synthesis and 3'-end amplification. The latter primer was targeted to the 3'-end of the ACCase open reading frame.

All cloning, DNA manipulations and gel electrophoresis were as described (Sambrook et al., 1989). DNA was sequenced on both strands by the dideoxy chain termination method using $^{35}$S-[dATP] with Sequenase (United States Biochemicals) or using the Perkin Elmer/Applied Biosystems Taq DyeDeoxy Terminator cycle sequencing kit and an Applied Biosystems 373A DNA Sequencer.

5.3.2 Results 5.3.2.1 Analysis of Wheat Cytosolic ACCase Genes

Two cDNA fragments, one encoding a part of the biotin carboxylase domain of wheat cytosolic ACCase and the other a part of the carboxyltransferase, were used to isolate a set of overlapping DNA fragments covering the entire ACCase gene. Where they overlap, the nucleotide sequences of clones 31, 191 and 233 are identical. These obviously derive from the same gene. cDNA clone 71 represents the transcription product of this gene (430-nucleotide identical sequence). The sequence of clone 145 obtained by PCR™ to cover the remaining 3'-end part of the gene differs from clone 233 by 5 of 400 nucleotides of the overlap located within the long exon 28. It must therefore derive from a different copy of the ACCase gene. 3'-RACE clone 4 (3'-4, see below) differs at 6 of 490 nucleotides in the overlap.

The sequence was deposited in GenBank (as accession number U39321), and is a composite of these three very closely related sequences. Its 5'-end corresponds to the 5'-end of clone 71 and the 3'-end corresponds to the poly(A) attachment site of the 3'-RACE clone 4. It was assumed that no additional introns are present at the very end of the gene.

Comparison of the genomic sequence with the cDNA sequence in Example 4 revealed 29 introns. Intron location is conserved among all three known plant ACCase genes except for two introns not present in wheat but found in rape (Schulte et al., 1994), *A. thaliana* (Roesler et al., 1994) and soybean (Anderson et al., 1995). The nucleotide sequence at splice sites fits well with the consensus for monocot plants. The A+T content of the gene exons and introns is 52% and 63%, respectively, compared to 42% and 61% found for other monocot plant genes (White et al., 1992). The exon coding sequence is 98% identical to that of the eDNA sequence reported earlier. This is the same degree of identity as found previously for different transcripts of the cytosolic ACCase genes in hexaploid wheat. The 11-amino acid sequence obtained previously for a CNBr-generated internal fragment of purified 220-kDa wheat germ ACCase (Gornicki and Haselkorn, 1993) differs from the sequence encoded by these cDNA and genomic clones at one position, but it is identical with the corresponding cDNA sequence of the plastid ACCase from maize (Egli et al., 1995), excluding one amino acid which could not be assigned unambiguously in the sequence.

Two additional genomic clones, 153 and 23 1, were also partially sequenced. The sequenced fragments include parts of the first two exons and the first intron. Although cDNA corresponding exactly to genomic clone 153 is not available, the boundaries of the first intron could easily be identified by sequence comparison with cDNA clone 71 (corresponding to genomic clone 31). Clone 153 encodes a polypeptide that differs by only one out of the first 110 amino acids of the ACCase open reading frame. The sequence of the 5'-leader was also well conserved but the 5'-part of the First intron of clone 153 is significantly different from that of genomic clone 31.

On the other hand, only the 3'-splice site of an intron could be identified by sequence comparison in this part of clone 231. The sequence immediately upstream of the 3'-splice site and that of the following exon is identical to that of clone 31. No sequence related to that found upstream of the first intron of clone 191 could be identified in clone 231 by hybridization (including a ~6 kb fragment upstream of the ACCase open reading frame) or by sequencing (~2 kb of the upstream fragment). It is possible that the first intron in this gene is much larger (additional upstream introns can not be excluded) or that the upstream exon(s) and untranscribed part of the gene has a completely different sequence. A cloning artifact can not be ruled out. Indeed clone 31 contained such an unrelated sequence at its 5'-end (probably a ligation artifact).

Identification of three additional genomic clones with sequence closely related to the other ACCase genes but containing no introns at several tested locations suggests the existence of a pseudogene in wheat. It is 93% and 96% identical with clone 233 at the nucleotide and amino acid level, respectively.

5.3.2.2 Analysis of mRNA Ends

In the original library screen (Gornicki et al., 1994) it was not possible to isolate any cDNA clones corresponding to the very ends of the ACCase mRNA. With the new sequence available it became possible to generate the missing pieces by RACE. Two sets of 5'-end RACE clones, 71L and 39L, were identified. Their sequence is identical to the sequence of cDNA clones 71 (this work) and 39 (Gornicki et al., 1994), respectively. The two sequences extend 239 and 312 nucleotides upstream of the ACCase initiation codon and define an approximate position of the transcription start site. None of the genomic clones corresponds to 39L. The presence of the first intron in the corresponding gene could not therefore be confirmed. All three coding sequences are very similar (they differ by only one three-amino acid deletion or one E to D substitution found within the first 110 amino acids) and none of them encodes additional amino acids at the N-terminus, i.e., none of them encodes a potential chloroplast transit peptide.

The sequences of the 5'-leaders differ significantly although they share some distinctive structural features. They are relatively long) (at least 239–312 nucleotides as indicated by the lengths of 39L and 71L, respectively), G+C rich (67%) and contain upstream AUG codons. The open reading frames found in the leaders are 70–90 amino acids long and they end within a few nucleotides of the ACCase initiation codon. A similar arrangement was found in the sequence of genomic clone 153. The three upstream AUG codons are conserved and the presence of deletions, most of which are a multiple of three nucleotides, suggests at least some conservation of the open reading frames at the amino acid level.

This arrangement, found in the cytosolic ACCase genes, contrasts with the majority of 5'-untranslated leaders found in plants. Although much longer leader sequences containing upstream AUG codons have been reported in plants (e.g., Shorrosh et al., 1995), they are rare. In most cases, the first AUG codon is the site of initiation of translation of the major gene product. The upstream AUGs are believed to affect the efficiency of mRNA translation and as such may be important in the regulation of expression of some genes (Roesler et al., 1994; Anderson et al., 1995). They are often found in mRNAs encoding transcription factors, growth factors and receptors, all important regulatory proteins (Kozak, 1991). They are also found in some plant mRNAs encoding heat shock proteins (Joshi and Nguyen, 1995). The ~800 nucleotide long leader intron found in both genes (clones 153 and 191) may also be important for the level and pattern of gene expression (e.g., Fu et al., 1995).

Four different sequences and two different polyadenylation sites ~300 and ~500 nucleotides downstream of the translation stop codon, respectively, were detected among the 3'-end RACE clones. The sequence of the cDNA reported previously (Gornicki et al., 1994) and the sequence of genomic clone 145 are also different in this region, bringing the total number of different sequences to six. 3–14 nucleotide differences were found in pairwise comparisons among these six sequences within two stretches that include 282 nucleotides at the 5'-end of the 3'-RACE clones and 204 nucleotides at the 3'-end.

5.3.2.3 Cytosolic ACCase

A gene encoding eukaryotic-type cytosolic ACCase from wheat was cloned and sequenced. Nucleotide identity between the cDNA and the gene within the coding sequence is 98%. The putative translation start codon was assigned in the original cDNA sequence to the first methionine of the open reading frame. An in-frame stop codon is present 21 nucleotides upstream from this AUG and the conserved core of the biotin carboxylase domain begins about 20 amino acids further down-stream. The gene encodes a 2260-amino acid protein with a calculated molecular mass of 252 kDa. The wheat cDNA did not encode an obvious chloroplast targeting sequence. The same is true for all the cDNA and genomic sequences described in this paper. The cDNA for maize plastid ACCase, reported recently (Egli et al., 1995), does encode a chloroplast transit peptide.

Comparison of the ACCase sequence encoded by the gene reported in this paper with the sequence of other representative biotin-dependent carboxylases is shown in Table 2. Wheat cytosolic ACCase is most similar to other eukaryotic-type plant ACCases. Identity with other eukaryotic carboxylases is also significant. The core sequence of the most conserved ACCase domain, biotin

TABLE 2

AMINO ACID IDENTITIES (%) BETWEEN *T. AESTIVUM* CYTOSOLIC ACCASE AND SOME OTHER REPRESENTATIVE BIOTIN-DEPENDENT CARBOXYLASES

| Specimen | Location | Full Length | Biotin Carboxylase Domain | References |
|---|---|---|---|---|
| Eukaryotic type carboxylases | | | | |
| *T. aestivum*[1] | cytosolic | 99 | 99 | Gornicki et al., 1994 |
| *A. thaliana* | cytosolic | 72 | 87 | Roesler et al., 1994 |
| *M. sativa* | cytosolic | 73 | 86 | Shorrosh et al., 1994 |
| *B. napus*[2] | | 68 | 82 | Schulte et al., 1994 |
| *Z. mays* | plastid | 71 | 81 | Egli et al., 1995 |
| *R. ratus* | cytosolic | 40 | 59 | Lopez-Casillas et al., 1988 |
| *C. cryptica*[2] | | 38 | 55 | Roessler and Ohlrogge, 1993 |
| *S. cerevisiae* | cytosolic | 40 | 56 | Al-Feel et al., 1992 |
| Prokaryotic type carboxylases | | | | |
| *E. coli*[3] | bacterial | — | 33 | Li and Cronan, 1992 |
| Anabaena 7120[3] | bacterial | — | 34 | Gornicki et al., 1993 |
| *M. leprae*[4] | bacterial | — | 32 | Norman et al., 1994 |
| *N. tabacum*[3] | plastid | — | 32 | Shorrosh et al., 1995 |
| *R. ratus* PCC[5] | mitochondrial | — | 34 | Browner et al., 1989 |
| *S. cerevisiae* PC[6] | mitochondrial | — | 32 | Lim et al., 1988 |
| *A. thaliana* MCCase[7] | mitochondrial | — | 34 | Weaver et al., 1995 |

[1]Sequence deduced from cDNA sequence reported previously (product of a different allele or gene).
[2]Cellular localization uncertain.
[3]Biotin carboxylase subunit of ACCase.
[4]Biotin carboxylase-biotin carboxyl carrier subunit of ACCase.
[5]Biotin carboxylase-biotin carboxyl carrier subunit (a) of propionyl-CoA carboxylase.
[6]Pyruvate carboxylase.
[7]Biotin carboxylase-biotin carboxyl carrier subunit of methylcrotonyl-CoA carboxylase.

carboxylase, is well conserved in both eukaryotic and prokaryotic biotin-dependent carboxylases. The other functional domains are less conserved. Among plant eukaryotic-type ACCases, the wheat cytosolic ACCase is no more similar to the maize plastid ACCase (both monocots) than it is to cytosolic ACCases from dicot plants. Clearly, cytosolic and plastid eukaryotic-type ACCases are quite distinct proteins. Another wheat cytosolic ACCase for which partial sequence is available (Elborough et al., 1994) is most likely a plastid isozyme. It is more similar to the maize plastid ACCase than to the wheat cytosolic enzyme. The plant prokaryotic-type plastid enzyme is more similar to bacterial, most notably cyanobacterial ACCases and to biotin-dependent carboxylases found in mitochondria, than to any of the plant cytosolic ACCases.

Sequence comparison of fragments of cl)NA and genomic clones from the 3'-end of the gene brings the total number of different genes encoding cytosolic ACCase in wheat to six, indicating that in hexaploid wheat there are at least two distinguishable coding sequences for the cytosolic ACCase in each of the three ancestral chromosome sets. Those two sequences might correspond to the alleles of the ACCase gene present in each ancestral chromosome set. On the other hand, it is possible that each pair of alleles has identical sequences, since the bread wheat studied is extensively inbred. If that is the case, then one or more ancestral genes has been duplicated.

5.4 Example 4

Developmental Analysis of ACCase Genes

Methods have been developed for analyzing the regulation of ACCase gene expression on several levels. With the cDNA clones in hand, the first may be obtained by preparing total RNA from various tissues at different developmental stages e.g., from different segments of young wheat plants, then probing Northern blots to determine the steady-state level of ACCase mRNA in each case. cDNA probes encoding conserved fragments of ACCase may be used to measure total ACCase mRNA level and gene specific probes to determine which gene is functioning in which tissue.

In parallel, the steady-state level of ACCase protein (by western analysis using ACCase-specific antibodies and/or using labeled streptavidin to detect biotinylated peptides) and its enzymatic activity may be measured to identify the most important stages of synthesis and reveal mechanisms involved in its regulation. One such study evaluates ACCase expression in fast growing leaves (from seedlings at different age to mature plants), in the presence and in the absence of light.

5.5 Example 5

Isolation of Herbicide-Resistant Mutants

Development of herbicide-resistant plants is an important aspect of the present invention. The availability of the wheat cDNA sequence facilitates such a process. By insertion of the complete ACCase cDNA sequence into a suitable yeast vector in place of the yeast ACCase coding region, it is possible to complement an ACC1 mutation in yeast using procedures well-known to those of skill in the art (see e.g., Haslacher et al., 1993). Analysis of the function of the wheat gene in yeast depends first on tetrad analysis, since the ACC1 mutation is lethal in homozygotes.

Observation of four viable spores from ACC1 tetrads containing the wheat cytosolic ACCase gene may confirm that the wheat gene functions in yeast, and extracts of the complemented ACC1 mutant may be prepared and assayed for ACCase activity. These assays may indicate the range of herbicide sensitivity, and in these studies, haloxyfop acid and clethodim may be used as well as other related herbicide compounds.

Given that the enzyme expressed in yeast is herbicide-sensitive, the present invention may be used in the isolation of herbicide-resistant mutants. If spontaneous mutation to resistance is too infrequent, chemical mutagenesis with DES or EMS may be used to increase such frequency. Protocols involving chemical mutagenesis are well-known to those of skill in the art. Resistant mutants, i.e., strains capable of growth in the presence of herbicide, may be assayed for enzyme activity in vitro to verify that the mutation to resistance is within the ACCase coding region.

Starting with one or more such verified mutants, several routes may lead to the identification of the mutated site that confers resistance. Using the available restriction map for the wild-type cDNA, chimeric molecules may be constructed containing half, quarter and eighth fragments, etc. from each mutant, then checked by transformation and tetrad analysis whether a particular chimera confers resistance or not.

Alternatively a series of fragments of the mutant DNA may be prepared, end-labeled, and annealed with the corresponding wild-type fragments in excess, so that all mutant fragments are in heterozygous molecules. Brief S1 or mung bean nuclease digestion cuts the heterozygous molecules at the position of the mismatched base pair. Electrophoresis and autoradiography is used to locate the position of the mismatch within a few tens of base pairs. Then oligo-primed sequencing of the mutant DNA is used to identify the mutation. Finally, the mutation may be inserted into the wild-type sequence by oligo-directed mutagenesis to confirm that it is sufficient to confer the resistant phenotype.

Having identified one or more mutations in this manner the corresponding parts of several dicot ACCase genes may be sequenced (using the physical maps and partial sequences as guides) to determine their structures in the corresponding region, in the expectation that they are now herbicide resistant.

5.6 Example 6

Analysis of Canola ACCase cDNA

Wheat cytosolic ACCase cDNA probes were used to detect DNA encoding canola ACCase. Southern analysis indicated that a wheat probe hybridizes quite strongly and cleanly with only a few restriction fragments that were later used to screen canola cDNA and genomic libraries (both libraries provided by Pioneer HiBred Co [Johnson City, Iowa]). About a dozen positive clones were isolated from each library.

Sequence analysis was performed for several of these genomic clones. Fragments containing both introns and exons were identified. One exon sequence encodes a polypeptide which is 75% identical to a fragment of wheat cytosolie ACCase. This is very high conservation especially for this fragment of the ACCase sequence which is not very conserved in other eukaryotes. One of the other genomic clones (6.5 kb in size) contains the 5' half of the canola gene, and additional screening of the genomic library may produce other clones which contain the promoter and other potential regulatory elements.

5.7 Example 7

Methods for Obtaining ACCase Mutants

In *E. coli*, only conditional mutations can be isolated in the ACCase genes. The reason is that although the bacteria can replace the fatty acids in triglycerides with exogenously provided ones, they also have an essential wall component called lipid A, whose β-hydroxy myristic acid can not be supplied externally.

One aspect of the present invention is the isolation of Anacystis mutants in which the BC gene is interrupted by an antibiotic resistance cassette. Such techniques are well-known to those of skill in the art (Golden et al., 1987). Briefly, the method involves replacing the cyanobacterial ACCase with wheat ACCase, so it is not absolutely necessary to be able to maintain the mutants without ACCase. The wheat ACCase clone may be introduced first and then the endogenous gene can be inactivated without loss of viability.

By replacing the endogenous herbicide resistant ACCase in cyanobacteria with the wheat cDNA, resulting cells are sensitive to the herbicides haloxyfop and clethodim, whose target is known to be ACCase. Subsequently, one may isolate mutants resistant to those herbicides. These methods are known to those of skill in the art (Golden et al., 1987).

The transformation system in Anacystis makes it possible to pinpoint a very small DNA fragment that is capable of conferring herbicide resistance. DNA sequencing of wild type and resistant mutants then reveals the basis of resistance.

Alternatively, gene replacement may be used to study wheat ACCase activity and herbicide inhibition in yeast. Mutants may be selected which overcome the normal sensitivity to herbicides such as haloxyfop. This will yield a variant(s) of wheat ACCase that are tolerant/resistant to the herbicides. The mutated gene (cDNA) present on the plasmid can be recovered and analyzed further to define the sites that confer herbicide resistance. As for the herbicide selection, there is a possibility that the herbicide may be inactivated before it can inhibit ACCase activity or that it may not be transported into yeast. There are general schemes for treatment of yeast with permeabilizing antibiotics at sublethal concentrations, which are known to those of skill in the art. Such treatments allow otherwise impermeable drugs to be used effectively. For these studies haloxyfop acid and clethodim may be used.

Characterization of the site(s) conferring herbicide resistance generally involves assaying extracts of the complemented ACC1 mutant for ACCase activity. Both spontaneous mutation and chemical mutagenesis with DES or EMS, may be used to obtain resistant mutants, i.e., strains capable of growth in the presence of herbicide. These may be assayed for enzyme activity in vitro to verify that the mutation to resistance is within the ACCase coding region. Starting with one or more such verified mutants, the mutated site that confers resistance may be analyzed. Using the available restriction map for the wild-type cDNA, chimeric molecules may be constructed which containing half, quarter and eighth fragments, etc., from each mutant, and then checked by transformation and tetrad analysis to determine whether a particular chimera confers resistance or not.

An alternative method involves preparing, a series of fragments of the mutant DNA, end-labeling, and annealing with the corresponding wild-type fragments in excess, so that all mutant fragments are in heterozygous molecules. Brief S1 or mung bean nuclease digestion cuts the heterozygous molecules at the position of the mismatch within a few tens of base pairs. Then oligo-primed sequencing of the mutant DNA is used to identify the mutation. Finally, the mutation can be inserted into the wild-type sequence by oligo-directed mutagenesis to confirm that it is sufficient to confer the resistant phenotype. Having identified one or more mutations in this manner, the corresponding parts of several dicot ACCase genes to determine their structures in the corresponding region, in the expectation that they would be "resistant".

5.8 Example 8

Preparation of ACCase-Specific Antibodies

Another aspect of the present invention is the preparation of antibodies reactive against plant ACCase for use in immunoprecipitation, affinity chromatography, and immunoelectron microscopy. The antisera may be prepared in rabbits, using methods that are well-known to those of skill in the art (see e.g., Schneider and Haselkorn, 1988).

Briefly, the procedure encompasses the following aspects. Gel-purified protein is electroeluted, dialyzed, mixed with complete Freund's adjuvant and injected in the footpad at several locations. Subsequent boosters are given with incomplete adjuvant and finally with protein alone. Antibodies are partially purified by precipitating lipoproteins from the serum with 0.25% sodium dextran sulfate and 80 mM $CaCl_2$. Immunoglobulins are precipitated with 50% saturating ammonium sulfate, suspended in phosphate-buffered saline at 50 mg/ml and stored frozen. The antisera prepared as described may be used in Western blots of protein extracts from wheat, pea, soybean, canola and sunflower chloroplasts as well as total protein.

5.9 Example 9

Protein Fusions, Transgenic Plants and Transport Mutants

Analysis of promoter and control elements with respect to their structure as well as tissue specific expression, timing etc., is performed using promoter fusions (e.g. with the GUS gene) and appropriate in situ assays. Constructs may be made which are useful in the preparation of transgenic plants.

For identifying transport of ACCase, model substrates containing different length N-terminal fragments of ACCase may be prepared by their expression (and labeling) in *E. coli* or by in vitro transcription with T7 RNA polymerase and translation (and labeling) in a reticulocyte lysate. Some of the model substrates will include the functional biotinylation site (located ~800 amino acids from the N-terminus of the mature protein; the minimum biotinylation substrate will be defined in parallel) or native ACCase epitope(s) for which antibodies will be generated as described above. Adding an antibody tag at the C-terminus will also be very helpful. These substrates will be purified by affinity chromatography (with antibodies or streptavidin) and used for in vitro assays.

For modification of ACCase protein transport, model substrates consisting of a transit peptidc (or any other chloroplast targeting signals) to facilitate import into chloroplasts, fused to different ACCase domains that are potential targets for modification, may be used. Modified polypeptides from cytoplasmic and/or chloroplast fractions will be analyzed for modification. For example, protein phosphorylation (with $^{32}P$) can be followed by immunoprecipitation or by PAGE. Antibodies to individual domains of ACCase may then be employed. The same experimental set-up may be employed to study the possible regulation of plant ACCase by phosphorylation (e.g., Witters and Kemp, 1992). Biotinylation may be followed by Western analysis using $^{35}S$-streptavidin for detection or by PAGE when radioactive biotin is used as a substrate.

5.10 Example 10

Expression Systems for Preparation of ACCase Polypeptides

The entire plant ACCase cDNA and its fragments, and BC, BCCP and the CT gene clones from cyanobacteria may be used to prepare large amounts of the corresponding proteins in *E. coli*. This is most readily accomplished using the T7 expression system. As designed by Studier, this expression system consists of an *E. coli* strain carrying the gene for T7 lysozyme and for F7 RNA polymerase, the latter controlled by a lac inducible promoter. The expression vector with which this strain can be transformed contains a promoter recognized by T7 RNA polymerase, followed by a multiple cloning site into which the desired gene can be inserted (Ashton et al., 1994).

Prior to induction, the strain grows well, because the few molecules of RNA polymerase made by basal transcription from the lac promoter are complexed with T7 lysozyme. When the inducer IPTG is added, the polymerase is made in excess and the plasmid-borne gene of interest is transcribed abundantly from the late T7 promoter. This system easily makes 20% of the cell protein the product of the desired gene. A benefit of this system is that the desired protein is often sequestered in inclusion bodies that are impossible to dissolve after the cells are lysed. This is an advantage in the present invention, because biological activity of these polypeptides is not required for purposes of raising antisera. Moreover, other expression systems are also available (Ausubel et al., 1989).

5.11 Example 11

Yeast Expression Systems

In yeast, a single ACC1 gene encodes an ACCase that provides malonyl-CoA for both de novo fatty acid synthesis as well as for subsequent fatty acid elongation. A null mutation of ACC1 is not rescued by fatty acid supplementation, suggesting an additional essential function for ACCase in yeast (Haslacher et al., 1993). This function has recently been identified as providing malonyl-CoA for the biosynthesis of very-long-chain fatty acids that are required to maintain a functional nuclear envelope (Schneiter et al., 1996).

Interaction with aryloxyphenoxypropionate and cyclohexanedione inhibitors is an important aspect of plant ACCase biochemistry (Golz et al., 1994; Holt et al., 1993; Konishi and Sasaki, 1994). Some of these compounds are used as powerful graminicides. The herbicide action is caused by the inhibition of the eukaryotic-type plastid ACCase and as a result inhibition of fatty acid biosynthesis in sensitive plants. Plants containing prokaryotic-type plastid ACCase are resistant to these compounds, as are other eukaryotes and prokaryotes. The molecular mechanism of inhibitioni/resistance of the enzyme is not known.

The inventors have shown previously that wheat plastid ACCase is highly sensitive to an aryloxyphenoxypropionate inhibitor (haloxyfop) (Gornicki and Haselkorn 1993) but the corresponding cytosolic enzyme could not be studied effectively. Ihe inventors have recently obtained full length cDNA and genomic sequences for both cytosolic and plastid ACCases from wheat (Gornicki et al., 1994; Podkowinski et al., 1996. This example describes the establishment of yeast expression systems that allow investigation of the structure and function, including interaction with inhibitors, of individual wheat ACCases.

5.11.1 Materials and Methods 5.15.1.1 Assembling a Chimeric Gene

Full length cDNA encoding wheat cytosolic ACCase was assembled in a multi-step "cut and paste" cloning study. The assembly process was monitored by sequencing selected regions of the construct. Restriction fragments from cDNA clones described before (Gornicki et al., 1994) as well as PCR™-generated fragments with new restriction sites were used for the construction. The chimeric gene (gyccwy, FIG. 1A) consists of the following eight fragments inserted in this order between BamHI and SalI sites of pRS423 or pRS424 (Christianson et al., 1992): 1) BamHI-EcoRI fragment containing GAL10 promoter from pBM150 (Johnston and Davis, 1984); 2) EcoRI-NcoI fragment containing the leader sequence of the ACC1 gene from S. cerevisiae (Haslacher et al., 1993) prepared by PCR™ to introduce a NcoI site at the translational start codon; 3) NcoI-XbaI fragment of clone 39-1 for which a sub-fragment was prepared by PCR™ to introduce NcoI site at the ACCase translation start codon; 4) XbaI-SphI fragment of clone 20-1; 5) SphI-BamHI fragment of clone 45-1; 6) BamHI-EcoRI fragment of clone 24-3; 7) EcoRI-BamHI fragment of clone 01-4; 8) BamHI-SalI fragment consisting of 17 nucleotides of wheat cytosolic ACCase cDNA (sequence identical to clone 01-4 (Gornicki et al., 1994)), 277 nucleotides of the yeast ACC1 gene containing the 3'-tail, 24 nucleotides of the pRS426 vector followed by a SalI site. This fragment was prepared by PCR™ using pRS426-ACC1 (below) as template. A 7969 bp SacI fragment of yeast genomic DNA from plasmid YCp50-ACC1 (Haslacher et al., 1993), obtained from Dr. S. D. Kohlwein (Technical University Graz. Austria), containing the ACC1 gene was cloned into the SacI site of vector pRS426 to create pRS426-ACC1. The 5'-end of the ACC1 gene in this construct is adjacent to the KpnI site of the vector.

5.11.1.2 Yeast Transformation, Growth and Tetrad Analysis

The yeast complex medium for vegetative growth contained 1% Bacto-yeast extract, 2% Bacto-peptone, 0.1% adenine sulfate and was supplemented with the following carbon sources: 2% Dextrose in YPD, 2% Raffinose in YPR, 2% galactose and 2% raffinose in YPRG. The yeast synthetic minimal medium (SD) contained 0.17% yeast nitrogen base, 0.5% ammonium sulfate, 2% dextrose, and was supplemented with various additives required for growth: adenine sulfate (10 mg/L), uracil (20 mg/L), histidine (20 mg/L), leucine (200 mg/L) and/or tryptophane (50 mg/L). The SRG medium is identical to SD, with dextrose replaced by 2% raffinose and 2% galactose. 2% bacto-agar was used in solid media. SPII (2% potassium acetate, supplemented with essential amino acids at 7.5 mg/L) and SPIII (0.1% bactoyeast extract and 2% bacto-agar added to SPII) media for sporulation are described in (Klapholz and Esposito, 1982; Klapholz et al;. 1985). S. cerevisiae strain W303D-ACC1$^{\Delta LEU2}$ was also obtained from Dr. S. D. Kohlwein. Yeast cells were transformed as described before (Chen et al., 1992) using Frozen-ELZ kit (Zymo Research, Orange Calif.) according to the manufacturer's protocol and transformants were selected using SD plates lacking a marker amino acid. Sporulation was induced in SPII or SPIII medium at 30° C. for 2–3 days. Dissection of asci was performed as described (Guthrie and Fink, 1991). YPD or YPRG plates were used for vegetative growth of ascospore clones following dissection. Galactose-dependent strains (MJ 6.8, 6.9, 1.12 and 1.13) were grown in YPRG medium and other strains in YPD medium, all at 30° C. To measure galactose induction, the strains were grown for ~24 h in YPR medium until all galactose was exhausted (growth of galactose-dependent strains ceased), and then diluted ~100 fold with YPR medium containing various amounts of galactose.

5.11.1.3 In Vivo and In Vitro Herbicide Inhibition

Sethoxydim and Cethoxydim (CGA215684) were obtained from CIBA-GEIGY and haloxyfop was obtained from DowElanco. The inhibitor structures are shown in FIG. 1B. To measure inhibition in vivo, galactose-dependent strains were grown in YPR containing 0.01% galactose (to $A_{600}$ of ~0.5) and then diluted (~100 fold) to the same initial density with fresh YPR medium containing 0.01% galactose and varying amounts of herbicide added as 100-fold concentrated stock solutions in DMSO. ACCase activity in vitro was measured using protein extracts prepared as described (Mitchell et al., 1993) from 25–50 ml cultures of yeast strains MJ 1.12 and MG 9.11 grown for 24–40 h. Cells were suspended in one volume of extraction buffer (0.3 M sorbitol, 0.1 M NaCl, 5 mM MgCl$_2$, 10 mM Tris pH 7.4, supplemented with protease inhibitors: aprotinin (6.6 $\mu$/mL), leupeptin (1.5 $\mu$/mL), pepstatin A (3 $\mu$/mL) and chymostatin (1 $\mu$g/mL), and vortexed with 2 volumes of glass beads for 5 min at 4° C. 1/200 volume of 100 mM ethanol solution of phenylmethylsulfonyl fluoride was added twice during extraction. The cell debris were removed by centrifugation and the supenatant (~0.5 ml) was loaded immediately on a 20 ml Sephadex G50 column equilibrated with 100 mM KCl, 20 mM Tris/HCl (pH 7.5), 20% glycerol, 7 mM β-mercaptoethanol. Protein was eluted with the same buffer and stored at −70° C. ACCase activity was measured as described before (Gornicki and Haselkorn, 1993) using aliquots of the column fractions. Herbicides were added to the reaction mixtures (1/10 or 1/20 volume) as a solution in 0.25–0.75 M Tris-HCl, pH8.0 containing 25% DMSO. Wheat germ extract was purchased from Promega.

5.11.1.4 DNA and Protein Anaylsis

DNA and protein manipulations and analyses were performed as described in (Sambrook et al., 1989) or following manufacturer's protocols. DNA was isolated from yeast as described (Hoffman and Winston, 1987). Biotinylated peptides present in protein extracts prepared as described above but without gel filtration were analyzed on Western blots using $^{35}$S-Streptavidin as described (Gornicki and Haselkorn 1993).

5.11.2 Results

5.11.2.1 Complementation of a Yeast ACC1 Null Mutation with Wheat Cytosolic ACCase The inventors assembled a chimeric gene consisting of the yeast GAL10 promoter, yeast ACC1 leader, wheat cytosolic ACCase cDNA and yeast ACC1 3'-tail in high copy number yeast expression vectors of the pRS series (Christianson el al., 1992). The coding sequence was assembled from fragments of different cDNA clones described earlier, all encoding the cytosolic isozyme but representing transcripts of different genes (Gornicki et al., 1994). Some fragments were generated by PCR™ to introduce new restriction sites to simplify the cloning process and to enable future manipulations. The GAL10 promoter was selected for its strength and tight regulation. Leader and tail sequences from the ACC1 gene were fused to the wheat cytosolic ACCase coding sequence to provide proper yeast transcription and translation signals as well as mRNA processing and stability elements. This design, in addition to high copy number of the vectors, was selected in an attempt to ensure a high steady state level of the transcript that would overcome potential problems with efficient translation of the foreign coding sequences, protein degradation and inefficient modification (biotinylation) of a foreign protein of the ACCase size (250 kDa). In addition, down-regulation of the expression of the chimeric gene was desired for in vivo inhibition studies described below. The overall structure of the plasmids containing the chimeric gene as well as the control plasmid containing the yeast ACC1 gene are shown in FIG. 1A.

The chimeric gene was introduced into heterozygous *S. cerevisiae* strain W303D-ACC1$^{\Delta LEU2}$ (Table 3) in which one allele of the ACC1 gene was replaced with a LEU2 cassette. Sporulation was induced and 14, 39 and 16 asci were dissected in a standard tetrad analysis for strains complemented with gyccwy-pRS423, gyccwy-pRS424 and ACC1-pRS426, respectively. About 45% of the resulting spores were viable. However 8 sets of 3 or 4 viable spores derived from a single tetrad were obtained for strains containing the chimeric wheat gene. This result indicates that the gene can complement the ACC1 mutation as haploid ACC1 disruptants do not grow beyond a few cell divisions (Haslacher et al., 1993). Marker analysis of a set of 28 haploid strains derived from 10 tetrads followed by Southern analysis of 16 of them confirmed this conclusion. Low spore viability has other causes than lack of complementation. Complementation was the expected outcome for the ACC1-containing plasmid as the same SacI fragment of yeast genomic DNA was shown to be sufficient for complementation (Haslacher et al., 1993).

A collection of 10 haploid strains was subjected to marker and mating type analysis (Table 3). The DNA content of these strains was verified by Southern analysis using yeast and wheat ACCase-specific DNA probes. Finally, Western analysis with $^{35}$S-streptavidin (FIG. 2), and with antibodies specific for wheat ACCase confirmed expression of full-size wheat cytosolic ACCase in the gene-replacement strains. The amount of biotinylated peptides does not vary greatly between the strains (FIG. 2) except for strain MJ 9.12 (lane 6) that produces a significantly higher amount of ACCase. The reason for this "over-production" is not known. Wheat cytosolic ACCase migrates in an SDS-gel significantly faster than the yeast protein (FIG. 2). This is true for the native wheat cytosolic ACCase in wheat germ extract as well, but wheat cytosolic ACCase is 2 kDa larger than yeast ACCase (calculated from amino acid sequence). The slower migration of yeast ACCase may be due to protein modification.

TABLE 3

YEAST STRAINS

| No. | Strain | Construct/gene | Parent vector | MAT | ACC1 | URA3 | LEU2 | HIS3 | TRP1 | Galactose dependence | ACCase content[5] |
|---|---|---|---|---|---|---|---|---|---|---|---|
| 1 | MJ 1.12 | gyccwy[1] | pRS424 | a | − | − | + | − | + | + | 0.80 |
| 2 | MJ 1.13 | gyccwy[1] | pRS424 | α | − | − | + | − | + | + | 0.88 |
| 3 | MJ 6.8 | gyccwy[1] | pRS423 | a | − | − | + | + | − | + | 0.69 |
| 4 | MJ 6.9 | gyccwy[1] | pRS423 | α | − | − | + | + | − | + | 0.78 |
| 5 | MJ 9.11 | yeast ACC1[2] | pRS426 | a | + | + | + | − | − | − | 1.12 |
| 6 | MJ 9.12 | yeast ACC1[3] | none | α | + | − | (+)[4] | − | − | − | 3.76 |
| 7 | MJ 9.13 | yeast ACC[3] | none | α | + | − | − | − | − | − | 1.27 |
| 8 | MJ 9.14 | yeast ACC1[2] | pRS426 | a | + | + | + | − | − | − | 1.23 |
| 9 | W303D | yeast ACC1[3] | none | a/α | + | − | + | − | − | − | 1.00 |
| 10 | W303D-ACC1$^{\Delta Leu2}$ | yeast ACC1[3] | none | a/α | + | − | + | − | − | − | 0.59 |

All strains were obtained by sporulation of W303D-ACC1$^{\Delta Leu2}$ transformed with an appropriate plasmid. The related haploid strains (1.12 and 1.13, 6.8 and 6.9, 9.11–9.14) described in this Table were obtained from single tetrads.
[1]GAL10 promoter/yeast ACC1 leader/cytosolic carboxylase wheat cDNA/yeast ACC1 3' tail, FIG. 1A;
[2]plasmid born;
[3]genomic;
[4]unexplained;
[5]Relative amount of the 250 kDa biotinylated peptide estimated from band intensities on Western blots probed with $^{35}$S-Streptavidin (e.g., FIG. 2) and normalized for pyruvate carboxylase (PCase) amount as an internal standard. Averages of three measurements are shown.
W303D relevant genotype (3): MATα/MATα, leu2-3,112/leu2-3,112 his3-11,15/his311,15 ade2-1/ade2-1 ura3-1/ura3-1 trp1-l/trp1-1 100/can1-tcan1-100 ACC1/ACC1;
W303D −ACC1$^{\Delta Leu2}$ relevant genotype (3): MATα/MATα, leu2-3,112/leu2-3,112 his3-11,15/his311,15 ade2-1/ade2-1 ura3-1/ura3-1 l/trp-1 can1-1 can1-100/can1-100 ACC1/acc1::LEU2

The level of ACCase activity in Seplhadex G50-purified protein is always 10–40 times higher for yeast strains expressing wheat cytosolic ACCase than in the control strain expressing yeast native ACCase from a multicopy plasmid. The wheat peptide is biotinylated efficiently, assessed by its functionality and by the ability to bind streptavidin on Western blots. Unexpectedly, however, the level of biotinylated 250-kDa wheat polypeptide expressed under full induction of the GAL10 promoter is comparable to that of the wild-type yeast. Comparison of relative signal intensities on Western blots probed with streptavidin and with antibodies against wheat cytosolic ACCase suggests that biotinylation is not complete. It is lower than biotinylation of ACCase in wheat germ extract used as a reference. Higher activity of the wheat cytosolic ACCase expressed in yeast may be explained by the lack of functional phosphorylation that inactivates yeast ACCase. Higher instability of the yeast protein, inhibition by other mechanisms or suboptimal conditions used to assay ACCase activity in crude protein extracts might produce the same result.

Since the deletion of the ACC1 gene in yeast is lethal, the complementation study clearly demonstrates that active wheat ACCase can be produced in yeast and that it can replace the yeast enzyme. Indeed, the gene-replacement strains grow in liquid medium almost as fast and to only ~20% lower density than the haploid strains containing a native yeast ACC1 gene either on the chromosome or on a plasmid (FIG. 3A). No differences in cell morphology were observed between the strains at the level of the light microscope.

The activity of the GAL10 promoter can easily be regulated in media containing no glucose by adjusting the galactose concentration. As expected, ACCase becomes limiting for growth in the gene-replacement strains grown at low concentrations of the inducer (FIG. 3B). In media containing glucose (liquid or plates) the activity of the chimeric gene is effectively repressed and the strains do not grow at all. Cells transferred from YPRG to YPR medium grow for several generations until internal galactose and ACCase and its products are exhausted and then growth ceases. Addition of galactose to a concentration of about 0.05% leads to full induction of the chimeric gene and normal growth (FIG. 3B).

5.11.2.2 In Vivo and In Vitro Analysis of Wheat ACCase Interaction with Inhibitors using the Yeast Expression System Two strains were selected for a detailed analysis. Haploid strain MJ 9.11 containing one copy of the yeast ACC1 gene (on the chromosome) and expressing ACCase under its own promoter was grown in YPDA medium. Haploid gene-replacement strain MJ 1.12 expressing wheat cytosolic ACCase from a multi-copy plasmid under the GAL10 promoter was grown in YPR medium supplemented with 0.01% galactose. Under these conditions, ACCase is limiting and the growth rate for MJ 1.12 is 10–20% of the rate observed under full galactose induction or the rate of growth of MJ 9.11 in YPDA. The growth of strain MJ 1.12 is strongly inhibited by cethoxydim (50% inhibition at ~20 $\mu$M). Sethoxydim and haloxyfop have no effect on MJ 1.12. MJ 9.11 is not affected by any of the three inhibitors at concentrations up to 800 $\mu$M (FIG. 4A). The drastically higher sensitivity of MJ 1.12 to cethoxydim is evident when growth curves are compared in an study that also reflects the different growth regimens described above (FIG. 4B). At 800 $\mu$M cethoxydim MJ 1.12 does not grow at all and MJ 9.11 is unaffected.

In vitro sensitivity of yeast ACCase and wheat cytosolic ACCase expressed in yeast to the three inhibitors was measured using yeast crude protein extracts purified by gel-filtration. Wheat germ extract was used in parallel to assess inhibition of the wheat plastid ACCase. It was shown previously that the ACCase activity in wheat germ extract is highly sensitive to haloxyfop, resembling the sensitivity of ACCase activity in purified chloroplasts (Gornicki and Haselkorn, 1993). The inventors conclude that the major component of the ACCase activity in wheat germ represents the plastid enzyme. Two peaks of ACCase activity were observed after ion-exchange chromatography of maize protein (Howard and Ridley, 1990). In that study, activity in the first minor peak was not inhibited by fiuazifop (50 $\mu$M) but activity in the major peak was. Two peaks of activity were also observed during purification of wheat germ ACCase by ion-exchange chromatography. An internal amino acid sequence of an ACCase peptide from the major peak, eluted at higher salt concentration (Gornicki and Haselkorn, 1993), matches the sequence of wheat plastid ACCase deduced from DNA sequence but differs from the cytosolic ACCase sequence (Gornicki et al., 1994). The two activities most likely represent cytosolic and plastid isozymnes, respectively.

In the inventors' in vitro studies, the yeast ACCase is the least sensitive, wheat cytosolic enzyme expressed in yeast is significantly more sensitive and the plastid enzyme in wheat germ extract is very sensitive (FIG. 5). Sethoxydim does not inhibit the yeast or wheat cytosolic enzymes and is the weakest inhibitor of the wheat plastid enzyme (FIG. 5). These results show that the wheat cytosolic enzyme is indeed much less sensitive to aryloxyphenoxypropionate and cyclohexadione inhibitors than the wheat plastid enzyme.

The difference in in vitro sensitivity of yeast and wheat cytosolic ACCase to cethoxydim translates to a dramatic difference in the in vivo sensitivity (FIG. 4A and FIG. 4B). This phenomenon can be best explained by the limiting amount of ACCase in strain MJ 1.11 grown at low galactose concentration. This condition is expected to amplify the effect of the increased ACCase sensitivity to inhibitors introduced by the gene replacement. On the other hand, haloxyfop, which shows an almost identical inhibition pattern in vitro (FIG. 5) has no effect in vivo (FIG. 4A). That could result from poor uptake or inactivation of the inhibitor by yeast.

5.11.3 Utilities of the Yeast Expression System

The inventors have established an efficient and flexible yeast expression system to produce plant ACCase polypeptides in their active conformation. The inventors can answer the first important questions: the inventors' cDNA can produce full length and active enzyme in yeast and the "wheat gene" complements the deletion of the ACC1 gene in yeast. The high level of ACCase activity in transgenic yeast strains also reflects efficient modification of the wheat apoprotein by yeast holocarboxylase synthase. This is despite the fact that amino acid sequences of the two carboxylases, yeast and wheat cytosolic, are only about 40% identical (Gornicki et al., 1994). The yeast expression system was selected over E. coli to avoid potential problems such as protein solubility, folding or efficient modification (biotinylation). Any ACCase isozyme or variant can be analyzed in vivo (in an appropriate yeast strain) and in vitro (yeast extracts), and purified for biochemical and structural studies. Expression of ACCase fragments, e.g,. the two-domain BC plus BCCP sub-fragmenit with biotin carboxylation activity or inhibitor-binding domain also is possible. The strong GAL10 promoter and high copy-number plasmids are chosen to ensure high level and regulated expression. At low concentrations of the inducer, ACCase becomes limiting for growth, which enhances transgenic yeast sensitivity to ACCase specific inhibitors. Under full induction, enough active ACCase can be obtained for biochemical and structural studies.

Plasmids that can drive the expression of active wheat ACCase in yeast serve as a source of DNA for further manipulations. Because the size of the wheat ACCase cDNA (~8 kb) makes such manipulations difficult, the inventors introduced new restriction sites that allow the inventors to move almost the entire open reading frame as one SalI fragment. A short linker encoding the AUG start codon (with engineered NcoI site) was then added to fuse the open reading frame to a proper yeast leader and promoter (GAL10). This two-step construction scheme is compatible with the pRS series of yeast shuttle vectors, so in addition the inventors can use different selectable markers present in these vectors (Christianson et al., 1992). This modular design makes many modifications possible, e g., adding a chloroplast transit peptide for later use in a plant system, or a tag to aid peptide purification.

Inhibitors are valuable tools for studies of enzyme mechanism. In addition, they find applications e.g., as herbicides in agriculture. Understanding the molecular basis of inhibitor action is an important goal. Two classes of potent inhibitors, aryloxyphenoxypropionates and cyclohexanediones, specifically taret plastid ACCase from Graminae (Golz et al., 1994; Holt et al., 1993; Konishi and Sasaki, 1994). Inhibitor-sensitive yeast gene-replacement strains, such as the strains described here, can be used to study these problems. Mutants that confer resistance can be selected and the mutation site(s) identified. These point mutations will define inhibitor binding sites that can be further studied by other methods to reveal structural details of the inhibitor-enzyme interaction as well as the enzyme mechanism.

Plant-specific inhibitors have no effect on the growth of the wild-type yeast. On the other hand, the inventors have identified one compound, cethoxydim, that completely inhibits growth of the inventors' gene-replacement yeast strains in liquid cultures at reasonable concentration. It is also an effective inhibitor under conditions used to select for resistant survivors on solid media. This is despite the fact that the wheat cytosolic ACCase expressed in the inventors' gene-replacement strain is less sensitive than the plastid enzyme. Indeed, in an in vitro assay this compound moderately inhibits yeast-expressed wheat cytosolic ACCase. Yeast ACCase, although not completely resistant, is less sensitive. Cethoxydim, as other aryloxyphenoxypropionates and cyclohexanediones, is a much stronger inhibitor of the wheat plastid ACCase as reflected by the in vitro assay of wheat germ extracts. Chimeric proteins composed of cytosolic (herbicide resistant or tolerant) or plastid resistant mutant (isolated as described above) and plastid (herbicide sensitive) sequences can be analyzed for activity and inhibitor sensitivity/resistance using the yeast gene-replacement strains.

5.12 Example 12
Genes Encoding ACCase of Hexaploid Wheat

In this example the inventors describe full length cDNA and parts of the corresponding genes encoding wheat plastid ACCase. The inventors then report the results of chromosome mapping of both plastid and cytosolic ACCase genes in wheat.

5.12.1 Materials and Methods
5.12.1.1 Isolation and Analysis of ACCase Genomic Clones A λ EMBL3 wheat genomic library (*Triticum aestivum*, var. Hard Red Winter Tam 107, 13-day light grown seedlings, Clontech, Palo Alto, Calif.) was screened as described before (Podkowinski et al., 1996) with a 420-bp cDNA probe AK6. 39 positives were found among ~5×10⁶ plaques tested. Probe AK6 was PCR™-cloned using primers based on the cDNA sequence available from GenBank (Z23038). Single-stranded cDNA was prepared as described before (Gornicki et al., 1994) using gene-specific primer 5'-CCTCCGAGTTTCGCTCTG-3' (SEQ ID NO:18)
and was followed by PCR™ amplification with gene-specific primers 5'-TTTCCCTTGGCTATCATCA-3' (SEQ ID NO:19) and
5'-TATTCTAGGGCCTATGAG-3' (SEQ ID NO:20), cloning into the Invitrogen vector PCR™II and sequencing. DNA from the partially purified 1 pools was prepared by the DEAE-cellulose method (Mundy et al., 1995) and analyzed by PCR™ with a gene-specific downstream primer

5'-AGCATTGCTTGAGCTGTCTTAGTA-3' (SEQ ID NO:21)

and λ EMBL3 specific primers flanking the BamHI cloning site (right arm primer,

5'-CAGCGCACATGGTACAGCAAG-3' (SEQ ID NO:22)

or left arm primer,

5'-CATGGTGTCCGACTTATGCCC-3' (SEQ ID NO:23).

Expand Long Template PCR™ System (Boehringer Mannheim, Indianapolis, Ind.) was used according to the manufacturer's protocol . The PCR™ products were analyzed on Southern blots with probe AK6. 5 large hybridizing fragments corresponding to the genomic clones extending the furthest upstream of the target site for probe AK6 were identified. A ~6-kb fragment from one of these clones was PCR™-cloned into PCR™II vector using the left arm primer and the gene-specific primer, and sequenced to verify its identity. A ~1.3 kb SalI-XbaI 5'-end (with respect to the gene orientation) fragment of this clone was then used as a probe to rescreen the library. Two different clones, 274 and 325, containing ACCase-specific sequences hybridizing with this probe but not with AK6 were found, purified and mapped. SalI restriction fragments of these genomic clones were subcloned into pGEM and sequenced. Sequenced parts of the two clones are shown in FIG. 6.

5.12.1.2 Analysis of mRNA by Rapid Amplification of cDNA Ends (RACE)

A set of 9 cDNA fragments corresponding to mRNA 5'-ends were prepared by T/A cloning of 5'-RACE products into the vector pC2.1 (Invitrogen, San Diego, Calif.) and sequenced. Total RNA from 15-day old wheat (*Triticum aestivum* var. Tam 107, Hard Red Winter) plants was prepared as described in (Chirgwin et al., 1979). A Gibco BRL 5'-RACE kit was used according to the manufacturer's protocol. The first strand of cDNA was prepared using the gene-specific primer:

5'-GGCGAATAGACTGGTTAGGGTCTG-3' (SEQ ID NO:24)

followed by the addition of a homopolymeric dC- or dA-tail. dT-anchor primer

5'-GCGGACTCGAGCGACAAGCTTTTTTTTTTTT-TTTT-3' (SEQ ID NO:25)

was used for the second strand synthesis of the dA tailed cDNA. Universal primers

5'-GCGGACTCGAGTCGACAAGC-3' (SEQ ID NO:26), for the dA tailed cDNA and a gene-specific primer

5'-GAACACGACGACTTTTCTTCTTGG-3' (SEQ ID NO:27)

were used in the first round of PCR™. The universal primers and another gene-specific primer

5'-GGGCAGATGGTTGGAATGCAGCAC-3' (SEQ ID NO:28)

were used for reamplification. The gene-specific primers were targeted to a stretch of 5'-end coding sequence identical in clones 274 and 325.

5.12.1.3 Cloning of Four Overlapping cDNA Fragments Containing the Entire Plastid ACCase Coding Sequence Single stranded cDNA prepared as described (Gornicki et al., 1994) was used as a template for PCR™. The following primers were used for cDNA synthesis and PCR™, respectively:

fragment 1,
- 5'-GACTGTGAAGCGCAGCTACATTGC-3' (SEQ ID NO:29),
- 5'-GAACACTGCATCTGCGCTGTTTG-3' (SEQ ID NO:30) and
- 5'-GCAACTGAACTTCAAGATGTCGAC-3' (SEQ ID NO:31);

fragment 2,
- 5'-GCGCAAGAGACATGTTGGTGAGTGC-3' (SEQ ID NO:32) and
- 5'-GCTGCTCTAGACACTCCATATGC-3' (SEQ ID NO:33),
- 5'-TCAAGCAGCAGGGGTTCCGACTCTT-3' (SEQ ID NO:34) and
- 5'-GCTCATGACACTCCATATGCAAAAACATG-3' (SEQ ID NO:35):

fragment 3,
- 5'-TATATGCAACGGGTCTGTCAGGTG-3' (SEQ ID NO:36),
- 5'-AGGATCCAGATGACGGATTCAAGCC-3' (SEQ ID NO:37) and
- 5'-ACTGCATGTGGGAGCTGTACACTT-3' (SEQ ID NO:38);

fragment 4,
- 5'-GGATGCGTTGGTATCATCTGATC-3' (SEQ ID NO:39) and
- 5'-GGTCGGTTACAGCCGAATAGTATCC-3' (SEQ ID NO:40),
- 5'-ACTTGGCATACGGTGCATACAGCGTA-3' (SEQ ID NO:41) and
- 5'-CGTCGACGGTATCATCTGATCATTAAGGAC-3' (SEQ ID NO:42).

The four sets of primers were designed based on the available genomic (clones 274 and 325 described above) and cDNA sequences (GenBank Z23038), and used to amplify four overlapping cDNA fragments such that the 5'-end of fragment 1 included the ACCase translation start codon and the 3'-end of fragment 4 included the stop codon. The resulting products were cloned into PCR™ 2.1 and sequenced. A single product was obtained for fragment 1 and 4, and three different clones were obtained for fragments 2 and 3. Sequences of the three clones of fragment 3, which is about 4 kb in size, differ by 2 nucleotides when compared in pairs. Because of this rather low variation, the inventors assumed that the differences are due to PCR™ errors and that the three clones originated from the same transcript.

5.12.1.4 Chromosome Localization

Nullisomic-tetrasomic (NT) lines of Chinese Spring wheat (Sears, 1996), where nullisomy for a specific chromosome is compensated by four copies of a homoeologue. were used to assign ACCase gene fragments to individual chromosomes. NT 2A and NT 4B plants were identified cytologically, as these stocks are maintained as monosomic-tetrasomic lines. Ditelosomics (Dt) of Chinese Spring (Sears and Sears, 1978) were used for arm location of ACCase gene fragments. Dt lines 2AL, 4AS, 5AS, 2BS, 4BL, 5BS, and 5DS were cytologically identified in the progeny of ditelo-monotelo lines. ACCase gene fragments were placed on genetic linkage maps of an *Aegilops tauschii* F2 mapping population that consisted of 60 F2 progeny derived from the cross of *Ae. tauschii* accessions TA1691, var. meyeri and TA 1 704, var. typical (Kam-Morgan et al., 1989; Gill et al., 1991). *Ae. tauschii* Coss. (syn. *Aegilops squarrosa* L., syn. *Triticum tauschii* (Coss.) Schmal. 2n=14, DD) is the D genome progenitor of common bread wheat (*T. aestivum* L. em. Thell., 2n=6x=42, AABBDD) and is synthenic with the D genome of bread wheat. Isolation of DNA and Southern analysis were done as described (Riede and Anderson, 1996; Gill et al., 1993. Probes were hybridized to DNA from NT and DT stocks and resulting autoradiographs were scored visually to identify fragments absent in any of the stocks. If a fragment was absent in a particular NT stock, the inventors inferred its location on the chromosome in the nullisomic condition. Concomitant presence of a double-dose fragment in the stocks tetrasomic for a particular chromosome was used as additional evidence for the proper localization of fragments. In the analysis of DTs, a fragment absent in a stock indicated its presence on the opposing arm of that chromosome. Linkage analysis was done using MAP-MAKER V2.0 (Lander et al., 1987)with a LOD of 2.0 and the Kosambi mapping function (Kosambi, 1994).

5.12.1.5 Probes

B1, 3.4 kb BamHI fragment of the full length cDNA assembled from overlapping cDNA clones encoding wheat cytosolic ACCase. 5'F12, is a 0.53 kb SalI-SacII fragment of ACCase C2. Product size and sequences of primers used to prepare probes by PCR™ were as follows: 5'Fl1, 0.75 kb,
- 5'-CCAGCGGGCCATGTCACTACC-3' (SEQ ID NO:43) and
- 5'-AACAGCTATGACCATG-3' (SEQ ID NO:44) (vector primer);

Int11, 0.36 kb,
- 5'-TGGCGGCGCGCCTCCGGACGGACC-3' (SEQ ID NO:45) and
- 5'-CAGACGGGGCGAACCCGGCAATCC-3' (SEQ ID NO:46);

Int12, 0.44 kb,
- 5'-TCCGGCCGAACCGACGGTACGCGC-3' (SEQ ID NO:47) and
- 5'-CAGACGGCACGAAGAAGCCGCCCG-3' (SEQ ID NO:48), Pro1, 0.30 kb,
- 5'-GATTAAATCATTCGCTCCAGAACT-3' (SEQ ID NO:49) and
- 5'-CATCTTAGTCCAACATTCATGGAG-3' (SEQ ID NO:50);

Pro2, 0.36 kb,
- 5'-CAAGGGGAAATGGAATCGACTCCG-3' (St-.Q ID NO:51) and
- 5'-TCAAGTGTATGGACATACACGCGC-3' (SEQ ID NO:52);

Pro21, 0.40,
- 5'-TTCTTATTTGATTGTTTAATAGTA-3' (SEQ ID NO:53) and
- 5'-TTTTTGAGGATGCAATGGTGCAC-3' (SEQ ID NO:54);

Pro4, 0.29 kb,
- 5'-CCCTTGTGGCGCAACCAGTGACAC-3' (SEQ ID NO:55) and
- 5'-GTAGGTAGGGCCCCAACGCCTTGG-3' (SEQ ID NO:56).

An approximate position of the probes is shown in FIG. 6.

5.12.1.6 PCR™ Analysis of Genomic Clones

Identity of the 5'-ends of genomic clones 191 and 153 (Podkowinski et al., 1996) was verified by PCR™, and fragments of three new genes ACCase C3. ACCase C4 and ACCase C5 were cloned by PCR™ using the same downstream primer

5'-TGGTCAGATTCCACCATTATTGCC-3' (SEQ ID NO:57)

and the following upstream primers:

5'-TTCATCTCTCCCACACATAACACGAA-3' (SEQ ID NO:58),

5'-CAAAAGCATGATATGCCCTTGTGGC-3' (SEQ ID NO:59),

5'-TCCGGCCGAACCGACGGTACGCGC-3' (SEQ ID NO:60),

5'-CAAAAGCATGATATGCCCTTGTGGC-3' (SEQ ID NO:61) or

5'-TGGCGGCGCCGCCTCCGGACGGACC-3' (SEQ ID NO:62), respectively.

Identity of clones 191 and 153 was further verified by PCR™ using primers

5'-TTAGTCCAGGATGATAGGATTCTG-3' (SEQ ID NO:63) and

5'-CATTCTAGTCCAACATTCATGGAG-3' (SEQ ID NO:64),

5'-AGAGAAGATATGTTTTCAGCCGAG-3' (SEQ ID NO:65) and

5'-TTTTTGAGGATGCAATGGTGCAC-3' (SEQ ID NO:66), respectively. Identity of genomic clone 274 was verified by PCR™ using primers 5'-GCGGAGCGGACGAGGGGCTGGATC-3' (SEQ ID NO:67) and

5'-CGCCACAATCGCCAACCATGATCG-3' (SEQ ID NO:68).

Wheat (*Triticum aestivum* var. Tam 107, Hard Red Winter) genomic DNA was used as a template. PCR™V products were cloned into the vector pC2.1 (Invitrogen, San Diego, Calif.) and sequenced.

All cloning, DNA manipulations and gel electrophoresis were as described (Sambrook el al., 1989). Expand High Fidelity PCR™ System, (Boehringer Mannheim, Indianapolis, Ind.) was used according to manufacturer's protocol. DNA sequencing was performed by Cancer Center Sequencing Facility, University of Chicago.

5.12.2 Results 5.12.2.1 Plastid ACCase Genes and cDNAs

A collection of clones containing fragments of genes encoding a putative plastid ACCase was obtained by screening a wheat genomic library with a cDNA probe, AK6, targeted to the 3'-end of the ACCase ORF. The probe was prepared by PCR™ with primers based on a cDNA sequence encoding a wheat cytosolic ACCase (Elborough et al., 1994). A 5'-end fragment of one of the genomic clones extending about 6 kb upstream from the target site of AK6 was then used to rescreen the library. Two genomic clones, 274 and 325, extending towards the 5'-end of the gene and long enough to include the beginning of the ACCase ORF as well as the promoter region were sequenced. The two λ clones represent two different but very closely related genes ACCase P1 (SEQ ID NO:7) and ACCase P2 (SEQ ID NO:8) (FIG. 6). The overall sequence identity of the 5-kb fragment of the two genes (FIG. 6) is 89% . Exon and coding sequences are 98 and 99.4% identical, respectively. The corresponding 619-amino acid sequence encoded by ACCase P1 and ACCase P2 differs by three amino acids (99.5% identity). Amino acid sequence of the biotin carboxylase domain deduced from the exon sequence was compared with sequences of some ACCases and other biotin-dependent carboxylases (Table 4). This comparison suggested that the two genomic clones encode wheat plastid ACCases whose sequence is 94% identical with the maize plastid ACCase but only 81–85% identical with cytosolic ACCases from other plants including wheat (Table 4). Amino acid sequence of the ACCase encoded by ACCase P1 and ACCase P2, when compared with the wheat cytosolic ACCase, revealed a 100-amino acid extension at the N-terminus which contains a putative plastid transit peptide. Comparison of the N-terminal amino acid sequence of the ACCase P1 and ACCase P2 gene products with the maize plastid ACCase strongly supports this conclusion (FIG. 7). Similarity with the transit peptide of the plastid *B. napus* ACCase is much less profound (FIG. 7). The chloroplast localization of the maize (Elgi et al., 1995b) and *B. napus* (Schulte et al., 1997) ACCase was confirmed by the proper transport studies.

TABLE 4

AMINO ACID SEQUENCE COMPARISON OF WHEAT ACCASES
WITH SOME OTHER BIOTIN-DEPENDENT CARBOXYLASES
(% IDENTITY)

| | | Full length | | Biotin carboxylase domain | | |
| --- | --- | --- | --- | --- | --- | --- |
| | | cytosolic (ccw) | plastid (pcw) | cytosolic ACCase C2 | plastic ACCase P1 | Accession number |
| Eukaryotic-type carboxylases | | | | | | |
| *Triticum aestivum* ACCase C1 | cytosolic | 99 | 63 | 99 | 82 | U39321 |
| *Triticum aestivum* ACCase P2 | plastid | — | — | 82 | 99.8 | N/A |
| *Arabodopsis thaliana* | cytosolic | 69 | 62 | 88 | 83 | L27074 |
| *Medicago sativa* | cytosolic | 70 | 65 | 87 | 85 | L25042 |
| *Brassica napus* | cytosolic | — | — | 87 | 83 | Y10301 |
| *Brassica napus* | plastid | 54 | 56 | 82 | 81 | X77576 |
| *Zea mays* | plastid | 65 | 81 | 82 | 94 | U19183 |
| *Homo sapiens* I | cytosolic | 36 | 34 | 59 | 58 | X68968 |
| *Homo sapiens* II | cytosolic | 36 | 33 | 58 | 58 | U19822 |
| *S. cerevisiae* | cytosolic | 31 | 31 | 56 | 57 | M92156 |

TABLE 4-continued

AMINO ACID SEQUENCE COMPARISON OF WHEAT ACCASES
WITH SOME OTHER BIOTIN-DEPENDENT CARBOXYLASES
(% IDENTITY)

| | | Full length | | Biotin carboxylase domain | | |
|---|---|---|---|---|---|---|
| | | cytosolic (ccw) | plastid (pcw) | cytosolic ACCase C2 | plastic ACCase P1 | Accession number |
| Prokaryotic-type carboxylases | | | | | | |
| Escherichia coli[1] | bacterial | — | — | 30 | 30 | M80458 |
| Anabaena 7120[1] | bacterial | — | — | 31 | 32 | L14862 |
| Nicotiana tabacum[1] | plastid | — | — | 30 | 30 | L38260 |
| Rattus rattus PCCase[2] | mitochondrial | — | — | 31 | 31 | M22631 |
| Saccharomyces cerevisiae PCase[3] | mitochondrial | — | — | 29 | 30 | J03889 |
| Arabidopsis thaliana MCCase[4] | mitochondrial | — | — | 30 | 29 | U12536 |

[1]Biotin carboxylase subunit of ACCase
[2]Biotin carboxylase-biotin carboxyl carrier subunit (a) of propionyl-CoA carboxylase;
[3]Pyruvate carboxylase;
[4]Biotin carboxylase-biotin carboxyl carrier subunit of methylcrotonyl-CoA carboxylase.
Accesion numbers for full length cDNAs: ccw, U10187; pcw N/A.

Identity of the genomie clone 274 was verified by PCR™ with the upstream primer located about 1.8 kb upstream of the translation start and wheat genomic DNA as template. Attempts to verify the continuity of the insert found in clone 325 by PCR™ on genomic DNA failed. Verification of the 5'-untranslated part of the gene is important as many clones isolated from the genomic library contain unrelated fragments of genomic DNA. λ clone 325 is such a ligation artifact in which an unrelated DNA is fused at a Sau 3a site to the 5' end of the fragment of gene ACCase P2 shown in FIG. 6. The 5'-end sequence of clone 274 resembles retrotransposon sequences (FIG. 6), an indication that this part of clone 274 contains intergenic DNA.

Four overlapping cDNA fragments covering the entire coding region of the wheat plastid ACCase were cloned by PCR™ and sequenced. Within the overlapping sequences (total length 600 nucleotides) these cDNAs are 99% identical. The corresponding amino acid sequences are 95.5% identical. The composite cDNA (pcw, SEQ ID NO:6, FIG. 6) is 6993 nucleotides long and encodes 2311 amino acid peptide (SEQ ID NO:9) with calculated molecular size of 255 kDa. This peptide includes the plastid transit peptide. The DNA and the corresponding amino acid sequence of pcw are more than 99% identical with the respective sequences deduced for genes ACCase P1 and ACCase P2. Results of amino acid sequence comparisons for the full length wheat plastid ACCase are summarized in Table 4.

Comparison of the genomic sequences with cDNA sequence pew revealed introns (FIG. 6) at conserved sites also found in the cytosolic ACCase genes of rape, Arabidopsis and soybean (Roesler et al., 1994; Anderson et al., 1995), including the two introns absent in the wheat cytosolic ACCase genes ACCase C1 and ACCase C2 (Podkowilski et al., 1996). An approximate localization of the transcription start site in wheat genes ACCase P1 and ACCase P2 was deduced from the longest cDNA clones obtained by 5'-RACE. Three different transcripts were identified, two of which correspond to genes ACCase P1 and ACCase P2, respectively. These cDNA sequences also revealed an additional intron present in both genes within the 5'-leader. The untranslated leader is at least 130–170 nucleotides long.

5.12.2.2 Cytosolic ACCase Genes

The inventors have previously cloned and partially sequenced several genomic clones encoding wheat cytosolic ACCase (Podkowinski et al., 1996). (Genomic clones 31, 191 and 233 represent gene ACCase C1 and clone 153 represents gene ACCase C2 (FIG. 6). The identity of λ clones 191 and 153 was verified by PCR™, as explained above for the plastid ACCase genes, with the upstream primers located 2.2 and 2.8 kb upstream of the translation start, respectively. The 5'-ends of clones 191 and 153 have been sequenced (SEQ ID NO:1 and SEQ ID NO:2, respectively). Fragments of three additional genes, ACCase C3, ACCase C4 and ACCase C5 (FIG. 6, SEQ ID NO:3, SEQ ID NO:4. and SEQ ID NO:5, respectively) were cloned by PCR™. The sequence of the first intron of the five genes differs significantly, with ACCase C1 and ACCase C5 being the closest relatives (~96% sequence identity). Gene ACCase C4 corresponds to the previously identified transcript represented by cDNA clone 39 (Gornicki et al., 1994). The presence of a putative intronless pseudogene related to the cytosolic ACCase genes (94% sequence identity) (Podkowinski el al., 1996) was also verified by PCR™ amplification using genomic DNA as template, cloning and sequencing.

5.12.2.3 Chromosome Localization of ACCase Genes cDNA probe AK6 specific for plastid ACCase genes hybridized to the short arms of group 2 chromosomes in the Chinese Spring aneuploid stocks. Genetic linkage analysis indicated that this probe hybridized to a single restriction fragment in A. tauschii and mapped to the distal tip of chromosome 2DS (FIG. 8A, FIG. 8B, and FIG. 8C). If multiple genes are present in each chromosome set they must be arranged in tandem in the same locus. However, the cloning and sequencing studies revealed, so far, only three different genes for the plastid ACCase.

cDNA probe B1 encoding cytosolic ACCase hybridized to the long arms of group 3 chromosomes. as well as the long arm of chromosome 5D. Probe B1 is expected to reveal the location of all cytosolic ACCase genes whose coding sequence is ~98% identical (Podkowinski et al., 1996; (Gornicki and Haselkom, 1993) as well as the location of the putative pseudogene whose sequence is 94% identical. Genetic linkage analysis of this probe in the F2 population revealed that it mapped distally on 3DL as well as 5DL of Ae. tauschii (FIG. 8A., FIG. 8B, and FIG. 8C). Gene specific probes for ACCase C1 (Pro1 and Int 11) detected restriction fiagments on the long arms of group 3 chromosomes. Gene specific probes for ACCase C2 (Pro 21) and ACCase C4 (Pro 4) detected restriction fragments on the long arms of chromosome 3B and 3D. Furthermore, these four probes all mapped distally on chromosome 3DL of *Ae. Tauschii* (FIG. 8A, FIG. 8B, and FIG. 8C). No gene specific probes for ACCase C3 and ACCase C5 were used in this study. If multiple copies of the cytosolic ACCase gene are present in each chromosome set, as suggested by the number of different genes detected by sequencing, they lie in tandem on the long arms of group 3 chromosomes. The gene-specific probes were targeted to the least conserved sites in the gene to eliminate cross-hybridization. Sequence comparison of probe Pro 1 and the available sequence of gene ACCase C2, and probe Pro 21 with the available sequence of gene ACCase C1 reveals no sequence similarity significant for hybridization. A weak cross-hybridization between Pro21 and Pro4, and ACCase C4 and ACC2 respectively, is possible.

None of the gene-specific probes hybridized to the locus on chromosome 5D identified with probe B1. This result suggests that the putative pseudogene is located on chromosome 5D. The existence of a different functional cytosolic ACCase gene located on chromosome 5D with significantly different sequence of the untranslated regions and not detected by the gene-specific probes used in this study can not be ruled out. All gene-specific probes, except for F15'1 and F15'2 (FIG. 6), lie within ACCase genes as verified by PCR™ studies described above. Probes F15'1, F15'2 and Int12 hybridized with multiple sites, suggesting that they contain a repetitive sequence element. The 5'-end of clone 191 shows significant similarity to such a sequence (FIG. 6).

5.13 Example 13

Nucleic Acid Sequences of Wheat Cytosolic and Plastid ACCases 5.13.1 Nucleic Acid Sequence of the 5'-End of Wheat Cytosolic ACCase C1(SEQ ID NO:1)

```
TTCATCTCCCACACATAACACGAAAACCAGAACAAAACACCCCGCGACTACGATTGGAGA
TGTAGGCATCAAAGGCGTCGAGACCTATGCCAAGCACACCATCCATCTGTGACCATGAAG
CACAACTATTCATCTTCCACCAGCCCCGCCTCCATGAATGCTGGACTAGAATGTGAATGT
GTACTGCCGCGTGCGCGTGTGTCCGTTTGCCTCGGCGGAACACCACCAGCCCGGTACAGC
AAGCGATTTGTGACCGTCAACTAAATTTGGAATCGTTGGCGCATAATCATTGGAATATGC
ATGTCTCCGTTACAAGGCACGGACAATTAGCTAGACAACACACCCATGATGCAATTAGCT
AGACAATTAGCTAGACAACACACCCACGGACAATTAGCACCGACGACTACGGGACGGCCG
GACGGTGACGGGACGTGGACGAAGCCGAGCGGAGCACGCCACCGGAGCGGAGGGAGCGA
GCTGAGCACATCGAGTCCAGGGCAGACACGCCGGAGAGACAGGTGCAACGACGCACCCAT
CCGTCCATCCGCCCGCCCAACCAGGGCCATGCGGCCCAACTACCCGTCGTCCCCGTCTAG
ACCACGCCCCCACCTGCCCCGCCCCACCCCACCCCCAACTCCTCCATGAATGCACGCAT
TTCATCGCTCCAACCACAACGCAGCAGCCCCAGCACCAGCGGCCTCGGCGACGCGGCGCG
CATTTATACCACGCAATTCCATCTGGATCTCCACCTGGCCGCAGCACGGGTTTCCTCCTC
CCTCCCCGCGCGGCATTCCGTCGAACGGCTTGGCGGCGCGCCTCCGGACGGACCCACGGT
AAGCTCCCCCTGCCCTTGCTATGCCCCTGCTTCTGCACGCATCTTCCGATTTTCGCTGGA
GCGCTCCGCCTCCGCCTATGCGTGCGGGCGATTGACTGGGCCGGACTTGCCATGGACTCG
TACTGACCAGTGATGTACTCGCTCGCTAGCCTCTCCGCCCACGCCGGCCTCAAATCGAGC
GCGCGTAGGCTGCCTCCAGGCCCCAATCCAAGCAGCGCAGCGCAGGGCCTTCCTGCTGAT
TCTCTCTCAGCGCCAGGAGATCACGGGACCAGATACCACTGCTAGCAGTCGACCCGTGCC
GTCGCCGGATTGCCGGGTTCGCCCCGTCTGGCATTACGTCGAGCGGGTGGTGGGCGCGCG
CGACTGGCCGGGTTTTGGGCACACTTGTTGCTTACTTCCTTCTGCTGAATGCCGGAATTC
AAGTCCATTTCCCTCTTTGCTCCTGCTTGGACTAACCAGTCCCCTAGTGTGGACTACAGC
ATTTTTTTCGCGTATTTTTAATGTGATCTCTGGTCTTGCTCTTCTGGTTCTGCTGGTTGT
TGACTAGAATTCTGCACTCTCCCATGGCACTCTTGCCGGAGGAATTTCCCGATTTAGCTA
GCCGTTAATTAGTGCCACCATGTTGTTGTTTTCTGTAGTACCATTTTAGCATCTGGTACA
GAAAAAGGGCACACACATGCCAAACCGAAAAGAAATATCCCAGTGCTGCAATTCTACGCT
AATCGGACATAAATGATTGATGCGCTAACGGACGGACTTGTTCTTTTGCTTTTCCCAGCG
CTGAAGGTTGGAGGGGGCAATAATG
```

5.13.2 Nucleic Acid Sequence of the 5'-End of Wheat Cytosolic ACCase C2 (SEQ ID NO:2)

```
CAAAAGCATGATATGCCCTTGTGGCAAAACCGGTGACACGGGAGTACAACATGTTTCACC

ACCAACACGTCACCCGAGAAACGGAATAAACACCCCGCAGTATGTTTGAGGCGTTGGCAT

CAAAAGCGTTGGGACCTATGCTAGGCACAACATCCATCCGTGACGGCGAAGCGCAACTAT

TGTCTTCAAGGGGAAATGGAATCGACTCCGCACCAACGGGAGCGGAGGGAGTCTACATCA

CACCCGTCACGTGTCCCCGCCCCGTAAATGCACGACTAGAAGGTGCACCATTGCATCCTC

AAAAAAGAAAAAAAAAAGCGAATCAACCTGTGGTTGGTTGGTTAGAGGGACTGTGGTATC

CCCAGCCCACCATGGTTCAAATCCTGGTGCTCGCATTTATTTCTGGATTTATTTTAGGAT

TTCCGGCGATGCGCATTCAGTGGGAGGTTCATAGGGATGAGTGTATACGCGTGTATATGA

GCGCTTGCGTCTGTACTGTGTTAAAAAAAAAGAAAAAAAAAGATTATGTACCATTGCGCG

TGTATGTCCATACACTTGAGCCGATTAGCTAGAGAACAGGGTCATGATGCAGTCCGAGTT

ACGGTAACGAACAAACGGGAGTCAACAAGGCGGCACAAGACGCCGTGGTGGCTTGGCCGA

CGACTACGGGACGGCCGGACGGGTCGGGGACGTGAGCGAAGCCGAAGGGAGCACGCCACC

GGAGCGGAAGGAGCGAGCACATCGAAGGCGTTGGGGCCCTACCTACACACGCCGGAGA

GACAGGTGCAACGACACACCAATCCGTCCAACCAGGGCGATGAGGCCCAACAACCTGTCG

TCGACTCCTCCCCGTCTCCACCTCCACCACACCCCCCACCTGCCCCGCCCCACCCCACCC

CACCCCCAACTCCTCCATGAATGCACGCATTTCATCGCTCCTACCACAACGCAGCAGCAC

CAGCGGCCTCGGCGACGCGCCGCGCATTTATAGCAAGCAATTCCCCGTTGCCTCCGCCTC

CGCCGCCGCTGCCTCTCCTGGATCTCCATCTGGCCGCAGCACGGCCTTCTTCCTCCTTCC

TCCCTCCGCGGCATTCCGTCGAACGGCTTCGCGGCGCGGCTCCGGCCGAACCGACGGTAC

GCGCCCTGCCCGTCCCCCCTGCCCCGCCGTGCCCCTGCTTCTGCCCCCATCTTCCGGTT

TTCGCTGGAGCACCGCGTGCGTGTGTAGGTGATTGAGCGAGTCGGTCTCGCTACTGGC

TTCGGCCCGAGCTGCCGTGTCCCGGCGCGCGCGTAGGAGCAGTAGTACTACCACCAGC

TTCTCCGTCCCCGGGGCCTTCAAATCGAGCACGAGCCGGCTAGCTCCAGGCCCCCCAGTC

CCGCGCCGCGCAAGCGGCGCGGGGCCTTCCTGCTGGTTCTAGCGGCACGAGATCACGGAG

CGGGATACTGCTCTCGCGCGCGCGATTCGAGCTAGTTCGTGCGCGCGGAGTCCTGCTGAC

GCGGGATCCTGCCGACGATCGACCCGCGCCGTCGCCGAATTGGCGGGCGGCTTCTTCGTG

CCGTCTGGCATTACGTCGAACGGGTGGTGGGCGTGCGTGATTGGCCGGGTTTTGGGTGCT

TGCTGCTTCCGTCCTTGTGCTGAATGTCGGAATTCAAGTCCCTTTTCCCCTTCGCTCCTG

CTTGGAGTGGACTAACCTTAGTGTGGACTTCAACATTTTTTTCATGTGATCTAGGGTCTT

GCTGTTCTGTTTCTGCTGGCTGTTGACTATCAGCTTACTGTTGCGGATTGCGCACTTTCC

CCTGGCACTGTTTCCGGAGGAATTTCCTGATTTTTTTAGTTATTAGTGGTTAAATAGTAC

CATTATGTCTTTGTTTGCTTTGTGCCATTTTTAGCATCCAGTACAGAAAAAAAGGAATAA

ACGTGCAAAACTGAAAAATAATAACCCGGTGCTGTTTCGCTAACCAGACAGAATTGATTC

CACCATTTTCCTGATTTAGTTAGTAGTTAAATAGGACTACTATGTTTTTGTTCTGTTTGT

ACCATTTTAGCATCTAGTACAGAAAAAGCGCACACACATGCCAAACCGAAAAGAAATATC

CCAATGCTGCAATTCTACGCTAATCGGACATAAATGATTGATGCGCTAACAGACGGATTT

GTTCTTTTGCTTTTCCCAGTGCTGAAGGTTGGAGGGGGCAATAATGGTGGAATCTGACCA
```

5.13.3 Nucleic Acid Sequence of a Portion of Wheat Cytosolic ACCase C3 (SEQ ID NO:3)

```
TTCCGGCCGAACCGACGGTACGCGCTAGCCTCTCCGCCCACGCCGGCCTCAAATCGACCG
CGGTTCCGCTGCCCCCAGGCCCCAATCCGAGCAGCGCAGCGCAGGGCCTCCCTGCTGATT
CTAAGCGGCACGGAACCAGATACCACCGCTTTCCCGTGCGCGCGCGGCGTGAGATTCC
GAGTGCTCCAGCTAGTTCCTACACGCGGAGCGGACGCGAGGCGAGATCCTGCTAGCAGTC
GACCCGTGCCGTCGCCGGATTGGCGGGTTCGCGCCGTCTGGCATTACGTCGAGCGGGTGG
TGGGCGTGCGCGACTGGCCGGGTTTTGGGTATACTTGTTGCTTACTTCCTTGTGCTGAAT
GTCGGAATTCAAGTCCAGTTCCCTCTTTACTTCCTTGTGCTGGCCTGCTTCAACGTTTTT
TCACGTATTTTTAACGTGATCTGTTGTGTGGTCTTGCTGGCTGTTGACTATCAGCTCACT
GCTGCTAATTGTGCACTTTCCCGTGGCACTGTTGCTGGAGGAATTTCCCGATTTAGGTAG
TCGTTAATTAGTGCCACCATGTTGTTGTTTCTGTACCATTTTAGCATCTGGTACAGAAA
AAGGGCACACACATGCCAAACCGAAAAGAAACATCCCAGTGCTGCAATTCTACGCTAATC
GGGCATAAATGATTGATGCGCTAACAGACGGACTTGTTCTTTTGCTTTTCCCAGTGCTGC
AATTCTACGCTAATCGGACATAAATGATTGATGCGCTAACAGACAGACTTGTTCTTTTGC
TTTTCCCAGTGCTGAAGGTCGGAGGGGGCAATAATGGTGGAATCTGACCAGATAAACGGG
ACGCCCAACAGGATGTCCTCGGTCGAAGAGTTCTGTAAAGCGCTCGGGGGCGACTCGCCG
ATACACAGCGTGCTGGTTGCCAACAATGGGATGGCTGCGGTCAAGTTCATGCGCAGCATC
CGCACCTGGGCCTTGGAGACCTTTGGGAACGAGAAGGCCATTCTCTTGGTGGCTATGGCA
ACTCCA
```

5.13.4 Nucleic Acid Sequence of a Portion of Wheat Cytosolic ACCase C4 (SEQ ID NO:4)

```
CAAAAGCATGATATGCCCTTGTGGCGCAACCAGTGACACGAGAGCACACCACGTTTGATC
CCCAACACATCGCACGGAAATTTGGAAGAAAAAAGCCACCCCCGCAGCTACGATTCGAA
GATGTCGGCATCAAAGCCGTTTGGACCTGTGCGAGACAACAGCATCCATCCATGACGGCG
AAGCGCAACTATTTTCTTCAAGGGGAAATGGAATCGACTCCGCACGCCATCCGGGACGGG
AGCACGCCACCGGATGAGCGGAGCGAGCGAGCACATCCAAGGCGTTGGGGCCCTACCTAC
CCAAGGCAGACACGCCGGAGAGACAGGTGCAACGACACACCAATCCATCCGCCCAAGCAA
GCAAGCAGGGCCATGAGGACCAACTACCCGTCGTCCCCGTCTAGACCACACCCCCCACCT
GCCCCCACCCTCCCTCCCCCAACTCCTCCATGAATGCACGCATTTCATCATCGCCCCAAC
CACAACGCAGCAGCAGCGGCCTCGGCGACGCGCCGCGCATTTATAGCACGCAATTCCTCG
TTGCCTCCGCCGCCGCCGCCTGCCTGCCTCTCCTGGATCTCCATCTCTCCTTCGCGGCGC
GGCATTCCGTCGAACGCCTCCGCGGCGCGCCTCCGGGCGGACTCACGGTAAGCTCCCCCT
GCCCTTGCTGTGCCCCTGCTTCTGCTCGCATCTTCCGATTTTCGCCGGAGCGCTCCGCCT
CCGCCTATATGCGTGCGGGCGATTGACTGGGCCGGACCTGCCATGGACTCGTGCTTGACC
CGCCCGTGCCCCAGTGCGCGCGGGGAGGACCAGTGATGTACTCGCTCCCAGCCTCCCCGC
CCACGCCGGCCTCAAATCGAGCGCGCGTAGGCTGCCTCCAGGCCCCAATCCGAGTAGCGC
AGCGCGGGGCCTTCCTGCTGATTCTCTCTCAGCGCCAGGAGATCACGGCACCAGATACCA
CTGCTTCTGCGTGCGCGCGCGCGGCGTCAGATTCCGAGTGCTTCCACCTAGTCCGTACAC
```

```
GCGGAGCTGCCGCGGGATCCTGCTGACAGTCGACCCGTGCCGTCGCCGGATTGGCGGGTT

CGTGCCGTCTGGCATTACGTCGAGCGGGTTGTGGGCGCGCGCGACCGGCCGGGTTTTGGG

CACACTTGTTGCTTGCTTCCTTCTCCTGAATGCCGGAATTCAAGTCCATTTCCCTCTTTG

CTCCTGCTTGGAGTGGAGTAACCCCTAGTGTGGACTTCAACATTGTTTCACGTATTTTTA

ATGTCATCTGTGGTCTTGCTCTTCTGCTTCTGCTGGTTTGTCGACTATGAGCTTACTGTC

GTGAATTGTGCACTTTCCCGTGGCACTGCTGCCCTAGGAATTTCCGGATTTAGTTAGTCG

TTAATTAGTGCCACCATGCTGTTGTTTTGTCTGTACCATTTTAGCATCTGGTACAGAAAA

AGGGCACACACATGCCAAACCGAAAAGAAATATCCCAGTGCTGCAATTCTACGCTAATCA

CCCATAAATGATTGATGCGCTAACGGACGGACTTGTTCTTTTGCTTTTCCCAGTGCTGAA

GGTTGGAGGGGGCAATAATGGTGGAATCTGACCAGATAAACGGGAGGATGTCCTCGGTCG

ACGAGTTCTGTAAAGCGCTCGGGGCGACTCGCCGATACACAGCGTGCTGGTTGCCAACA

ATGGGATGGCTGCGGTCAAGTTCATGCGCAGCATCCGCACCTGGGCCTTGGAGACCTTTG

GGAACGAGAAGGCCATTCTCTTGGTGGCTATGGCAACT
```

5.13.5 Nucleic Acid Sequence of a Portion of Wheat Cytosolic ACCase C5 (SEQ ID NO:5)

```
TGGCGGCGCGCCTCCGGACGGACCCACGGTAAGCTCCCCCTGCCCTTGCTGTGCCCCTGC

TTCTGCTCGCATCTTCCGATTTTCGCCGGAGCGCTCCGCCTCCGCCTATATGCGTGCGGG

CGATTGACTGGGCCGGACCTGCCATGGACTCGTGCTTGACCCGCCCGTGCCCCAGTGCGC

GCGGGGAGGACCAGTGATGTACTCGCTCCCAGCCTCCCCGCCCACGCCGGCCTCAAATCG

AGCGCGCGTAGGCTGCCTCCAGGCCCCAATCCGAGTAGCGCAGCGCGGGGCCTTCCTGCT

GATTCTCTCAGCGCCAGGAGATCACGGCACCAGATACCACTGCTTCTGCGTGCGCGCG

CGCGGCGTCAGATTCCGAGTGCTTCCACCTAGTCCGTACACGCGGAGCTGCCGCGGGATC

CTGCTGACAGTCGACCCGTGCCGTCGCCGGATTGGCGGGTTCGTGCCGTCTGGCATTACG

TCGAGCGGGTTGTGGGCGCGCGCGACCGGCCGGGTTTTGGGCACACTTGTTGCTTACTTC

CTTCTGCTGAATGCCGGAATTCAAGTCCATTTCCCTCTTTGCTCCTGCTTGGACTAACCA

GTCCCCTAGTGTGGACTACAGCATTTTTTTCGCGTATTTTTAATGTGATCTCTGGTCTTG

CTCTTCTGGTTCTGCTGGTTGTTGACTAGAATTCTGCACTCTCCCATGGCACTCTTGCCG

GAGGAATTTCCCGATTTAGCTAGCCGTTAATTAGTGCCACCATGTTGTTGTTTTCTGTAG

TACCATTTTAGCATCTGGTACAGAAAAAGGGCACACACATGCCAAACCGAAAAGAAATAT

CCCAGTGCTGCAATTCTACGCTAATCGGACATAAATGATTGATGCGCTAACGGACGGACT

TGTTCTTTTGCTTTTCCCAGCGCTGAAGGTTGGAGGGGGCAATAATGGTGGAATCTGACC

AAATAAACGGGACGCCCAACAGGATGTCCTCGGTCGATGAATTCTGTAAAGCGCTCGGGG

GTGACTCGCCGATACACAGCGTGCTGGTTGCCAACAATGGGATGGCTGCGGTCAAATTCA

TGCGCAGCATCCGCACCTGGGCCTTGGAGACCTTTGGGAACGAGAAGGCCATTCTCTTGG

TGGCTATGGCAACTCCA
```

5.13.6 Nucleic Acid Sequence the Entire Wheat Plastid ACCase cDNA pcw (SEQ ID NO:6)

```
GAACACTGCATCTGCGCTGTTTGTCCAAAGGGAGGACGATGGGATCCACACATTTGCCCA
TTGTCGGCCTTAATGCCTCGACAACACCATCGCTATCCACTATTCGCCCGGTAAATTCAG
CCGGTGCTGCATTCCAACCATCTGCCCCTTCTAGAACCTCCAAGAAGAAAAGTCGTCGTG
TTCAGTCATTAAGGGATGGAGGCGATGGAGGCGTGTCAGACCCTAACCAGTCTATTCGCC
AAGGTCTTGCCGGCATCATTGACCTCCCAAAGGAGGGCACATCAGCTCCGGAAGTGGATA
TTTCACATGGGTCCGAAGAACCCAGGGGCTCCTACCAAATGAATGGGATACTGAATGAAG
CACATAATGGGAGGCATGCTTCGCTGTCTAAGGTTGTCGAATTTTGTATGGCATTGGGCG
GCAAAACACCAATTCACAGTGTATTAGTTGCGAACAATGGAATGGCAGCAGCTAAGTTCA
TGCGGAGTGTCCGAACATGGGCTAATGAAACATTTGGGTCAGAGAAGGCAATTCAGTTGA
TAGCTATGGCTACTCCAGAAGACATGAGGATAAATGCAGAGCACATTAGAATTGCTGATC
AATTTGTTGAAGTACCCGGTGGAACAAACAATAACAACTATGCAAATGTCCAACTCATAG
TGGAGATAGCAGTGAGAACCGGTGTTTCTGCTGTTTGGCCTGGTTGGGGCCATGCATCTG
AGAATCCTGAACTTCCAGATGCACTAAATGCAAACGGAATTGTTTTTCTTGGGCCACCAT
CATCATCAATGAACGCACTAGGTGACAAGGTTGGTTCAGCTCTCATTGCTCAAGCAGCAG
GGGTTCCGACTCTTCCTTGGAGTGGATCACAGGTGGAAATTCCATTAGAAGTTTGTTTGG
ACTCGATACCYGCGGAGATGTATAGGAAAGCTTGTGTTAGTACTACGGAGGAAGCACTTG
CGAGTTGTCAGATGATTGGGTATCCMGCCATGATTAAAGCATCATGGGGTGGTGGTGGTA
AAGGGATCCGAAAGGTTAATAAYGACGATGATGTCAGAGCACTGTTTAAGCAAGTGCAAG
GTGAAGTTCCTGGCTCCCCAATATTTATCATGAGACTTGCATCTCAGAGTCGACATCTTG
AAGTTCAGTTGCTTTGTGATCAATATGGCAATGTAGCTGCGCTTCACAGTCGTGACTGCA
GTGTGCAACGGCGACACCAAAAGATTATTGAGGAAGGACCAGTTACTGTTGCTCCTCGCG
AGACAGTGAAAGAGCTAGAGCAAGCAGCAAGGAGGCTTGCTAAGGCTGTGGGTTATGTTG
GTGCTGCTACTGTTGAATATCTCTACAGCATGGAGACTGGTGAATACTATTTTCTGGAAC
TTAATCCACGGTTGCAGGTTGAGCATCCAGTCACCGAGTGGATAGCTGAAGTAAACTTGC
CTGCAGCTCAAGTTGCAGTTGGAATGGGTATACCCCTTTGGCAGGTTCCAGAGATCAGAC
GTTTCTATGGAATGGACAATGGAGGAGGCTATGACATTTGGAGGAAAACAGCAGCTCTTG
CTACTCCATTTAACTTCGATGAAGTGGATTCTCAATGGCCAAAGGGTCATTGTGTAGCAG
TTAGGATAACCAGTGAGGATCCAGATGACGGATTCAAGCCTACCGGTGGAAAAGTAAAGG
AGATCAGTTTTAAAAGCAAGCCAAATGTTTGGGCCTATTTCTCTGTTAAGTCCGGTGGAG
GCATTCATGAATTTGCTGATTCTCAGTTTGGACATGTTTTTGCATATGGAGTGTCWWGAG
CAGCAGCAATAACCAACATGTCTCTTGCGCTAAAAGAGATTCAAATTCGTGGAGAAATTC
ATTCAAATGTTGATTACACAGTTGATCTCTTGAATGCCTCAGACTTCAAAGAAAACAGGA
TTCATACTGGCTGGCTGGATAACAGAATAGCAATGCGAGTCCAAGCTGAGAGACCTCCGT
GGTATATTTCAGTGGTTGGAGGAGCTCTATATAAAACAATAACGAGCAACACAGACACTG
TTTCTGAATATGTTAGCTATCTCGTCAAGGGTCAGATTCCACCGAAGCATATATCCCTTG
TCCATTCAACTGTTTCTTTGAATATAGAGGAAAGCAAATATACAATTGAAACTATAAGGA
GCGGACAGGGTAGCTACAGATTGCGAATGAATGGATCAGTTATTGAAGCAAATGTCCAAA
CATTATGTGATGGTGGACTTTTAATGCAGTTGGATGGAAACAGCCATGTAATTTATGCTG
```

-continued

```
AAGAAGAGGCCGGTGGTACACGGCTTCTAATTGATGGAAAGACATGCTTGTTACAGAATG
ATCACGATCCTTCAAGGTTATTAGCTGAGACACCCTGCAAACTTCTTCGTTTCTTGGTTG
CCGATGGTGCTCATGTTGAAGCTGATGTACCATATGCGGAAGTTGAGGTTATGAAGATGT
GCATGCCCTCTTGTCACCTGCTGCTGGTGTCATTAATGTTTTGTTGTCTGAGGGCCAGC
CTATGCAGGCTGGTGATCTTATAGCAAGACTTGATCTTGATGACCCTTCTGCTGTGAAGA
GAGCTGAGCCATTTAACGGATCTTTCCCAGAAATGAGCCTTCCTATTGCTGCTTCTGGCC
AAGTTCACAAAAGATGTGCCACAAGCTTGAATGCTGCTCGGATGGTCCTTGCAGGATATG
ATCACCCGATCAACAAAGTTGTACAAGATCTGGTATCCTGTCTAGATGCTCCTGAGCTTC
CTTTCCTACAATGGGAAGAGCTTATGTCTGTTTTAGCAACTAGACTTCCAAGGCTTCTTA
AGAGCGAGTTGGAGGGTAAATACAGTGAATATAAGTTAAATGTTGGCCATGGGAAGAGCA
AGGATTTCCCTTCCAAGATGCTAAGAGAGATAATCGAGGAAAATCTTGCACATGGTTCTG
AGAAGGAAATTGCTACAAATGAGAGGCTTGTTGAGCCTCTTATGAGCCTACTGAAGTCAT
ATGAGGGTGGCAGAGAAAGCCATGCACACTTTATTGTGAAGTCCCTTTTCGAGGACTATC
TCTCGGTTGAGGAACTATTCAGTGATGGCATTCAGTCTGATGTGATTGAACGCCTGCGCC
AACAACATAGTAAAGATCTCCAGAAGGTTGTAGACATTGTGTTGTCTCACCAGGGTGTGA
GAAACAAAACTAAGCTGATACTAACACTCATGGAGAAACTGGTCTATCCAAACCCTGCTG
TCTACAAGGATCAGTTGACTCGCTTTTCCTCCCTCAATCACAAAAGATATTATAAGTTGG
CCCTTAAAGCTAGCGAGCTTCTTGAACAAACCAAGCTTAGTGAGCTCCGCACAAGCATTG
CAAGGAGCCTTTCAGAACTTGAGATGTTTACTGAAGAAAGGACGGCCATTAGTGAGATCA
TGGGAGATTTAGTGACTGCCCCACTGCCAGTTGAAGATGCACTGGTTTCTTTGTTTGATT
GTAGTGATCAAACTCTTCAGCAGAGGGTGATCGAGACGTACATATCTCGATTATACCAGC
CTCATCTTGTCAAGGATAGTATCCAGCTGAAATATCAGGAATCTGGTGTTATTGCTTTAT
GGGAATTCGCTGAAGCGCATTCAGAGAAGAGATTGGGTGCTATGGTTATTGTGAAGTCGT
TAGAATCTGTATCAGCAGCAATTGGAGCTGCACTAAAGGGTACATCACGCTATGCAAGCT
CTGAGGGTAACATAATGCATATTGCTTTATTGGGTGCTGATAATCAAATGCATGGAACTG
AAGACAGTGGTGATAACGATCAAGCTCAAGTCAGGATAGACAAACTTICTGCGACACTGG
AACAAAATACTGTCACAGCTGATCTCCGTGCTGCTGGTGTGAAGGTTATTAGTTGCATTG
TTCAAAGGGATGGAGCACTCATGCCTATGCGCCATACCTTCCTCTTGTCGGATGAAAAGC
TTTGTTATGAGGAAGAGCCGGTTCTCCGGCATGTGGAGCCTCCTCTTTCTGCTCTTCTTG
AGTTGGGTAAGTTGAAAGTGAAAGGATACAATGAGGTGAAGTATACACCGTCACGTGATC
GTCAGTGGAACATATACACACTTAGAAATACAGAGAACCCCAAAATGTTGCACAGGGTGT
TTTTCCGAACTCTTGTCAGGCAACCCGGTGCTTCCAACAAATTCACATCAGGCAACATCA
GTGATGTTGAAGTGGGAGGAGCTGAGGAATCTCTTTCATTTACATCGAGCAGCATATTAA
GATCGCTGATGACTGCTATAGAAGAGTTGGAGCTTCACGCGATTAGGACAGGTCACTCTC
ATATGTTTTTGTGCATATTGAAAGAGCAAAAGCTTCTTGATCTTGTTCCCGTTTCAGGGA
ACAAAGTTGTGGATATTGGCCAAGATGAAGCTACTGCATGCTTGCTTCTGAAAGAAATGG
CTCTACAGATACATGAACTTGTGGGTGCAAGGATGCATCATCTTTCTGTATGCCAATGGG
AGGTGAAACTTAAGTTGGACAGCGATGGGCCTGCCAGTGGTACCTGGAGAGTTGTAACAA
CCAATGTTACTAGTCACACCTGCACTGTGGATATCTACCGTGAGGTCGAAGATACAGAAT
CACAGAAACTAGTGTACCACTCTGCTCCATCGTCATCTGGTCCTTTGCATGGCGTTGCAC
```

-continued

```
TGAATACTCCATATCAGCCTTTGAGTGTTATTGATCTGAAACGTTGCTCCGCTAGAAATA
ACAGAACTACATACTGCTATGATTTTCCGTTGGCATTTGAAACTGCAGTGCAGAAGTCAT
GGTCTAACATTTCTAGTGACACTAACCGATGTTATGTTAAAGCGACGGAGCTGGTGTTTG
CTCACAAGAACGGGTCATGGGGCACTCCTGTAATTCCTATGGAGCGTCCTGCTGGGCTCA
ATGACATTGGTATGGTAGCTTGGATCTTGGACATGTCCACTCCTGAATATCCCAATGGCA
GGCAGATTGTTGTCATCGCAAATGATATTACTTTTAGAGCTGGATCGTTTGGTCCAAGGG
AAGATGCATTTTTTGAAACTGTTACCAACCTAGCTTGTGAGAGGAAGCTTCCTCTCATCT
ACTTGGCAGCAAACTCTGGTGCTCGGATCGGCATAGCAGATGAAGTAAAATCTTGCTTCC
GTGTTGGATGGTCTGATGATGGCAGCCCTGAACGTGGGTTTCAATATATTTATCTGACTG
AAGAAGACCATGCTCGTATTAGCGCTTCTGTTATAGCGCACAAGATGCAGCTTGATAATG
GTGAAATTAGGTGGGTTATTGATTCTGTTGTAGGGAAGGAGGATGGGCTAGGTGTGGAGA
ACATACATGGAAGTGCTGCTATTGCCAGTGCCTATTCTAGGGCCTATGAGGAGACATTTA
CGCTTACATTTGTGACTGGAAGGACTGTTGGAATAGGAGCATATCTTGCTCGACTTGGCA
TACGGTGCATTCAGCGTACTGACCAGCCCATTATCCTAACTGGGTTTTCTGCCTTGAACA
AGCTTCTTGGCCGGGAAGTGTACAGCTCCCACATGCAGTTGGGTGGCCCCAAAATTATGG
CGACAAACGGTGTTGTCCATCTGACAGTTTCAGATGACCTTGAAGGTGTATCTAATATAT
TGAGGTGGCTCAGCTATGTTCCTGCCAACATTGGTGGACCTCTTCCTATTACAAAATCTT
TGGACCCACCTGACAGACCCGTTGCTTACATCCCTGAGAATACATGCGATCCTCGTGCTG
CCATCAGTGGCATTGATGATAGCCAAGGGAAATGGTTGGGGGCATGTTCGACAAAGACA
GTTTTGTGGAGACATTTGAAGGATGGGCGAAGTCAGTTGTTACTGGCAGAGCGAAACTCG
GAGGGATTCCGGTGGGTGTTATAGCTGTGGAGACACAGACTATGATGCAGCTCATCCCTG
CTGATCCAGGCCAGCTTGATTCCCATGAGCGATCTGTTCCTCGTGCTGGGCAAGTCTGGT
TTCCAGATTCAGCTACTAAGACAGCGCAGGCAATGCTGGACTTCAACCGTGAAGGATTAC
CTCTGTTCATCCTTGCTAACTGGAGAGGCTTCTCTGGTGGACAAAGAGATCTTTTTGAAG
GAATCCTTCAGGCTGGGTCAACAATTGTTGAGAACCTTAGGACATACAATCAGCCTGCCT
TTGTATATATCCCCAAGGCTGCAGAGCTACGTGGAGGGGCTTGGGTCGTGATTGATAGCA
AGATAAATCCAGATCGCATTGAGTTCTATGCTGAGAGGACTGCAAAGGGCAATGTTCTCG
AACCTCAAGGGTTGATCGAGATCAAGTTCAGGTCAGAGGAACTCCAAGAGTGCATGGGTA
GGCTTGATCCAGAATTGATAAATCTGAAGGCAAAGCTCCAGGGAGTAAAGCATGAAAATG
GAAGTCTACCTGAGTCAGAATCCCTTCAGAAGAGCATAGAAGCCCGGAAGAAACAGTTGT
TGCCTTTGTATACTCAAATTGCGGTACGGTTCGCTGAATTGCATGACACTTCCCTTAGAA
TGGCTGCTAAGGGTGTGATTAAGAAGGTTGTAGACTGGGAAGATTCTAGGTCGTTCTTCT
ACAAGAGATTACGGAGGAGGATATCCGAGGATGTTCTTGCGAAGGAAATTAGAGGTGTAA
GTGGCAAGCAGTTTTCTCACCAATCGGCAATCGAGCTGATCCAGAAATGGTACTTGGCCT
CTAAGGGAGCTGAAACAGGAAGCACTGAATGGGATGATGACGATGCTTTTGTTGCCTGGA
GGGAAAACCCTGAAAACTACCAGGAGTATATCAAAGAACTCAGGGCTCAAAGGGTATCTC
AGTTGCTCTCAGATGTTGCAGACTCCAGTCCAGATCTAGAAGCCTTGCCACAGGGTCTTT
CTATGCTATTAGAGAAGATGGATCCCTCAAGGAGAGCACAGTTTGTTGAGGAAGTCAAGA
AAGTCCTTAAATGATCAGATGATACCGTCGACG
```

5.13.7 Nucleic Acid Sequence the Entire Wheat Plastid
ACCase cDNA ACCase P1 (SEQ ID NO:7)

```
GATCTCGTTATCAATGACATCCAATGTCCATAGTCAGGAAACCATGACTATCTGTTGATC

AACGAGCTAGTCAACTAGAGGCTTACTAGGGACATGTTGGTGTCTATGAATTCACACATG

TATTACGATTTCCGGATAACACAATTATAGCATGAATAAAAGACAATTATCATGAACAAG

GAAATATAATAATAATGCTTTTATTATTGCCTCTAGGGCATATTTCCAACATGCACCGTG

TCCGTAGTGTCTCTCGCTTCCTTGTCATCGACTCATGGGACACCCGGTACCCGGGAGCGC

CCCACCATCTTCTGCACGCATCCGCACACTTCTCCTTTGCACCGGTATCTCAATCGAGTT

ACCGGAACCGGAACATTGCCGTGGCACCGTTTTCGTTATCGTTGTCGTGGCACCCCTTTT

CTTTCCACCACGGTGACAAATGCTTCATAATGCTCTTGTCAACTTTTAATAAAAATTGCA

TAAATTTGCACATGTCATCCGCATCATGATAAAAACAATTAAAATGTTTAAAATTGTTGT

TTGCATTAAATTGCTAAATGCACATGAGGATTTACCGGAATTGTTGTTTGATGTTTTCGG

CCTCATTTAAAATGCCTAACTGTGTATTTTACTTATGCTTCACCTCTTGCCATGCTAACC

AACATTTAATATTGTTGAGTACATAAACGGGAGAGAACTAAATAAGTCATGTGGTGTTCC

ATCAATATGCAACTCGTTGCATATTGAGCTCCACTTAATTTGTAGTTTTGCTTGTTGCAC

TTTGCCATGCCATGCATATTTAAACCGGACATGCATCATCTTTGATTGTGCATCATGCCA

TGTTTATGCTTGTTGGTTTACCATGTTGTTTTCTTCTTTCCGGTGTTGTTTCTTCGGATT

AGTTCCGATAACATCGCGTTCGTGGGATTCGTTCGACTACGTTCGTTTGTTTCTTCTTC

ATGGACTCATTCTTCTTCCTTGCGGGATCTCAGGCAAGATGACCATATCCTCGAAATCAC

TTCTATCTTTGCTTGCTAGTTGCTCGCTCTATTGCTATGCTGCGATACCTACCACTTGCT

TTATCATGCCTCCCATATTGCCATGTCAAGCCTCTAACCCACCCTTCCTAGCAAACCGTT

GTTTGGCTATGTTACCGCTTTGCTCAGCCCCTCTTATAGCATTGCTAGTTGCAGGCGAAG

ACGAAGTTTGTTCCATGTTTGAAACATGGATATGTTGGGATATCACAATATCTCTTATTT

ATATTAATGCATCTATATACTTGGTAAAGGGTGGAAGGCTCGGCCTTATGCCTGGTGTTT

TGTTCCACTCTTGCCGCCCTAGTTTCCGTCATACCAGTGTTATGTTCCTTGATTTTGCGT

TCCTTACACGGTTGGGTGTTATGGGAACCCCTTGATAGTTCGCTTTGAATAAAACTCCTC

CAGCAAGGCCCAACCTTGGTTTTACATTTGCCTTACCTAGCCTTTTTCCCTTGGGTTTCC

AGAGCCCGAGGGTCATCTTTATTTTAACCCCCCGGGCCAGTGCTTCTCTAAGTGTTGGT

CCAACCTGAGCGATGTCCGGCGCCCCTGGGCAACCAGGGTCTATGCCAACCCGATGTCT

GGCTCATCCGGTGTGCCCTGAGAATGAGATATGTGCAGCTCCTATCGGGATTTGTCGGCA

CATCGGACGGCTTTGCTGGTCTTGTTTTACCATTGTTGAAATGTCTTGTAACCGGGATTC

CGAGTCTGATCGGGTTTTCCTGGGAGAAGGAATATCCTTTGTTGACCGTGAGAGCTTGTG

ATGGGCTAAGTTGGGACACCCCTGCAGGGTTTTGAACTTTTGAAAGCCGTGCCCGCGGTT

ATGGGCAGATGGGGATTTGTTAATATCCGGTTGTAGAAAACATGACACTTAACTTAATTT

AAAATGCATCAACCGCGTGTGTAGCCGTGACGGTCTCTTTCCGGCGGAGTCCGGGAAGTG

AACACGGTTCTTGTGTTATGCTTCAACGTAAGTAGTTTCAGGATCACTTCTTGACCACTT

TTAGTTCCTCGCCCGTGCTTTGCTTCTCTTATCGCTCTCATTTGCGTAAGTTAGCCACCA

TATATGCTAGTGCTTGCTGCAGCTCCACCTCACTACCTCTTACCTACCCATAAGCTTAAA

TAGTCTTGATCTCGCGGGTGTGAGATTGCTGAGTCCCCATGACTCACAGATTACTTCCAA

AACCAGTTGCAGGTGCCGTTGATACCAGTGCAGATGACGCAGCTGAGCTCAAGTGGGAGC
```

-continued

```
TCGATGAAGACCATGTTTGTTGTGTTGTTTCGTTTCTTTTCGTTCAGTAGTGGAGCCCAG
TTGGGGCGATCGGGGATCTAGCATGAGGGGTGGTCTTCTTTTATTTTGGTTCCGTAGTCG
GACCTTGATTGTATTCTGAATGATGTAATGCTATATTTATGTATTGTGTGAAGTGGCGAT
TGTAAGCCAACTCTGTATCCCTTTGTTATTCAGTACATGAGATGTGTAAAGATTATCCCT
CTTGCGACATGCCTACCATGTAGTTATGCCTCTAAGTCATGCTCCGACACGTGGATGTTA
CAACATCCCTCACACCGTATGTTCAAACTCAAGCAGGAAGTATCCATGTCGTCCTATGGG
GGTCACGAGCTAGAACTAACCGAACCGTTCGTAAAGCCCCATGGTTGTCCTCGCGTGCTT
GCCCTACCTCCCTCACACAGACACTGGGCGAGGCGAAGTCCCTAAAGAAACTGATACATG
CACTATTTTTTGTAACATGGTAGTAATCACGCCTTTAAAACGAGCACAACAGATGAAGTT
AGGAGGTTGATTTGCGTTCAATAATGTAACCGTGTATCATACTGTACAAAGTTTCAAAAT
CCAAATTAAATGTCGAGAATCATTATTAGGTGAGCTTAGACCTACAGAATAGAACATGAA
CGCATGTATTCCGATGACAAAGGAGGAGGAACCAAGTGAGTTCACCCTAACCTAATCATG
GCGACAACCAACATCCATTAAAGTGGCGAGAGGAGGTTCATGCCCAGATTTCGGGTATTC
GGGGGAAAGAAACGGTTGTGCCCCTCATGTTGGAGCAACGATGACGTTGCTTCTGTGCTA
GGTGCAAGGCAACGCCGTTTGCCAGCACATTGGAAGTAAACATAGGGTTATGAGGAAAGG
GGCGAGGGAAATTGGATTGAGACAAGGAAGGGTGCTGGCATGATCAAGAGACGATGTGAT
CATTGTGAAGGAGGTACTGTGGCCCACACGTCGGCATACAATTGCGATGGGATAAGGCGG
GTGCAGAGTATGCACCATGAAAGATCACATACAATCGCCTACCCCCTTCAACAAGATGAC
CGAACACCACCGACGAGTTAAAACCAAAGATACACGGGACCTGCCAAAAAAAGGGTTCAA
GCGCGTACATTAACAAAACCGTTTATGGCTCCCAATCAAAACCTAGGAATCATGTACTTA
TATATTTTACATAAGCACGATAGGACGATGTCGAACGGACGCCACAATCGCCAACCATGA
TCGAACACCACCCAAAGCCACGAGCGCAGAGCAACGAAAAGTCGACGTGTTCCCCGAAAT
TACGCGTGCCCATAAACAGAACCTCCCGACATCGTCGACGACGACGACGACCAGCTCCAA
CAACAGAAACGGCACACGCGTTTCACACACTGTTTTCTCCGGTGGCGACGACGTTGCGCA
TGGCAGGAAGGAATGTCACGATCGCCCAACCACTAAACCTTAATCCAACAACGACACTGT
TCTAATCCACCTATGACGTTCTCCCCCTACGGCCGCCTGCCACCGTCCTCCAAACCGGGA
CACGCCAAGACGCGCCGCGAGAGAGCGAGCGACCACGACCCATCACAATCACAATCACAA
GGAGAGAAAAATCAAAACCCAAACCCCACGGCCAGCGCGGCGGGCAGGGGGCAGCGTGGG
AGCCGTCGGATGGGCGGATCGGGGCCGTCCGCTTGGCGGGGCGATGGGCGTCACGTGCGG
GGGCGCCAGGGGGAGGCGGAGTCCCCGAAGAGGGCCGGGAATTTATTATTTTAGGCCGCA
CAGCCCCCATCTCCGTCCCTCTCCCCTCACCCCCTCGGGATATCCGCCCGCGCTCCACTC
TCCCCCCGTCTCCGGCACCGTGCGCGCCGCCGCCGCGCTAAGATCCAGCCCCTCGTCCG
CTCCGCCACGCGCQAGCGCCCAGCACGCGTCGGCCCGTCCGCCCCCGCCGCCCCCGAGGT
GCGCCTCTATTTATCTCTTTCCCCCCTCGCGTCTCCCCCCATTCCCCCTGTCGCTTCCCC
CCAGGTCAGGTCAGGTCAGGCCAGGCCAGATCCGCCGCCCGATCCGCCTCCGCTCCCGGA
GGTGAGCCCGGCCGCCTTGGTCCGCCGTTGCTCTGTTTCCCGCGCGCTGAGCTGGGCAC
TGCTTAGGGTGCTTCGTCCGTGGGTGGCGGGAGAGGGTTTAAGGGTTCTGCCCCGCGCG
GGACTTACTGTACTAGGTGTTTGAAATTACGCGGAGCTTGGGATTGGGTTCTTCGGAGCT
TGCGCTGGCATGCTTCGTGTTCATGAGTGCTCATGGAGGGAGTAATTATGGAATGTGGCT
CCCGTACTGTATGCACAGTAGACAATTATCGGTGATTATGGCTGGTGTGGCTCGTTGGAG
```

-continued

```
GTGCCCTGCGCGTGCCTAACACTGTATTTCTTAGGTTAGGACGGTGTGCTTCCATGGACA
CATGCTCATGCTGAGTGCAAGCTCACCCAGGGTGGTTGCACAACGACACGGTCATACATG
GGTAGCGCGGTCCAGTGTTGTAGTCAGTTTGCCGCCGTACGCATGCGAGGCAGGTGTTGT
TTCTGCCGTGTTGATGCTACCGGCTGTCATAATGCACTTTGAGTGTTAGTATTGAGCTGG
AAATGGTAGATGCTGTTTTTTCCCTTCTCTCCCCCTCTCACCTGTTGATCTAGCTGCTGT
AATACTTTACCTGCCATCTTTTCTTTTTTGGCTGCATGTATTAGCTGTGAAAGCTTAGAA
TCATTTGCCTTGTACTTTTTGTACGAACCTGTGTCATAGGAGTAATTGCACACGTTATCT
GTTTTGGTCAAGAGCATCTTGGATGTTCAAACTTACAGAGGAAGGTCATGAATTAGCCCA
TAAAGTACTTGTGTCTTGTCTCTGTGAACTAACAATTTGTATTCACATGCATCTGTCAGG
TTCCAAGACCTGGGGTTTACACACCTTTGATGGCACTGTCTCTTTGAAGAACACTGCATC
TGCGCTGTTTGTCCAAAGGGAGGACGATGGGATCCACACATTTGCCCATCGTCGGCTTTA
ATGCCTCAACAACACCATCGCTATCCACTATTCGCCCGGTAAATTCAGCTGGTGCTGCAT
TCCAACCATCTGCCCCTTCTAGAACCTCCAAGAAGAAAAGTCGTCGTGTTCAGTCATTAA
GGGATGGAGGCGATGGAGGCGTGTCAGACCCTAACCAGTCTATTCGCCATGGTAACAACC
TGAAAACCATTTCCTTTCTACAAACTACACTTTGTTGTCATCCTCAGACTTGTGTAGATA
CTTTTATTGACTGAGAGCATGTTGGTTTTAGTGTAAGGTATCTCAATGCTAGATCACAGA
ATGGCGGTTATTGACCTCGTTAAAGATGCAAATGACTGCAGCAATATTTAACAATTTTTT
TATGTGATACGATAGTACTTTTTTATAACGAGTAATGAGTAAAGCCCAGTTTTTCTTGAT
TAAATGGTTTTAGTGGAAGGAATGTTTAATATTCAAAATGATGTTTTATAAGGGAAGGAA
CATGAAAGTGCAAGAATACTTTTTTATAACGAGTAATGAGTAAAGCCCAGTTTTTCTTGA
TTAAATGGTTTTAGTGGAAGGAATGTTTAATATTCAAAATGATGTTTTATAAGGGAAGGA
ACATGAAAGTGCAAGAATACATATAAGCAGCATATTAGTTATGTATGACTGAGTCATTTT
CCTTATATAATACTTCTAAAAGAGAAGAATGTCTAGAAACCTTTTCTGATAATTTACTAG
CATGAAGAACAATAACATTCATAAAGTTGTCACCTGTGCTTCTTCTTAGCTATCGTGTAA
ACTTGCTCAGTTTCTAATGCATATCTGGATGTAGGTCTTGCCGGCATCATTGACCTCCCA
AAGGAGGGCACATCAGCTCCGGAAGTGGATATTTCACAGTAAGTACTTTAGCATTTTAAA
ATTAGAATTAGCATCTCTCTTTAAAATGGAAAAATATCTATAATTTAATATAGAATTATT
ATAGATTATGCTTATTTTATTATTCGCACATGCTGATATTTTGAATTGCATTTGATATAT
TTTTATAGATTTTTACTGAACTACTCCCTCCGTAAACTAATATAAGAGCGTTTAGAACAC
TATTTTAGTGATCTAAACACTCTTATATTGGTTTACAGAGGGAGTACATTATAGTTGCCA
TACACAATGCATTTGCTCAGGCACATCACTGTTGCACTGCATGGAGTATTTTGTGCACT
TAGGAATCATTTTCAGAAAGCCTTTTGCCTATAATTTTAAAAATAATAATTTAATTACCA
TCTGAAACCCGTACCCACATGACGGATGAAAGCTCATTTGAAGTTTTCGATTTATAGTAG
CCAAGTATTTGTTATGTTATATTGTTATGGTCACCATCGTAATGAATTTGTTCTTTTTTC
TCTAGTGGGTCCGAAGAACCCAGGGGCTCCTACCAAATGAATGGGATACTGAATGAAGCA
CATAATGGGAGGCATGCTTCGCTGTCTAAGGTTGTTGAATTTTGTATGGCATTGGGCGGC
AAAACACCAATTCACAGTGTATTAGTTGCGAACAATGGAATGGCAGCAGCTAAGTTCATG
CGGAGTGTCCGAACATGGGCTAATGAAACATTTGGGTCAGAGAAGGCAATTCAGTTGATA
GCTATGGCTACTCCAGAAGACATGAGGATAAATGCAGAGCACATTAGAATTGCTGATCAA
TTTGTTGAAGTACCCGGTGGAACAAACAATAACAACTATGCAAATGTCCAACTCATAGTG
```

-continued

```
GAGGTTAGTATTGCTCATCCGTTGATGTGCAACCGATGCACAAGTTGTTCATTTAGCATG
ACATGACAATTTTGCTGTTGCAGATAGCAGTGAGAACCGGTGTTTCTGCTGTTTGGCCTG
GTTGGGGCCATGCATCTGAGAATCCTGAACTTCCAGATGCACTAAATGCAAACGGAATTG
TTTTTCTTGGGCCACCATCATCATCAATGAACGCACTAGGTGACAAGGTTGGTTCAGCTC
TCATTGCTCAAGCAGCAGGGGTTCCGACTCTTCCTTGGAGTGGATCACAGGTGAATCTCA
CATTCTCTGATAACTCATCGTCTGATCTTTGTACTGGACACATTTAAAAACCGAAAGACA
CTATATTATAGGTGGAAATTCCATTAGAAGTTTGTTTGGACTCGATACCTGCGGAGATGT
ATAGGAAAGCTTGTGTTAGTACTACAGAGGAAGCACTTGCGAGTTGTCAGATGATTGGGT
ATCCCGCCATGATTAAAGCATCATGGGGTGGTGGTGGTAAAGGGATCCGAAAGGTACATC
ATTCATTTGATTGGACTATATTTGAAAGATTGTGTGGGTTGTTGTGTGATATATTATGCC
CAGAGTTAGCTCTAACCTTTTCAACATATTAACTCAATATCTGTTGCAGGTTAATAATGA
CGATGATGTCAGAGCACTGTTTAAGCAAGTGCAAGGTGAAGTTCCTGGCTCCCCAATATT
TATCATGAGACTTGCATCTCAGGTTAGACTTCTCAGCAAGTTGCATTTTTTCCAAGCATG
TTATTCCCGAGTTGTATATTACACGCCTGGAAGCTTCATATGTTATTCCTTGCAGGCTAG
AAATGTATGCTGGAACATGTGCTCATATGGTATATTATGTTTTAATCCTCCCCTTTTTTC
TTTTGTAGAGTCGACATCTTGAAGTTCAGTTGCTTTGTGATCAATATGGCAATGTAGCTG
CGCTTCACAGTCGTGACTGCAGTGTGCAACGGCGACACCAAAAGGTAACGCTGGTCCAGA
TCTGAAAACATCACGTGTATTGCATGTTCTACTTCATACTTGTAGTTGTTTATCAAAAGG
ACCAATTGCGTCCATTTTTTGTTTATACCAGATTATTGAGGAAGGACCAGTTACTGTTGC
TCCTCGCGAGACAGTGAAAGAGCTAGAGCAAGCAGCAAGGAGGCTTGCTAAGGCTGTGGG
TTATGTTGGTGCTGCTACTGTTGAATATCTCTACAGCATGGAGACTGGTGAATACTATTT
TCTGGAACTTAATCCACGGTTGCAGGTATATTCTTTTGAACATTCCTCTGGACTTAGTTT
TTTGTCGTCAGTTATTTACATTGTTAAATGGCATACATCCAGGTTGAGCATCCAGTCACC
GAGTGGATAGCTGAAGTAAACTTGCCTGCAGCTCAAGTTGCAGTTGGAATGGGTATACCC
CTTTGGCAGGTTCCAGGTAATAATTATATTATTGTAAGTTTTTTAGTTACTTTCCCATGT
TACTTCTGTGCCTAACTTTCTCCTTATACAGAGATCAGACGTTTCTATGGAATGGACAAT
GGAGGAGGCTATGACATTTGGAGGACAACAGCAGCTCTTGCTACTCCATTTAACTTCGAT
GAAGTGGATTCTCAATGGCCAAAGGGTCATTGTGTAGCAGTTAGGATAACCAGTGAGGAT
CCAGATGACGGATTCAAGCCTACCGGTGGAAAAGTAAAGGTGAGATTTCATGATGCCGTC
TATGGTTCTAGCACATTAGATTTGTAAACTGACCGGACCTTGATTTTCTTATAATTCAGG
AGATCAGTTTTAAAAGCAAGCCAAATGTTTGGGCCTATTTCTCTGTTAAGGTAAGCTGTT
CATGGCTCTGTTGCACTGTTATATTGTTGAGTTGGGCTTTGACCAAGTATTAACCAAATC
GAACACATTTTTGTTCCCCCTTTTATCTGTTTTCAGTCCGGTGGAGGCATTCATGAATTT
GCTGATTCTCAGTTTGGTATGCAAAATTTGACCCTGTGAATATTCCTCTTTGCTATTTGT
ATTGGTCCTTACGTTTGGAAGATTACTCTTTTCATTTCAGGACATGTTTTTGCATATGGA
GTGTCTAGAGCAGCAGCAATAACCAACATGTCTCTTGCGCTAAAAGAGATTCAAATTCGT
GGAGAAATTCATTCAAATGTTGATTACACAGTTGATCTCTTGAATGTAAGAAATACTACC
TGTATATTGAATCCCTGCTTTTGATGTAATACAACCATTTTACATCTGGCATTCCTTTAA
```

5.13.8 Nucleic Acid Sequence the Entire Wheat Plastid
ACCase cDNA ACCase P2 (SEQ ID NO:8)

```
GATCCAGCCCCTCGTCCGCTCCGCCACGCGCCAGCGCCCAGCACGCGTCGGCCCGTCCGC

CCCCGCCGCCCCGCCCGAGGTGCGCCTCTATTTATCTCTTTCCCCCCTCGCGTCTCCCC

CCATTCCCCCTGTCGCTTCCCCCCATGTCAGGCCAGATCCGCCGCCCGATCCGCYTCAGC

TCCCGGAGGTGAGCCCGGCCGCCCGCCGCCTTCCTCCGCCGTTGCTCTGTTTCCAGCGGG

CCCAGCTGTGGCACTGCGTAGGGTGCTTCGTTCGTGGGTGGCGGGGAGAGGGTTTAAGGG

TTCTGCGCCTGCGCTGCTCTGCTCCGCCCGGGACTTACTGTACTAGGTGTTTGAAATTAT

GCGGAGCTTGGAATTGGGATCTTCGGAGCTTGCGCTGGCATGCTCCGTGTTCGTAAGTGC

TCATGGAGGGAGTAATTATGGAATGTGGCTCCCGCACTGTATGCACAGTAGTCAATTATC

GGTAATTATGGCTGGTGTGGCTCGCCGGAGCTGCCCTGTGCGTGCCTGCCACTGTATTTT

GTAGGTTGGGTCGGTGTGCTTCCATGGACACATGCTCATGCTAAGTGCAAGCTGACCCAG

GGTGGTTGCACAACGACACGGTGATACAGGGGTAGCGGTCCACTGTTGTAGCCAGTTTGC

CGCCGTACGCATGCCTTTTCTGCCGTTCAGTCTCCACTTCTTTGGGTGAGGGAGTCGCGT

ATCGTTTCGGTCGTGTTGATGCTACCTGCTGTCATAATGCACTGTGAGCAGTAGTATTGC

ACTGGGAATGGTAGTTGCTGTTTTTTCCCCCTCTCTCTCTAACCTGGTGATCTAGCCACC

CTATTACTTTGCCTGCCATCTTCTCTTTTTGGCTGCATGTGTTAGTTGTGAAAGCGTAGA

ATCATTTGCGTTGGTACTTGTTTTACGTACCTGTGTCATAGGAGTAATTGCACACGTTAT

CTGTTTTGGTCAAGAGCATCTTGGATGTTCAAACTTGCAGAGGAAGGTCATGAATTAGCC

CATAAAGTACTTGTGTCTTGTCTCTATGGACTAATAATTTGTATTCACATGCTTCTGTCA

GGTTTCAAAACCCGGGGTTTACACACCTTTGATGGCACTGTCTCTTTGAAGAACACTGCA

TCTGCGCTGTTTGTCCAAAGGGAGGACGATGGGATCCACACATTTGCCCATTGTCGGCCT

TAATGCCTCGACAACACCATCGCTATCCACTATTCGCCCGGTAAATTCAGCCGGTGCTGC

ATTCCAACCATCTGCCCCTTCTAGAACCTCCAAGAAGAAAAGTCGTCGTGTTCAGTCATT

AAGGGATGGAGGCGATGGAGGCGTGTCAGACCCTAACCAGTCTATTCGCCAAGGTAAACT

GAAAACCATTTCCTTCCTACAAACTACACTTTGTTGTCATCCTCAAACTTGTGTAGATAC

TTTTATTGACTGAGAGCATGCTGGTGTTAGTGTAAGATATCTCAATGCTAGATCACAGAA

TGGCGGTTATTGACCTTGTTAAAGATGCAAATGACTGCAGCAATATTTAACACTTTTTA

TGCGATACAAATACAATAGTAGTTCTTCTATATAATGAGTAATGAGTAAAGCCCAGTTTT

TCTTGATTAAATGGTTTTAGTGGAAGGAATGTTTAATGTTCAAAATGATGGTTTATAAGG

GAAAGGAACATGAAAGTGCAAGAATACATATAAGCAGCATATTAGTTATGCAAGACTGAA

TCATTTTCCTTATATAATACTTCTAAAAGAGAAGGATGTCTAGAAACCTTTTCTGATAAT

TTACTAGCATGAAGAACAATAACATTCGTAAATTGACACCTGTGCTTCTTCTTAGCTATC

GTGTTGCTCAGTTTCTAATGCATATCTGGATGTAGGTCTTGCCGGCATCATTGACCTCCC

AAAGGAGGGCACATCAGCTCCGGAAGTGGATATTTCACAGTAAGTACTTGAGCATTTTAA

AATTAGAATTAGCATATCTCTCTTTAAAAAGGAAAAATATGTATAGTTTAATATAGAATT

ATTATAGATTATGCTTATTTTATTATTCGCATATGCTGATATTTTGAATTGCATTTGATA

TATTTTTATAGATTTTTACTGAACTACATTATAGTTGCCATACACAATGCATTTGCTCAG

GCACATCACTGTTGCACTGCATGGAGTATTTTTGTGCACTTAGGAATCATTTTCAGAAAG

CCTTTTGCCTATAATTTTAAAAATAATAATTTAATTACCATCTGAAACCCGTACCCGCAT
```

```
GACGGATGAAAGCTCATTTGAAGTTTTCGATTTATAGTAGCCAAGTGTTTGTTATGTTAT
ATTGTTATGGTCACCATCGTAATGATTTTGTTCTTTTTTCTCTAGTGGGTCCGAAGAACC
CAGGGGCTCCTACCAZATGAATGGGATACTGAATGAAGCACATAATGGGAGGCATGCTTC
GCTGTCTAAGGTTGTCGAATTTTGTATGGCATTGGGCGGCAAAACACCAATTCACAGTGT
ATTAGTTGCGAACAATGGAATGGCAGCAGCTAAGTTCATGCGGAGTGTCCGAACATGGGC
TAATGAAACATTTGGGTCAGAGAAGGCAATTCAGTTGATAGCTATGGCTACTCCAGAAGA
CATGAGGATAAATGCAGAGCACATTAGAATTGCTGATCAATTTGTTGAAGTACCCGGTGG
AACAAACAATAACAACTATGCAAATGTCCAACTCATAGTGGAGGTTAGTATTGCTCACCC
GTTGATGTGCAATTGATGCGCAAGTTGTTCATTTAGCATGACATGACAATTTTGCTGTTG
CAGATAGCAGTGAGAACCGGTGTTTCTGCTGTTTGGCCTGGTTGGGGCCATGCATCTGAG
AATCCTGAACTTCCAGATGCACTAAATGCAAACGGAATTGTTTTTCTTGGGCCACCATCA
TCATCAATGAACGCACTAGGTGACAAGGTTGGTTCAGCTCTCATTGCTCAAGCAGCAGGG
GTTCCGACTCTTCCTTGGAGTGGATCACAGGTGAATCTCACATTCTCTGATAACTCATCG
TCTGATCTTTGTACTGGACACATTTTATAACAGAAAGACACTATATTATAGGTGGAAATT
CCATTAGAAGTTTGTTTGGACTCGATACCTGCGGAGATGTATAGGAAAGCTTGTGTTAGT
ACTACGGAGGAAGCACTTGCGAGTTGTCAGATGATTGGGTATCCAGCCATGATTAAAGCA
TCATGGGGTGGTGGTGGTAAAGGGATCCGAAAGGTACATCATTCATTTGATTGGACTATA
TTCAAAAGATTGTGTGGGTTGTTGTGTGATATTTTATGCCCAGAGTTAGCTCTAACCTTT
TCAACATATTAACTCAATATCTGTTGCAGGTTAATAACGACGATGATGTCAGAGCACTGT
TTAAGCAAGTGCAAGGTGAAGTTCCTGGCTCCCAATATTTATCATGAGACTTGCATCTC
AGGTTAGACTTCTCTGCAAGTTGCATTTTTTCCAAGCATGTTGTTCCCGAGTTGTATATT
ATACGCCTGGAAGCTTCATATGTTATTCCTTGCAGGCTAGAAATGTATGCTGGAACATGT
GCTCATATGGTATATTATGTTTTAATCCTCCCCTTTTTCTTTTGTAGAGTCGACATCTT
GAAGTTCAGTTGCTTTGTGATCAATATGGCAATGTAGCTGCGCTTCACAGTCGTGACTGC
AGTGTGCAACGGCGACACCAAAAGGTAACGCTGGTCCAGATCTGAAAACATCACGTGTAT
TACATGTTCTACTTCATACTTGTAGTTGTTTATCAAAAGGACCAATTGCGTCCATTTTTT
GTTTATACCAGATTATTGAGGAAGGACCAGTTACTGTTGCTCCTCGCGAGACAGTGAAAG
AGCTAGAGCAAGCAGCAAGGAGGCTTGCTAAGGCTGTGGGTTATGTTGGTGCTGCTACTG
TTGAATATCTCTACAGCATGGAGACTGGTGAATACTATTTTCTGGAACTTAATCCACGGT
TGCAGGTATATTCTTTTGAACATTCCTCTGGACTTAGTTTTTTGTCGTCAGTTATTTACA
TTGTTAAATGGCATACATCCAGGTTGAGCATCCAGTCACCGAGTGGATAGCTGAAGTAAA
CTTGCCTGCAGCTCAAGTTGCAGTTGGAATGGGTATACCCCTTTGGCAGGTTCCAGGTAA
TAATTATATTATTGTAAGTTTTTTAGTTACTTTCCCATGTTATTTCTGTGCCTAACTTTC
TCCTTATACAGAGATCAGACGTTTCTATGGAATGGACAATGGAGGAGGCTATGACATTTG
GAGGAAAACAGCAGCTCTTGCTACCCCATTTAACTTTGATGAAGTGGATTCTCAATGGCC
AAAGGGTCATTGTGTAGCAGTTAGGATAACCAGTGAGGATCCAGATGACGGATTCAAGCC
TACCGGTGGAAAAGTAAAGGTGAGATTTCATGATGCCGTCTATGGTTCTAGCACATTAGA
TTTGTAAACTGACCGGATCTTGATTTTCTTATAATTCAGGAGATCAGTTTTAAAAGCAAG
CCAAATGTTTGGGCCTATTTCTCTGTTAAGGTAAGCTGTTCATGGCTCTGTTGCACTGTT
ATATTGTTGAGTTGGGCAGAAAATTGGGCTGCGTTTTTTTGAACTATTTTTTCCATTTG
```

-continued
```
GGCTTTGACCAAGTACTAACCAAATCGAACACATTTTTGTCCCCCCTTTTATCTGTTTTC

AGTCCGGTGGAGGCATTCATGAATTTGCTGATTCTCAGTTTGGTATGCAAAATTTGACCC

TGTGTATATTCCTCTTTGCTATTTGTATTGGTCCTTACGTTTGGAAGATTACTCTTTTCA

TTACAGGACATGTTTTTGCATATGGAGTGTCTAGAGCAGCAGCAATAACCAACATGTCTC

TTGCGCTAAAAGAGATTCAAATTCGTGGAGAAATTCATTCAAATGTTGATTACACAGTTG

ATCTCTTGAATGTAAGAAATACCTCCTGTATATGCTTTTGATGTAATACAACCATTTTAC

ATCTGGCATTCCTTTAAA
```

5.14 Example 14

Amino Acid Sequence of the Wheat Plastid ACCase (SEQ ID NO:9)

```
MGSTHLPIVGLNASTTPSLSTIRPVNSAGAAFQPSAPSRTSKKKSRRVQSLRDGGDGGVS

DPNQSIRQGLAGIIDLPKEGTSAPEVDISHGSEEPRGSYQMNGILNEAHNGRHASLSKVV

EFCMALGGKTPIHSVLVANNGMAAAKFMRSVRTWANETFGSEKAIQLIAMATPEDMRINA

EHIRIADQFVEVPGGTNNNNYANVQLIVEIAVRTGVSAVWPGWGHASENPELPDALNANG

IVFLGPPSSSMNALGDKVGSALIAQAAGVPTLPWSGSQVEIPLEVCLDSIXAEMYRKACV

STTEEALASCQMIGYXAMIKASWGGGGKGIRKVNXDDDVRALFKQVQGEVPGSPIFIMRL

ASQSRHLEVQLLCDQYGNVAALHSRDCSVQRRHQKIIEEGPVTVAPRETVKELEQAARRL

AKAVGYVGAATVEYLYSMETGEYYFLELNPRLQVEHPVTEWIAEVNLPAAQVAVGMGIPL

WQVPEIRRFYGMDNGGGYDIWRKTAALATPFNFDEVDSQWPKGHCVAVRITSEDPDDGFK

PTGGKVKEISFKSKPNVWAYFSVKSGGGIHEFADSQFGHVFAYGVXXAAAITNMSLALKE

IQIRGEIHSNVDYTVDLLNASDFKENRIHTGWLDNRIAMRVQAERPPWYISVVGGALYKT

ITSNTDTVSEYVSYLVKGQIPPKHISLVHSTVSLNIEESKYTIETIRSGQGSYRLRMNGS

VIEANVQTLCDGGLLMQLDGNSHVIYAEEEAGGTRLLIDGKTCLLQNDHDPSRLLAETPC

KLLRFLVADGAHVEADVPYAEVEVMKMCMPLLSPAAGVINVLLSEGQPMQAGDLIARLDL

DDPSAVKRAEPFNGSFPEMSLPIAASGQVHKRCATSLNAARMVLAGYDHPINKVVQDLVS

CLDAPELPFLQWEELMSVLATRLPRLLKSELEGKYSEYKLNVGHGKSKDFPSKMLREIIE

ENLAHGSEKEIATNERLVEPLMSLLKSYEGGRESHAHFIVKSLFEDYLSVEELFSDGIQS

DVIERLRQQHSKDLQKVVDIVLSHQGVRNKTKLILTLMEKLVYPNPAVYKDQLTRFSSLN

HKRYYKLALKASELLEQTKLSELRTSIARSLSELEMFTEERTAISEIMGDLVTAPLPVED

ALVSLFDCSDQTLQQRVJETYISRLYQPHLVKDSIQLKYQESGVIALWEFAEAHSEKRLG

AMVIVKSLESVSAAIGAALKGTSRYASSEGNIMHIALLGADNQMHGTEDSGDNDQAQVRI

DKLSATLEQNTVTADLRAAGVKVISCIVQRDGALMPMRHTFLLSDEKLCYEEEPVLRHVE

PPLSALLELGKLKVKGYNEVKYTPSRDRQWNIYTLRNTENPKMLHRVFFRTLVRQPGASN

KFTSGNISDVEVGGAEESLSFTSSSILRSLMTAIEELELHAIRTGHSHMFLCILKEQKLL

DLVPVSGNKVVDIGQDEATACLLLKEMALQIHELVGARMHHLSVCQWEVKLKLDSDGPAS

GTWRVVTTNVTSHTCTVDIYREVEDTESQKLVYHSAPSSSGPLHGVALNTPYQPLSVIDL

KRCSARNNRTTYCYDFPLAFETAVQKSWSNISSDTNRCYVKATELVFAHKNGSWGTPVIP

MERPAGLNDIGMVAWILDMSTPEYPNGRQIVVIANDITFRAGSFGPREDAFFETVTNLAC

ERKLPLIYLAANSGARTGIADEVKSCFRVGWSDDGSPERGFQYIYLTEEDHARISASVIA
```

-continued

```
HKMQLDNGEIRWVIDSVVGKEDGLGVENJHGSAAIASAYSRAYEETFTLTFVTGRTVGIG

AYLARLGIRCIQRTDQPIILTGFSALNKLLGREVYSSHMQLGGPKIMATNGVVHLTVSDD

LEGVSNILRWLSYVPANIGGPLPITKSLDPPDRPVAYIPENTCDPRAAISGIDDSQGKWL

GGMFDKDSFVETFEGWAKSVVTGRAKLGGIPVGVIAVETQTMMQLIPADPGQLDSHERSV

PRAGQVWFPDSATKTAQAMLDFNREGLPLFILANWRGFSGGQRDLFEGILQAGSTIVENL

RTYNQPAFVYIPKAAELRGGAWVVIDSKINPDRIEFYAERTAKGNVLEPQGLIEIKFRSE

ELQECMGRLDPELINLKAKLQGVKHENGSLPESESLQKSIEARKKQLLPLYTQIAVRFAE

LHDTSLRMAAKGVIKKVVDWEDSRSFFYKRLRRRISEDVLAKEIRGVSGKQFSHQSAIEL

IQKWYLASKGAETGSTEWDDDDAFVAWRENPENYQEYIKELRAQRVSQLLSDVADSSPDL

EALPQGLSMLLEKMDPSRRAQFVEEVKKVLK
```

6. REFERENCES

The references listed below and all references cited herein are incorporated herein by reference to the extent that they supplement, explain, provide a background for, or teach methodology, techniques, and/or compositions employed herein.

U.S. Pat. No. 4,683,195.
U.S. Pat. No. 4,683,202.
U.S. Pat. No. 4,757,011.
U.S. Pat. No. 4,769,061.
U.S. Pat. No. 4,940,835.
U.S. Pat. No. 4,965,188.
U.S. Pat. No. 4,971,908.
U.S. Pat. No. 5,176,995.
U.S. Pat. No. 5,384,253.
Intl. Pat. Appl. Publ. No. WO/9110725, Jul. 25, 1991, by Lundquist et al.,
Abdullah et al., *Biotechnology*, 4:1087, 1986.
Abu-Elheiga et al., *Proc. Natl. Acad. Sci. USA*, 92:4011–4015, 1995.
Al-Feel et al., *Proc. Natl. Acad. Sci. USA*, 89:4534–4538, 1992.
Alban et al., *Plant. Physiol.*, 102:957–965, 1993.
Alix, *DNA*, 8:779–789, 1989.
Anderson et al., *Plant Physiol.*, 109:338, 1995.
Ashton et al., *Plant Mol. Biol.*, 24:35–49, 1994.
Ausubel, F. M. et al., "Current Protocols in Molecular Biology," John Wiley & Sons, New York, 1989.
Benbrook et al., *In: Proceectings Bio Expo 1986*, Butterworth, Stoneham, Mass., pp. 27–54, 1986.
Berry-Lowe et al., *Cell Cult. Somat. Cell Genet. Plants*, Vol. 7A, pp 257–302, Academic Press, New York, 1991.
Best and Knauf, *J. Bacteriol*, 175:6881–6889, 1993.
Betty et al., *J. Plant. Physiol.*, 140:513–520, 1992.
Bowness et al., *Eur. J. Immunol.*, 23:1417, 1993.
Brichard et al. *J. Exp. Med.*, 178:489, 1993.
Brock et al., "Biology of Microorganisms" 7th Edition, Prentice Hall, Inc., Englewood Cliffs, N.J., 1994.
Browner et al., *J. Biol. Chem.*, 264:12680–12685. 1989.
Bytebier et al., *Proc. Natl. Acad. Sci. USA*, 84:5345, 1987.
Callis et al., *Genes and Developmnent*, 1:1183, 1987.
Campbell, "Monoclonal Antibody Technology, Laboratory Techniques in Biochemistry and Molecular Biology," Vol. 13, Burden and Von Knippenberg, Eds. pp. 75–83, Eilsevier, Amsterdam, 1984.
Capecchi, M. R., *Cell* 22(2):479–488, 1980.
Cashmore et al., *Gen. Eng. of Plants*, Plenum Press, New York, 29–38, 1983.
Cavener and Ray, *Nucl. Acids Res.*, 19:3185–3192, 1991.
Charng et al., *Plant Mol. Biol.*, 20:37–47, 1992.
Chau et al., *Science*, 244:174–181, 1989.
Chen et al., *Arch. Biochem. Biophys.*, 305:103–109, 1993.
Chen, Yang, Kuo, *Curr. Genet.*, 21:83–84, 1992.
Chirala, *Proc Natl Acad Sci USA*, 89:10232–10236, 1992.
Chirgwin et al., *Biochenmistry*, 18:5294–5304, 1979.
Christianson, Sikorski, Dante, Shero, Hieter, *Gene*, 110:119–122, 1992.
Clapp, *Clin. Perinatol.* 20(1):155–168, 1993.
Clark and Lamppa, *Plant Physiol.*, 98:595–601, 1992.
Cristou et al., *Plant Physiol*, 87:671–674, 1988.
Curiel et al., *Hum. Gen. Ther.* 3(2):147–154, 1992.
Curiel et al., *Proc. Natl. Acad. Sci. USA* 88(19):8850–8854, 1991.
Dean and Leech, *Plant Physiol.*, 69:904–910, 1982.
Dhir et al., *Plant Cell Reports*, 10:97, 1991.
Dibrino et al., *J. Immunol.*, 152:620, 1994.
Egin-Buhler et al., *Arch. Biochem. Biophys.*, 203 :90–100, 1980.
Egin-Buhler et al., *Eur. J. Biochem.*, 133:335–339, 1983.
Egli et al., *Plant Physiol.*, 108:1299–1300, 1995.
Egli et al., *Plant. Physiol.*, 101:499–506, 1993.
Eglitis and Anderson, *Biotechniques* 6(7):608–614, 1988.
Eglitis et al., *Adv. Exp. Med. Biol.* 241:19–27, 1988.
Elborough et al., *Plant Mol. Biol.*, 24:21–34, 1994.
Feel et al., *Proc Natl Acad, Sci USA*, 89:4534–4538, 1992.
Fernandez and Lamppa, *J. Biol. Chem.*, 266:7220–7226, 1991.
Fraley et al., *Biotechnologyp*, 3:629. 1985.
Fraley et al., *Proc. Natl. Acad. Sci. USA*, 80:4803, 1983.
Fromm et al., *Nature*, 319:791, 1986.
Fromm et al., *Proc. Natl. Acad. Sci. USA* 82(17):5824–5828. 1985.
Fu et al., *Plant Cell*, 7:1387–1394, 1995.
Fujimura et al., *Plant Tissue Culture Letters*, 2:74, 1985.
Fynan et al., *Proc. Natl. Acad. Sci. USA* 90(24):11478–11482, 1993.
Gallie, *Annu. Rev. Plant Physiol. Plant Mol. Biol.*, 44:77–105, 1993.
Gefter et al., *Somatic Cell Genet.* 3:231–236, 1977.
Gendler et al., *J. Biol. Chem.*, 263:12820, 1988.
Gill, Gill, Endo, *Chromosoma*, 102:374–381, 1993.
Gill, Lubbers. Gill, Raupp, Cox, *Genome*, 34:362–374, 1991.
Goding, "Monoclonal Antibodies: Principles and Practice," pp. 60–74. 2nd Edition, Academic Press, Orlando, Fla., 1986.
Golden et al., *Methods Enzymol.*, 153:215–231, 1987.

Golz, Focke, Lichtenthaler, *J. Plant Physiol.*, 143:426–433, 1994.
Goodal et al., *Methods Enzymol.*, 181:148–161, 1990.
Gordon-Kamm et al., *The Plant Cell*, 2:603–618, 1990.
Gornicki and Haselkorn," *Plant Mol. Biol.*, 22:547–552, 1993.
Gornicki et al., *J. Bacteriol.*, 175:5268–5272, 1993.
Gornicki et al., *Proc. Natl. Acad. Sci. USA*, 91:6860–6864, 1994.
Graham and van der Eb, *Virology*, 54(2):536–539, 1973.
Grimm et al., *J. Exp. Med.*, 155:1823, 1982.
Guan and Dixon, *Anal. Biochem.* 192:262–267, 1991.
Guthrie and Fink, *In: Methods of Enzymology*, eds. Vol. pp. 21–37, 1991.
Ha et al., *Eur. J. Biochem.*, 219:297–306, 1994.
Ha et al., *J. Biol. Chem.*, 269:22162–22168, 1994.
Hardie et al., Trends in Biochem. Sci., 14:20–23, 1989.
Harlow and Lane. "Antibodies: A laboratory Manual," C.old Spring Harbor Laboratory, Cold Spring Harbor, N.Y., 1988.
Harwood."*Ann. Rev. Physiol. Plant Mol. Biol.*, 39:101–138, 1988.
Haslacher et al., *J. Biol. Chem.*, 268:10946–10952, 1993.
Haymerle et al., *Nucl. Acids Res.*, 14:8615–8629, 1986.
Hess, *Intern Rev. Cytol.*, 107:367, 1987.
Hilber et al., *Curr. Genet.* 25(2):124–127, 1994.
Hill et al., *Nature*, 360:434, 1992.
Hoffman and Winston, *Gene.* 57:267–272, 1987.
Hogquist et al., *Eur. J. Immunol.*, 23 :3028–3036, 1993.
Holt et al., *Annu. Rev. Plant. Physiol. Plant Mol. Biol.*, 44:203–229, 1993.
Horsch et al., *Science*, 227:1229–1231, 1985.
Howard and Ridley, *FEBS Letters*, 261:261–264, 1990.
Hu et al., *J. Exp. Med.*, 177:1681, 1993.
Jacobson et al., *J. Virol.*, 63:1756, 1989.
Jahnen-Dechent and Simpson, *Plant Mol. Biol. Rep.*, 8:92–103, 1990.
Jameson and Wolf, *Compu. Appl. Biosci.*, 4(1):181–6, 1988.
Jerome et al., *J. Immunol.*, 151:1654, 1993.
Jerome et al., *Cancer Res.*, 51:2908, 1991.
Joachimiak et al., *Proc Natl Acad Sci USA*, 94:9990–9995, 1997.
Johnston and Davis, *Mol. Cell. Biol.*, 4:1440–1448, 1984.
Johnston and Tang, *Methods Cell. Biol.* 43(A):353–365, 1994.
Jorgensen et al., *Mol. Gen. Genet.*, 207:471, 1987.
Joshi and Nguyen, *Nucl. Acids Res.*, 23:541–549, 1995.
Kaiser and Kezdy, *Science*, 223:249–255, 1984.
Kam-Morgani, Gill, Muthukrishnan, *Genome*, 32:724–732, 1989.
Kang et al., *Proc. Natl. Acad. Sci. USA*, 88:4363–4366, 1991.
Karow et al., *J. Bacteriol.*, 174:7407–7418, 1992.
Keller et al., *EMBO J.*, 8:1309–14, 1989.
Kim, *Ann Rev Nutrition*, 17:XXX—XXX, 1997.
Klapholz and Esposito, *Genetics*, 100:387–412, 1982.
Klapholz, Wadell., Esposito. *Genetics*, 110:187–216, 1985.
Klee et al., *In: Plant DNA Infectious Agents*. T. Hohn and J. Schell, eds., Springer-Verlag, New York pp. 179–203, 1985.
Klein et al., *Nature*, 327:70, 1987.
Klein et al., *Plant Physiol.*, 91:440–444, 1989.
Klein et al., *Proc. Natl. Acad. Sci. USA*, 85:8502–8505, 1988.
Knowles, *Annu. Rev. Biochem.*, 58:195–221. 1989.
Kohler and Milstein, *Eur. J. Immnol.* 6:511–519, 1976.
Kohler and Milstein, *Nature* 256:495–497, 1975.
Kondo et al., *Proc Natl Acad Sci USA*, 88:9730–9733, 1991.
Konishi and Sasaki, *Proc. Natl. Acad. Sci. USA*, 91:3598–3601, 1994.
Konishi et al., *Plant Cel Physiol*, 37:117–122. 1996.
Kos and Mullbacher, *Eur. J. Immunol.*, 22:3183, 1992.
Kosambi, *Ann. Eugen.*, 12:172–175, 1994.
Kozak, *Annu. Rev. Cell. Biol.*, 8:197–925, 1992.
Kozak, *J. Cell Biol.*, 115:887–903, 1991.
Kyte and Doolittle, *J. Mol. Biol.*, 157:105–132, 1982.
Lamppa et al., *Mol. Cell Biol.*, 5:1370–1378, 1985.
Lander, Green, Abrahamson, Barlow, Daly, Lincoln, Newburg, *Genomics*, 1:174–181, 1987.
Langridge et al., *Proc. Natl. Acad. Sci. USA*, 86:3219–3223, 1989.
Letessier et al., *Cancer Res.*, 51:3891, 1991.
Li and Cronan, *J. Bacteriol.*, 175:332–340, 1993.
Li and Cronan, *J. Biol. Chem.*, 267:855, 1992.
Li and Cronan, *Plant Mol. Biol.* 20:759–761, 1992.
Lichtenthaler, *Z. Naturforsch.*, 45c:521–528, 1990.
Lim et al., *J. Biol. Chem.*, 263:11493–11497, 1988.
Lindstrom et al., *Developl Genet.*, 11:160, 1990.
Liu and Roizman, *J. Virol.*, 65:5149–5156, 1991.
Lopez-Casillas et al., *Proc. Natl. Acad. Sci. USA*, 85:5784–5788, 1988.
Lorz et al., *Mol. Gen. Genet.*, 199:178, 1985.
Lu et al., *J. Exp. Med.* 178(6):2089–2096, 1993.
Luo et al., *Plant Mol. Biol. Reporter*, 6:165, 1988.
Luo et al., *Proc. Natl. Acad. Sci. USA*, 86:4042–4046, 1989.
Maddock et al., *Third International Congress of Plant Molecular Biology*, Abstract 372, 1991.
Maloy et al., "Microbial Genetics" 2nd Edition. Jones and Barlett Publishers, Boston, Mass., 1994.
Maloy, S. R., "Experimental Techniques in Bacterial Genetics" Jones and Bartlett Publishers, Boston, Mass., 1990.
Maniatis et al., "Molecular Cloning: A Laboratory Manual." Cold Spring Harbor Laboratory, Cold Spring Harbor, N.Y., 1982.
Marcotte et al., *Nature*, 335:454, 1988.
Marincola et al., *Cancer Res.*, 83:932, 1991.
Marshall et al., *Theor. Appl. Genet.*, 83:435–442, 1992.
McCabe et al., *Biotechnology*, 6:923, 1988.
Mitchell, Marshall, Desehenes, *Yeast*, 9:715–722, 1993.
Mundy, Mayer, Chua, *Plant Mol. Biol. Rep.*, 13:156–163, 1995.
Muramatsu and Mizuno, *Nucleic Acids Res.*, 17:3982, 1989.
Murata and Nishida, In. P. K. Stumpf (ed.), *The Biochemistry of Plants*, Academic Press, Inc., New York, 9:315–347, 1987.
Neuhaus et al., *Theor. Appl. Genet.*, 75:30, 1987.
Norman et al., *J. Bacteriol.*, 176:2525–2531, 1994.
Odell et al., *Nature*, 313:810, 1985.
Ohlrogge and Jaworski, *Annu Rev Plant Physiol Mol Biol*, 48:109–136, 1997.
Ohno, *Proc. Natl. Acad. Sci. USA*, 88:3065, 1991.
Omirulleh et al., *Plant Molecular Biology*, 21:415–428, 1993.
Page et al., *Biochem. Biophys. Acta*, 1210:369–372, 1994.
Pecker et al., *Proc Natl Acad Sci USA*, 89:4962–4666, 1992.
Pena et al., *Nature*, 325:274, 1987.
Podkowinski. Sroga, Haselkorn, Gornicki, *Proc. Natl. Acad. Sci. USA*, 93:1870–1874, 1996.
Post-Beitenmiller et al., *Plant Physiol.*, 100:923–930, 1992.
Poszkowski et al., *EMBO J.*, 3:2719, 1989.
Potrykus et al., *Mol. Gen. Genet.*, 199:183, 1985.
Poulsen et al., *Mol. Gen. Genet.*, 205:193–200, 1986.
Quaedvlieg et al., *The Plant Cell*, 7:117–129, 1995.
Ratner and Clark, *J. Immunol.*, 150:4303, 1993.

Rawn, "Biochemistry" Harper & Row Publishers, New York, 1983.
Riede and Anderson, *Crop. Sci.*, 36:905–909, 1996.
Rippka et al., *J. Gen. Microbiol.*, 170:4136–4140, 1979.
Roesler et al., *Plant Physiol.*, 105:611–617, 1994.
Roessler and Ohlrogge, *J. Biol. Chem.* 268:19254–19259, 1993.
Rogers et al., *In: Methods For Plant Molcular Biology*, A. Weissbach and H. Weissbach, eds., Academic Press Inc., San Diego, Calif. 1988.
Rogers et al., *Meth. in Enzymol.*, 153:253–277, 1987.
Sambrook et al., "Molecular Cloning: A Laboratory Manual," Cold Spring Harbor Laboratory, Cold Spring Harbor, N.Y., 1989.
Samols et al., *J. Biol. Chem.*, 263:6461–6464, 1988.
Sasaki et al., *J. Biol. Chem.*, 268:25118–25123, 1993.
Sasaki et al., *Plant Physiol.*, 108:445–449, 1995.
Schneider and Haselkorn, *J. Bacteriol.* 170:4136–4140, 1988.
Schneiter, Hitomi, Ivessa, Fasch, Kohlwein, Taitakoff, *Mol. Cell. Biol.*, 16:7161–7172, 1996.
Schulte et al., *Plant Physiol.*, 106:793–794, 1994.
Schulte. Topfer, Strackc, Schell, Martini, *Proc. Natl. Acad. Sci. USA*, 94:3465–3470, 1997.
Scoble et al., "Mass spectrometric strategies for structural characterization of proteins," *In: A practical guide to protein and peptid purification for microsequencing.* P. Matsudaira, ed., pp 125–153, Academic Press, New York, 1993.
Scott. *TIBS*, 17:241–245, 1992.
Sears and Sears, *Abhrev. Journal*, 389–407, 1978.
Sears, *In: Chromosome manipulation and plant genetics.*, eds. Riley, Lewis (Oliver and Boyd, Edinburg), pp. 29–45, 1966.
Segal, "Biochemical Calculations" 2nd Edition. John Wiley & Sons, New York, 1976.
Sheen, *Plant Cell.* 21027–1038, 1990.
Shenoy et al., *J. Biol. Chem.*, 267:18407–18412, 1992.
Sherman et al., *J. Exp. Med.*, 175:1221, 1992.
Shintani and Ohlrogge, *Plant J.*, 7:577–587, 1995.
Shorrosh et al., *Plant Physiol.*, 108:805–812, 1995.
Shorrosh el al., *Proc. Natl. Acad. Sci. USA*, 91:4323–4327, 1994.
Simpson, *Science*, 233 :34, 1986.
Slabas and Fawcett, *Plant Mol. Biol.*, 19:169–191, 1992.
Slabas and Hellyer, *Plant Sci.* 39:177–182, 1985.
Somers et al., *Plant Physiol.*, 101:1097–1101, 1993.
Somerville and Browse, *Science*, 252:80–87, 1991.
Spielmann et al., *Mol. Gen. Genet.*, 205:34, 1986.
Steinman, *Annu. Rev. Immunol.*, 9:271, 1991.
Suhrbier et al., *J. Immunol.*, 150:2169, 1993.
Takai et al., *J. Biol. Chem.*, 263:2651–2657, 1988.
Toh et al., *Eur. J. Biochem.*, 215:687–696, 1993.
Tomes et al., *Plant Mol. Biol.*, 14:261–268, 1990.
Toriyama et al., *Theor Appl. Genet.*, 73:16, 1986.
Uchimiya et al., *Mol. Gen. Genet.*, 204:204, 1986.
Van Tunen et al., *EMBO J.*, 7:1257, 1988.
Vasil et al., *Biotechnology*, 10:667–674, 1992.
Vasil, *Biotechnology*, 6:397, 1988.
Vodkin et al., *Cell*, 34:1023, 1983.
Vogel et al., *J. Cell Biochem.*, (Suppl) 3D:312, 1989.
Wagner et al., *Proc. Natl. Acad. Sci. USA* 89(13) :6099–6103, 1992.
Weaver et al,. *Plant Physiol.*, 107:1013–1014, 1995.
Weissbach and Weissbach *Methods for Plant Molecular Biology*, (Eds.), Academic Press, Inc., San Diego, Calif., 1988.
Wenzler et al., *Plant Mol. Biol.*, 12:41–50, 1989.
White et al., *Plant Mol. Biol.*, 19:1057–1064, 1992.
Winter et al., *J. Immunol.*, 146:3508, 1991.
Winz et al., *J. Biol. Chem.*, 269:14438–14445, 1994.
Witters and Kemp, *J. Biol. Chem.*, 267:2864–2867, 1992.
Wolf et al., *Compu. Appl. Biosci.*, 4(1):187–91 1988.
Wolfel et al., *Int. J. Cancer*, 54:636, 1993.
Wong and Neumann, *Biochim. Biophys. Res. Commum.* 107(2):584–587, 1982.
Wood. R. A., "Metabolism," In Manual of Methods for General Bacteriology, ((Gerhardt, Murray, Costilow, Nester, Wood, Krieg, and Phillips, Eds.) American Society for Microbiology, Washington, D.C., 1981.
Wurtele and Nikolau, *Arch. Biochem. Biolphys.*, 278:179–186, 1990.
Wurtele and Nikolau, *Plant. Physiol.*, 99:1699–1703, 1992.
Yamada et al., *Plant Cell Rep.*, 4:85, 1986.
Yanai et al., *Plant Cell Physiol.*, 36:779–787, 1995.
Yang et al., *Proc. Natl. Acad. Sci. USA*, 87:4144–48, 1990.
Young and Davis, *Proc. Natl. Acad. Sci. USA*, 80:1194–1198, 1983.
Zatloukal et al., *Ann. N.Y. Acad. Sci.* 660: 136–153, 1992.
Zhou et al., *Methods in Enzymology*, 101:433. 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

7. SEQUENCE LISTING

What is claimed is:

1. A purified nucleic acid segment having the nucleic acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8; or a nucleic acid segment encoding a wheat acetyl-CoA carboxylase comprising the amino acid sequence of SEQ ID NO:9.

2. The nucleic acid segment of claim 1, further defined as comprising SEQ ID NO:6.

3. The nucleic acid segment of claim 1, defined further as a recombinant vector.

4. The nucleic acid segment of claim 1, wherein said nucleic acid segment is operatively linked to a promoter.

5. The nucleic acid segment of claim 4, wherein said promoter is a plant or yeast promoter.

6. The nucleic acid segment of claim 5, wherein said promoter is a GAL promoter.

7. The nucleic acid segment of claim 6, wherein said promoter is a GAL10 promoter.

8. The nucleic acid segment of claim 5, wherein said promoter is a tissue specific promoter.

9. The nucleic acid segment of claim 4, wherein said segment complements a yeast ACC1 null mutation.

10. A purified nucleic acid segment having the nucleic acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8; or a nucleic acid segment encoding a wheat acetyl-CoA carboxylase comprising the amino acid sequence of SEQ ID NO:9, wherein said segment comprises a null mutation.

11. A host cell comprising the nucleic acid segment of claim 1.

12. The host cell of claim 11, defined further as being a prokaryotic cell.

13. The host cell of claim 12, further defined as a bacterial or cyanobacterial host cell.

14. The host cell of claim 11, defined further as being a eukaryotic cell.

15. The host cell of claim 14, further defined as a yeast cell or a plant host cell.

16. The host cell of claim 15, wherein said cell is a monocotyledonous plant cell.

17. The host cell of claim 13, wherein the bacterial host cell is *E. coli*.

18. The host cell of claim 15, wherein said yeast cell is a *Saccharomyces cerevisiae* cell.

19. The host cell of claim 18, wherein said *Saccharomyces cerevisiae* cell comprises an ACC1 null mutation.

20. The host cell of claim 19, wherein said ACC1 null mutation comprises an ACC1 deletion.

21. The host cell of claim 11, wherein said nucleic segment is introduced into said cell by means of a recombinant vector.

22. The host cell of claim 11, wherein said host cell expresses said nucleic acid segment to produce said encoded acetyl-CoA carboxylase protein or peptide.

23. The host cell of claim 11, wherein said expressed acetyl-CoA carboxylase protein or peptide comprises the amino acid sequence of SEQ ID NO:9.

24. A method of producing an acetyl CoA-carboxy polypeptide comprising:

(a) introducing into a host cell a nucleic acid segment having a nucleic acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8; and (b) culturing said host cell under conditions permitting transcription and translation of said acetyl CoA-carboxylase polypeptide from said nucleic acid sequence.

25. The method of claim 24, wherein said host cell is a prokaryotic cell.

26. The method of claim 24, wherein said host cell is a eukaryotic cell.

27. The method of claim 24, further comprising the step of isolating said polypeptide.

28. The method of claim 27, wherein said polypeptide is purified to homogeneity.

* * * * *

UNITED STATES PATENT AND TRADEMARK OFFICE
CERTIFICATE OF CORRECTION

PATENT NO.     : 6,306,636 B1
DATED          : November 7, 2001
INVENTOR(S)    : Robert H. Haselkorn and Piotr Gornicki It is certified that error appears in the above-identified patent and that said Letters Patent is hereby corrected as shown below:

<u>Column 150,</u>
Line 38, please delete "acetyl CoA-carboxy" and insert -- acetyl-CoA carboxylase -- therefor.
Line 45, please delete "acetyl CoA-carboxylase" and insert -- acetyl-CoA carboxylase -- therefor.

Signed and Sealed this

Twenty-first Day of January, 2003

JAMES E. ROGAN
*Director of the United States Patent and Trademark Office*